United States Patent
Zhang et al.

(10) Patent No.: US 10,087,157 B2
(45) Date of Patent: Oct. 2, 2018

(54) SEMI-SYNTHESIS PROCEDURES

(71) Applicant: Tetraphase Pharmaceuticals, Inc., Watertown, MA (US)

(72) Inventors: Wu-Yan Zhang, Lexington, MA (US); Danny LaFrance, Natick, MA (US); Magnus P. Ronn, Melrose, MA (US)

(73) Assignee: Tetraphase Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 15/521,162

(22) PCT Filed: Oct. 23, 2015

(86) PCT No.: PCT/US2015/057167
§ 371 (c)(1),
(2) Date: Apr. 21, 2017

(87) PCT Pub. No.: WO2016/065290
PCT Pub. Date: Apr. 28, 2016

(65) Prior Publication Data
US 2017/0334872 A1    Nov. 23, 2017

Related U.S. Application Data

(60) Provisional application No. 62/067,697, filed on Oct. 23, 2014.

(51) Int. Cl.
*C07D 295/15* (2006.01)
*C07C 231/12* (2006.01)
*C07C 245/20* (2006.01)
*C07C 237/26* (2006.01)

(52) U.S. Cl.
CPC .......... *C07D 295/15* (2013.01); *C07C 231/12* (2013.01); *C07C 237/26* (2013.01); *C07C 245/20* (2013.01); *C07C 2603/46* (2017.05)

(58) Field of Classification Search
None
See application file for complete search history.

(56) References Cited

U.S. PATENT DOCUMENTS 3,239,499 A    3/1966   Rennhard et al.

FOREIGN PATENT DOCUMENTS

| GB | 935 384 A | 8/1963 |
|---|---|---|
| WO | WO-2010/017470 A1 | 2/2010 |
| WO | WO-2010/126607 A2 | 11/2010 |
| WO | WO-2012/047907 A1 | 4/2012 |
| WO | WO-2016/065290 A1 | 4/2016 |

OTHER PUBLICATIONS

Furuya et al., "Carbon-Fluorine Bond Formation for the Synthesis of Aryl Fluorides," Synthesis, 2010(11): 1804-1821 (2010).
Heredia-Moya et al., "Photochemical Schiemann Reaction in Ionic Liquids," J Fluorine Chem, 128(6): 674-678 (2007).
Hlavka et al., "The 6-Deoxytetracyclines. IV. A Photochemical Displacement of a Diazonium Group 1," J Org Chem, 27(10): 3674-3675 (1962).
International Preliminary Report on Patentability for International Application No. PCT/US2015/057167 dated May 4, 2017, 9 pages.
International Search Report and Written Opinino for International Application No. PCT/US2015/057167 dated Jan. 28, 2016, 16 pages.
Laali et al., "Fluorodediazoniation in Ionic Liquid Solvents: New Life for the Balz-Schiemann Reaction," J Fluorine Chem, 107(1): 31-34 (2001).
Nelson et al., "Versatile and Facile Synthesis of Diverse Semisynthetic Tetracycline Derivatives via Pd-Catalyzed Reactions," J Org Chem, 68(15): 5838-5851 (2003).

*Primary Examiner* — Kamal Saeed
(74) *Attorney, Agent, or Firm* — Foley Hoag LLP

(57) ABSTRACT

Provided herein are improved processes for convening C7-amino-substituted tetracylines to C7-fluoro-substituted tetracyclines as well as intermediates produced by or used in these processes. In one embodiment, a thermal fluorination method is provided in which a suspension comprising a non-polar organic solvent and a C7-diazo-substituted tetracycline hexafluorophosphate, hexafluoarsenate or hexafluorosilicate salt, or a salt, solvate or combination thereof, is healed to provide a C7-fluoro-substituted tetracyline, or salt, solvate or combination thereof. In another embodiment, a photolytic fluorination is provided in which a solution comprising an ionic liquid and a C-7diazo-substituted tetracyline tetrafluoroborate, hexafluorophosphate, hexafluoroarsenate or hexafluorosilicate salt, or a salt, solvate or combination thereof, is irradiated to provide a C7-fluoro-substituted tetracyline, or salt, solvate or combination thereof.

11 Claims, No Drawings

SEMI-SYNTHESIS PROCEDURES

RELATED APPLICATION

This application is the U.S. National Stage of International Application No. PCT/US2015/057167, filed Oct. 23, 2015, which designates the U.S., published in English, and claims the benefit of U.S. Provisional Application No. 62/067,697, filed on Oct. 23, 2014. The entire teachings of the above applications are incorporated herein by reference.

BACKGROUND OF THE INVENTION

Eravacycline is a tetracycline antibiotic that has demonstrated broad spectrum activity against a wide variety of multi-drug resistant Gram-negative, Gram-positive and anaerobic bacteria in humans. In Phase I and Phase II clinical trials, eravacycline also demonstrated a favorable safety and tolerability profile. In view of its attractive pharmacological profile, synthetic routes to eravacycline and, in particular, synthetic routes that result in suitable quantities of eravacycline for drug development and manufacturing, are becoming increasingly important.

As described in International Publication No. WO 2010/017470, eravacycline is conveniently synthesized from 7-fluorosancycline, another tetracycline. 7-Fluorosancycline can be synthesized, in turn, from commercially available 7-aminosancycline or a protected derivative thereof. However, very few procedures for the conversion of C7-amino-substituted tetracyclines, such as 7-aminosancycline, to C7-fluoro-substituted tetracyclines, such as 7-fluorosancycline, have been reported, and those that have are not suitable to be deployed at production-scale.

Therefore, there is a need for improved processes, particularly improved production-scale processes, for converting C7-amino-substituted tetracyclines to C7-fluoro-substituted tetracyclines.

SUMMARY OF THE INVENTION

Provided herein are improved processes for converting C7-amino-substituted tetracyclines to C7-fluoro-substituted tetracyclines, as well as intermediates produced by or used in these processes.

One embodiment is a compound represented by Structural Formula I:

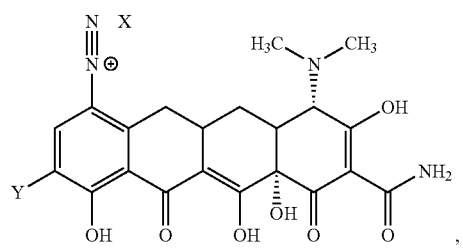

or a salt, solvate or combination thereof, wherein values for the variables are as described and defined herein.

Another embodiment is a method of preparing a compound represented by Structural Formula II:

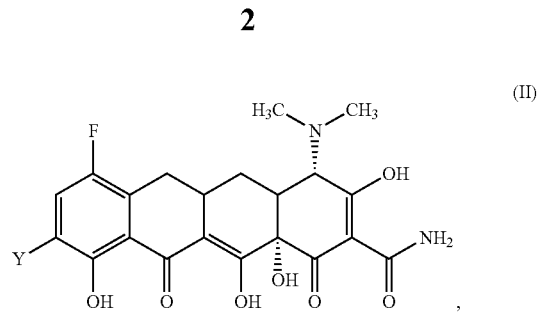

or a salt, solvate or combination thereof, by thermal fluorination. The method comprises heating a suspension comprising a non-polar organic solvent and a compound of Structural Formula I:

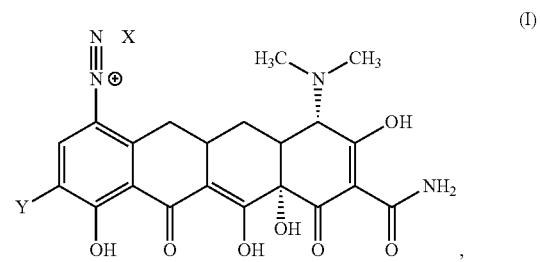

or a salt, solvate or combination thereof, at a temperature of from about 95° C. to about 200° C. to provide the compound of Structural Formula II, or the salt, solvate or combination thereof. Values for the variables are as described and defined herein.

Yet another embodiment is a method of preparing a compound represented by Structural Formula IIa:

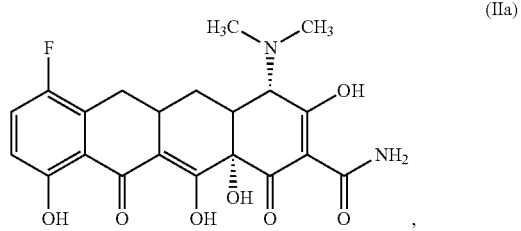 [SMILES: CN(C)[C@@H]1C(O)=C(C(N)=O)C(=O)[C@@]2(O)C(O)=C3C(=O)c4c(O)ccc(F)c4CC3CC12]

or a salt, solvate or combination thereof, the method comprising heating a suspension comprising a perfluorinated organic solvent and a compound of Structural Formula Ia:

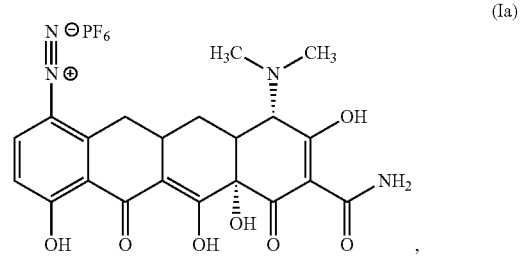

or a salt, solvate or combination thereof, at a temperature of from about 120° C. to about 160° C. to provide the compound of Structural Formula IIa, or the salt, solvate or combination thereof.

Another embodiment is a compound represented by Structural Formula X:

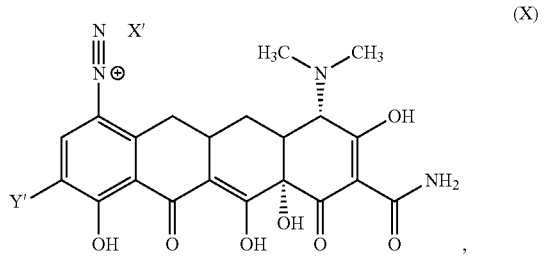

(X)

or a salt, solvate or combination thereof, wherein values for the variables are as defined and described herein.

Another embodiment is a method of preparing a compound represented by Structural Formula II, or a salt, solvate or combination thereof, by photolytic fluorination. The method comprises irradiating a solution comprising an ionic liquid and a compound of Structural Formula XI:

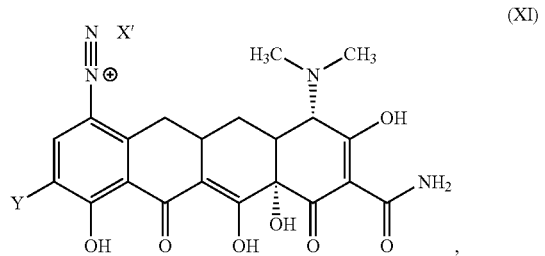

(XI)

or a salt, solvate or combination thereof, to provide the compound of Structural Formula II, or the salt, solvate or combination thereof. Values for the variables are as described and defined herein.

Yet another embodiment is a method of preparing a compound represented by Structural Formula IIa, or a salt, solvate or combination thereof, the method comprising irradiating a solution comprising an ionic liquid and a compound of Structural Formula XIa:

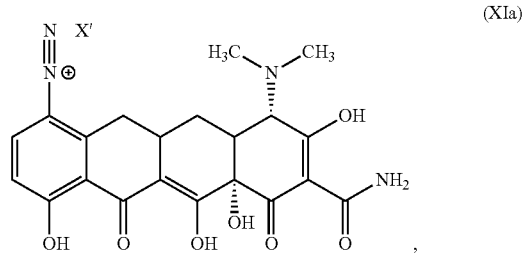

(XIa)

or a salt, solvate or combination thereof, to provide the compound of Structural Formula IIa or the salt, solvate or combination thereof. Values for the variables are as described and defined herein.

The fluorination methods described herein enable the plant scale production of 7-fluoro-substituted tetracyclines, such as 7-fluorosancycline from 7-amino-substituted tetracyclines, such as 7-aminosancycline, and represent dramatic improvements over known methods for converting C7-amino-substituted tetracyclines, such as 7-aminosancycline, to C7-fluoro-substituted tetracyclines, such as 7-fluorosancycline. In particular, the methods described herein significantly increase the yield and purity of the fluorination reaction, and give consistent access to C7-fluoro-substituted tetracyclines containing less than about 5% of undesired 7-H tetracycline side products. The enhanced purity of the fluorination reaction enables, for example, the chromatography-free isolation of 7-fluorosancycline in high purity, which results, in turn, in a high yield of 7-fluoro-9-nitrosancycline in the subsequent nitration step.

DETAILED DESCRIPTION OF THE INVENTION

A description of example embodiments of the invention follows.

Compounds, Salts and Solvates

A first embodiment is a compound represented by Structural Formula I:

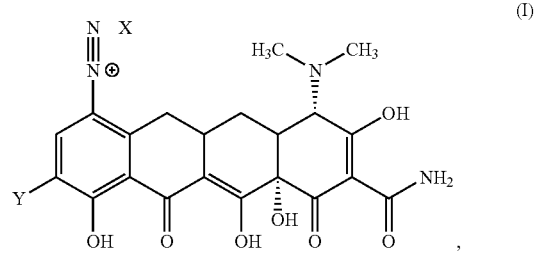

(I)

or a salt, solvate or combination thereof, wherein:

X is $PF_6^-$, $AsF_6^-$ or $HSiF_6^-$;

Y is selected from the group consisting of hydrogen, halo, nitro, —$(C_1$-$C_7)$alkyl, carbocyclyl, —$(C_1$-$C_4)$alkylene-N$(R^A)(R^B)$, —$(C_1$-$C_4)$alkylene-N$(R^F)$—C(O)—[C$(R^D)(R^E)]_{0-4}$—N$(R^A)(R^B)$, —CH=N—OR$^A$, —N$(R^A)(R^B)$, —N$(R^F)$—C(O)—[C$(R^D)(R^E)]_{1-4}$—N$(R^A)(R^B)$, —N$(R^F)$—C(O)—N$(R^A)(R^B)$, —N$(R^F)$—C(O)—OR$^A$, —N$(R^F)$—C(O)—$(C_1$-$C_6)$alkyl, —N$(R^F)$—C(O)-heterocyclyl, —N$(R^F)$—C(O)-heteroaryl, —N$(R^F)$—C(O)-carbocyclyl, —N$(R^F)$—C(O)-aryl, —N$(R^F)$—S(O)$_m$—$(C_1$-$C_4)$alkylene-N$(R^A)(R^B)$, —N$(R^F)$—S(O)$_m$—$(C_1$-$C_4)$alkylene-carbocyclyl, and —N$(R^F)$—S(O)$_m$—$(C_1$-$C_4)$alkylene-aryl (e.g., hydrogen, —$(C_1$-$C_7)$alkyl, carbocyclyl, —$(C_1$-$C_4)$alkylene-N$(R^A)(R^B)$, —$(C_1$-$C_4)$alkylene-N$(R^F)$—C(O)—[C$(R^D)(R^E)]_{1-4}$—N$(R^A)(R^B)$, —CH=N—OR$^A$, —N$(R^A)(R^B)$, —N$(R^F)$—C(O)—[C$(R^D)(R^E)]_{1-4}$—N$(R^A)(R^B)$, —N$(R^F)$—C(O)—N$(R^A)(R^B)$, —N$(R^F)$—C(O)—OR$^A$, —N$(R^F)$—C(O)—$(C_1$-$C_6)$alkyl, —N$(R^F)$—C(O)-heterocyclyl, —N$(R^F)$—C(O)-heteroaryl, —N$(R^F)$—C(O)-carbocyclyl, —N$(R^F)$—C(O)-aryl, —N$(R^F)$—S(O)$_m$—$(C_1$-$C_4)$alkylene-N$(R^A)(R^B)$, —N$(R^F)$—S(O)$_m$—$(C_1$-$C_4)$alkylene-carbocyclyl, and —N$(R^F)$—S(O)$_m$—$(C_1$-$C_4)$alkylene-aryl), wherein:

each $R^A$ and $R^B$ are independently selected from the group consisting of hydrogen, $(C_1$-$C_7)$alkyl, —O—$(C_1$-$C_7)$alkyl, —$(C_0$-$C_6)$alkylene-carbocyclyl, —$(C_0$-$C_6)$alkylene-aryl, —$(C_0$-$C_6)$alkylene-heterocyclyl, —$(C_0$-$C_6)$alkylene-heteroaryl, —$(C_1$-$C_6)$alkylene-O—$(C_1$-$C_7)$alkyl, —$(C_1$-$C_6)$ alkylene-O-carbocyclyl, —(C$_1$-C$_6$)alkylene-O-aryl, —(C$_1$-C$_6$)alkylene-O-heterocyclyl, —(C$_1$-C$_6$)alkylene-O-heteroaryl, —S(O)$_m$—(C$_1$-C$_6$)alkyl, —(C$_0$-C$_4$)alkylene-S(O)$_m$-carbocyclyl, —(C$_0$-C$_4$)alkylene-S(O)$_m$-aryl, —(C$_0$-C$_4$)alkylene-S(O)$_m$-heterocyclyl and —(C$_0$-C$_4$)alkylene-S(O)$_m$-heteroaryl; or R$^A$ and R$^B$ taken together with the nitrogen atom to which they are bound form a heterocyclyl or heteroaryl, wherein the heterocycle or heteroaryl optionally comprises 1 to 4 additional heteroatoms independently selected from the group consisting of N, S and O;

each R$^D$ and each R$^E$ is independently selected from the group consisting of hydrogen, (C$_1$-C$_6$)alkyl, carbocyclyl, aryl, heterocyclyl or heteroaryl, or R$^D$ and R$^E$ taken together with the carbon atom to which they are bound form a 3-7 membered carbocyclyl, or a 4-7 membered heterocyclyl, wherein the heterocyclyl formed by R$^D$ and R$^E$ optionally comprises one to two additional heteroatoms independently selected from the group consisting of N, S and O;

R$^F$ is selected from the group consisting of hydrogen, (C$_1$-C$_7$)alkyl, carbocyclyl, aryl and heteroaryl; and m is 0, 1 or 2, wherein:

each carbocyclyl, aryl, heterocyclyl or heteroaryl is optionally and independently substituted with one or more substituents independently selected from the group consisting of halo, —(C$_1$-C$_4$)alkyl, —OH, =O, —O—(C$_1$-C$_4$)alkyl, —(C$_1$-C$_4$)alkylene-O—(C$_1$-C$_4$)alkyl, halo-substituted —(C$_1$-C$_4$)alkyl, halo-substituted —O—(C$_1$-C$_4$)alkyl, —C(O)—(C$_1$-C$_4$)alkyl, —C(O)-(fluoro-substituted-(C$_1$-C$_4$)alkyl), —S(O)$_m$—(C$_1$-C$_4$)alkyl, —N(R$^G$)(R$^G$), and CN;

each alkyl in the group represented by R$^A$, R$^B$, R$^D$ and R$^E$ is optionally and independently substituted with one or more substituents independently selected from the group consisting of halo, —(C$_1$-C$_4$)alkyl, —OH, —O—(C$_1$-C$_7$)alkyl, —(C$_1$-C$_4$)alkylene-O—(C$_1$-C$_4$)alkyl, fluoro-substituted-(C$_1$-C$_4$)alkyl, —S(O)$_m$—(C$_1$-C$_4$)alkyl, and —N(R$^G$)(R$^G$), wherein each R$^G$ is hydrogen or (C$_1$-C$_4$)alkyl, wherein each alkyl in the group represented by R$^G$ is optionally and independently substituted with one or more substituents independently selected from the group consisting of —(C$_1$-C$_4$)alkyl, (C$_3$-C$_6$)cycloalkyl, halo, —OH, —O—(C$_1$-C$_4$)alkyl, and (C$_1$-C$_4$)alkyl-O—(C$_1$-C$_4$)alkyl.

In a first aspect of the first embodiment. X is PF$_6^-$. Values and alternative values for the remaining variables are as defined in the first embodiment.

In a second aspect of the first embodiment, Y is hydrogen. Values and alternative values for the remaining variables are as defined in the first embodiment, or first aspect thereof.

In a third aspect of the first embodiment, the compound of Structural Formula I is represented by Structural Formula Ib:

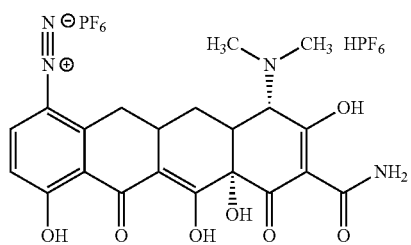

(Ib)

or a solvate thereof.

In a fourth aspect of the first embodiment, Y is selected from the group consisting of —N(R$^A$)(R$^B$), —N(R$^F$)—C(O)—[C(R$^D$)(R$^E$)]$_{1-4}$—N(R$^A$)(R$^B$), —N(R$^F$)—C(O)—N(R$^A$)(R$^B$), —N(R$^F$)—C(O)—(C$_1$-C$_6$)alkyl, —N(R$^F$)—C(O)-heterocyclyl, —N(R$^F$)—C(O)-heteroaryl, —N(R$^F$)—C(O)-carbocyclyl, —N(R$^F$)—C(O)-aryl, —N(R$^F$)—S(O)$_m$—(C$_1$-C$_4$)alkylene-N(R$^A$)(R$^B$), —N(R$^F$)—S(O)$_m$—(C$_1$-C$_4$)alkylene-carbocyclyl, and —N(R$^F$)—S(O)$_m$—(C$_1$-C$_4$)alkylene-aryl. Values and alternative values for the remaining variables are as defined in the first embodiment, or first aspect through third aspects thereof.

In a fifth aspect of the first embodiment, Y is —N(H)—C(O)—CH$_2$-pyrrolidin-1-yl. Values and alternative values for the remaining variables are as defined in the first embodiment, or first aspect through fourth aspects thereof.

In a sixth aspect of the first embodiment, the compound is represented by Structural Formula Ic:

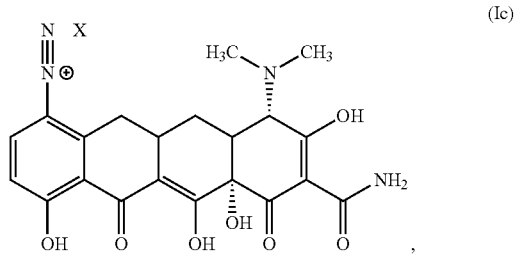

(Ic)

or a salt, solvate or combination thereof. Values and alternative values for the remaining variables are as defined in the first embodiment, or first through fifth aspects thereof.

In a seventh aspect of the first embodiment, the compound is represented by Structural Formula Ia:

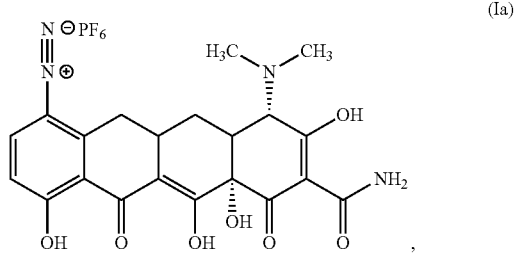

(Ia)

or a salt, solvate or combination thereof.

A second embodiment is a compound represented by Structural Formula I, or a salt, solvate or combination thereof, wherein Y is —N(R$^F$)—C(O)—CH$_2$—N(R$^1$)(R$^2$), wherein:

R$^1$ and R$^2$ are each independently selected from the group consisting of hydrogen, (C$_1$-C$_7$)alkyl, (C$_3$-C$_6$)cycloalkyl(C$_1$-C$_4$)alkyl, (C$_1$-C$_7$)alkoxy(C$_1$-C$_4$)alkyl, (C$_3$-C$_6$)cycloalkoxy(C$_1$-C$_4$)alkyl, (C$_3$-C$_6$)cycloalkyl, aryl, aryl(C$_1$-C$_4$)alkyl, aryloxy(C$_1$-C$_4$)alkyl, arylthio(C$_1$-C$_4$)alkyl, arylsulfinyl(C$_1$-C$_4$)alkyl, arylsulfonyl(C$_1$-C$_4$)alkyl, and —O—(C$_1$-C$_7$)alkyl; or R$^1$ and R$^2$ taken together with the nitrogen atom to which they are bonded form a monocyclic or bicyclic heteroaryl, or a monocyclic, fused bicyclic, bridged bicyclic or spiro bicyclic heterocycle, wherein the heteroaryl or heterocycle optionally contains one or two additional heteroatoms independently selected from the group consisting of N, O and S, wherein
each alkyl, cycloalkyl, alkoxy and cycloalkoxy moiety in the groups represented by $R^1$ and $R^2$ and each heterocycle represented by $NR^1R^2$ taken together is optionally substituted with one or more substituents independently selected from the group consisting of $(C_1-C_4)$ alkyl, halo, —OH, $(C_1-C_4)$alkoxy, $(C_1-C_4)$alkylthio, $(C_1-C_4)$alkylsulfinyl, $(C_1-C_4)$alkylsulfonyl, $(C_1-C_4)$ alkoxy$(C_1-C_4)$alkyl, and —$N(R^3)(R^4)$; and
each aryl, aryloxy, arylthio, arylsufinyl and arylsulfonyl moiety in the groups represented by $R^1$ and $R^2$ and each heteroaryl represented by $NR^1R^2$ taken together is optionally substituted with one or more substituents independently selected from the group consisting of $(C_1-C_4)$alkyl, halo, —OH, $(C_1-C_4)$alkoxy, —S—$(C_1-C_4)$alkyl, —$S(O)(C_1-C_4)$alkyl, —$S(O)_2(C_1-C_4)$alkyl, $(C_1-C_4)$alkoxy$(C_1-C_4)$alkyl, —$N(R^3)(R^4)$; —CN, halo$(C_1-C_4)$alkyl, and halo$(C_1-C_4)$alkoxy; and
$R^3$ and $R^4$ are each independently selected from the group consisting of —H and $(C_1-C_4)$alkyl, wherein the $(C_1-C_4)$alkyl represented by $R^3$ and $R^4$ is optionally substituted with one or more substituents independently selected from the group consisting of $(C_1-C_4)$alkyl, halo, —OH, $(C_1-C_4)$alkoxy, and $(C_1-C_4)$alkoxy$(C_1-C_4)$ alkyl. Values and alternative values for the remaining variables are as defined in the first embodiment, or any aspect thereof.

In a first aspect of the second embodiment, $R^1$ is hydrogen or $(C_1-C_4)$alkyl. Values and alternative values for the remaining variables are as defined in the first embodiment, or any aspect thereof, or the second embodiment.

In a second aspect of the second embodiment, $R^1$ is selected from the group consisting of hydrogen, methyl and ethyl. Values and alternative values for the remaining variables are as defined in the first embodiment, or any aspect thereof, or the second embodiment, or first aspect thereof.

In a third aspect of the second embodiment, $R^2$ is selected from the group consisting of $(C_1-C_7)$alkyl, $(C_1-C_6)$cycloalkyl$(C_1-C_4)$alkyl, $(C_1-C_7)$alkoxy$(C_1-C_4)$alkyl, phenyl, phenyl$(C_1-C_4)$alkyl, $(C_3-C_6)$cycloalkyl and halo$(C_1-C_4)$ alkyl, wherein each alkyl, alkoxy and cycloalkyl moiety in the groups represented by $R^2$ is optionally substituted with one or more substituents independently selected from the group consisting of $(C_1-C_4)$alkyl and halo; and each phenyl moiety in the groups represented by $R^2$ is optionally substituted with one or more substituents independently selected from the group consisting of $(C_1-C_4)$alkyl, halo, $(C_1-C_4)$alkoxy, $(C_1-C_4)$alkoxy$(C_1-C_4)$alkyl, —CN, halo$(C_1-C_4)$alkyl, and halo$(C_1-C_4)$alkoxy. Values and alternative values for the remaining variables are as defined in the first embodiment, or any aspect thereof, or the second embodiment, or first or second aspect thereof.

In a fourth aspect of the second embodiment, R is selected from the group consisting of cyclopropyl, cyclobutyl, cyclopentyl, cyclopropylmethyl, cyclobutylmethyl, phenyl, benzyl, —$(CH_2)_2$—O—$CH_3$, —$(CH_2)_3$—$OCH_3$, —$C(CH_3)_3$, —$CH(CH_3)_2$, —$CH_2C(CH_3)_3$, —$CH_2CH(CH_3)_2$, —$CH_2$—$CF_3$, —$(CH_2)_2$—$CH_2F$, and —$(CH_2)CH_3$; n is 0, 1, 2, 3, 4, 5 or 6; wherein the phenyl or benzyl group represented by $R^2$ is optionally substituted with one or two substituents independently selected from the group consisting of $(C_1-C_4)$alkyl, halogen, $(C_1-C_4)$alkoxy, $(C_1-C_4)$alkoxy$(C_1-C_4)$ alkyl, —CN, halo$(C_1-C_4)$alkyl, and halo$(C_1-C_4)$alkoxy. Values and alternative values for the remaining variables are as defined in the first embodiment, or any aspect thereof, or the second embodiment, or first through third aspects thereof.

In a fifth aspect of the second embodiment, $R^2$ is selected from the group consisting of cyclopropyl, cyclopropylmethyl, cyclobutyl, cyclopentyl, cyclohexyl, —$(CH_2)_2$—O—$CH_3$, —$C(CH_3)_3$, —$CH(CH_3)_2$, —$CH_2$—$CF_3$, —$CH_2CH$ $(CH_3)_2$, —$CH_3$ and —$CH_2CH_3$. Values and alternative values for the remaining variables are as defined in the first embodiment, or any aspect thereof, or the second embodiment, or first through fourth aspects thereof.

In a sixth aspect of the second embodiment, $R^1$ and $R^2$ taken together with the nitrogen atom to which they are bonded form a monocyclic or bicyclic heteroaryl, or a monocyclic, fused bicyclic, bridged bicyclic or spiro bicyclic heterocycle, wherein the heteroaryl or heterocycle optionally contains one additional heteroatom selected from the group consisting of N. O and S; and the heterocycle is optionally substituted with one or more substituents independently selected from the group consisting of $(C_1-C_4)$ alkyl, halo, —OH, $(C_1-C_4)$alkoxy, $(C_1-C_4)$alkylthio, $(C_1-C_4)$alkylsulfinyl, $(C_1-C_4)$alkylsulfonyl, $(C_1-C_4)$alkoxy$(C_1-C_4)$ alkyl, and —$N(R^3)(R^4)$; and the heteroaryl is optionally substituted with one or more substituents independently selected from the group consisting of $(C_1-C_4)$alkyl, halo, —OH, $(C_1-C_4)$alkoxy, —S—$(C_1-C_4)$alkyl, —$S(O)(C_1-C_4)$ alkyl, —$S(O)_2(C_1-C_4)$alkyl, $(C_1-C_4)$alkoxy$(C_1-C_4)$alkyl, —$N(R^3)(R^4)$, —CN, halo$(C_1-C_4)$alkyl, and halo$(C_1-C_4)$ alkoxy. Values and alternative values for the remaining variables are as defined in the first embodiment, or any aspect thereof, or the second embodiment, or first through fifth aspects thereof.

In a seventh aspect of the second embodiment, $R^1$ and $R^2$ taken together with the nitrogen atom to which they are bonded form a heterocycle selected from the group consisting of azetidine, pyrrolidine, morpholine, piperidine, octahydrocyclopenta[c]pyrrol, isoindoline, and azabicyclo [3.1.0]hexane, wherein the heterocycle is optionally substituted with one or more substituents independently selected from the group consisting of $(C_1-C_4)$alkyl, halogen, —OH, $(C_1-C_4)$alkoxy, —S—$(C_1-C_4)$alkyl, —$S(O)(C_1-C_4)$ alkyl, —$S(O)_2(C_1-C_4)$alkyl, $(C_1-C_4)$alkoxy$(C_1-C_4)$alkyl, and —$N(R^3)(R^4)$. Values and alternative values for the remaining variables are as defined in the first embodiment, or any aspect thereof, or the second embodiment, or first through sixth aspects thereof.

In an eighth aspect of the second embodiment, the heterocycle formed by $R^1$ and $R^2$ taken together with the nitrogen atom to which they are bonded is optionally substituted with halogen, methoxy, hydroxy, methoxymethyl or dimethylamino group. Values and alternative values for the remaining variables are as defined in the first embodiment, or any aspect thereof, or the second embodiment, or first through seventh aspects thereof.

In a ninth aspect of the second embodiment:
a) $R^1$ is methyl, and $R^2$ is cyclopropyl;
b) $R^1$ is hydrogen, and $R^2$ is cyclopropyl;
c) $R^1$ is hydrogen, and $R^2$ is cyclobutyl;
d) $R^1$ is methyl, and $R^1$ is cyclobutyl;
e) $R^1$ is hydrogen, and $R^2$ is cyclopropylmethyl;
f) $R^1$ is hydrogen, and $R^2$ is cyclobutylmethyl;
g) $R^1$ is hydrogen, and $R^2$ is benzyl;
h) $R^1$ is hydrogen, and $R^2$ is methoxypropyl;
i) $R^1$ is hydrogen, and $R^2$ is methoxyethyl;
j) $R^1$ is hydrogen, and $R^2$ is phenyl;
k) $R^1$ is methyl, and $R^2$ is t-butyl;
l) $R^1$ is hydrogen, and $R^2$ is t-butyl;
m) $R^1$ is hydrogen, and $R^2$ is methyl;
n) $R^1$ is hydrogen, and $R^2$ is ethyl;
o) $R^1$ is hydrogen, and $R^2$ is propyl;

p) $R^1$ is hydrogen, and $R^2$ is butyl;
q) $R^1$ is hydrogen, and $R^2$ is pentyl;
r) $R^1$ is hydrogen, and $R^2$ is hexyl;
s) $R^1$ is hydrogen, and $R^2$ is heptyl;
t) $R^1$ is methyl, and $R^2$ is methyl;
u) $R^1$ is hydrogen, and $R^2$ is isopropyl;
v) $R^1$ is hydrogen, and $R^2$ is 2,2-dimethylpropyl;
w) $R^1$ is hydrogen, and $R^2$ is trifluoroethyl;
x) $R^1$ is hydrogen, and $R^2$ is 2-methylpropyl;
y) $R^1$ is hydrogen, and $R^2$ is 3-fluoropropyl;
z) $R^1$ is ethyl, and $R^2$ is ethyl;
a1) $R^1$ is methyl, and $R^2$ is methyl;
b1) $R^1$ is hydrogen, and $R^2$ is hydrogen;
c1) $R^1$ is hydrogen, and $R^2$ is cyclopentyl;
d1) $R^1$ is methyl, and $R^2$ is cyclopentyl; or
e1) $R^1$ is methyl, and $R^2$ is propyl.

Values and alternative values for the remaining variables are as defined in the first embodiment, or any aspect thereof, or the second embodiment, or first through eighth aspects thereof.

In a tenth aspect of the second embodiment, $R^1$ and $R^2$ are taken together with the nitrogen atom to which they are bonded form a group selected from the group consisting of:
a) azetidin-1-yl;
b) 3-fluoroazetidin-1-yl;
c) 3-methylazetidin-1-yl;
d) 3-methoxyazetidin-1-yl;
e) pyrrolidin-1-yl;
f) morpholin-4-yl;
g) 3-fluoropyrrolidin-1-yl;
h) 3-hydroxypyrrolidin-1-yl;
i) 3-N,N-dimethylaminopyrrolidin-1-yl;
j) 2-methoxymethylpyrrolidin-1-yl;
k) piperidin-1-yl;
l) octahydrocyclopenta[c]pyrrol-2-yl;
m) isoindolin-2-yl; and
n) 3-azabicyclo[3.1.0]hexan-3-yl.

Values and alternative values for the remaining variables are as defined in the first embodiment, or any aspect thereof, or the second embodiment, or first through ninth aspects thereof.

In an eleventh aspect of the second embodiment:
$R^1$ is hydrogen or a $(C_1-C_4)$alkyl; and
$R^2$ is selected from the group consisting of $(C_1-C_7)$alkyl, $(C_3-C_6)$cycloalkyl$(C_1-C_4)$alkyl, $(C_1-C_7)$alkoxy$(C_1-C_4)$alkyl, phenyl, phenyl$(C_1-C_4)$alkyl, $(C_3-C_6)$cycloalkyl and halo$(C_1-C_4)$alkyl, wherein each alkyl, alkoxy and cycloalkyl moiety in the groups represented by $R^2$ is optionally substituted with one or more substituents independently selected from the group consisting of $(C_1-C_4)$alkyl and halo; and each phenyl moiety in the groups represented by $R^2$ is optionally substituted with one or more substituents independently selected from the group consisting of $(C_1-C_4)$alkyl, halo, $(C_1-C_4)$alkoxy, $(C_1-C_4)$alkoxy$(C_1-C_4)$alkyl, —CN, halo$(C_1-C_4)$alkyl, and halo$(C_1-C_4)$alkoxy; or
$R^1$ and $R^2$ taken together with the nitrogen atom to which they are bonded form a monocyclic or bicyclic heteroaryl, or a monocyclic, fused bicyclic, bridged bicyclic or spiro bicyclic heterocycle, wherein the heteroaryl or heterocycle optionally contains one additional heteroatom selected from the group consisting of N, O and S; and the heterocycle is optionally substituted with one or more substituents independently selected from the group consisting of $(C_1-C_4)$alkyl, halo, —OH, $(C_1-C_4)$alkoxy, $(C_1-C_4)$alkylthio, $(C_1-C_4)$alkylsulfinyl, $(C_1-C_4)$alkylsulfonyl, $(C_1-C_4)$alkoxy$(C_1-C_4)$alkyl, and —N($R^3$)($R^4$); and the heteroaryl is optionally substituted with one or more substituents independently selected from the group consisting of $(C_1-C_4)$alkyl, halo, —OH, $(C_1-C_4)$alkoxy, —S—$(C_1-C_4)$alkyl, —S(O)$(C_1-C_4)$alkyl, —S(O)$_2$($C_1$-$C_4$)alkyl, $(C_1-C_4)$alkoxy$(C_1-C_4)$alkyl, —N($R^3$)($R^4$), —CN, halo$(C_1-C_4)$alkyl, and halo$(C_1-C_4)$alkoxy. Values and alternative values for the remaining variables are as defined in the first embodiment, or any aspect thereof, or the second embodiment, or first through tenth aspects thereof.

In a twelfth aspect of the second embodiment:
$R^1$ is hydrogen, methyl, ethyl, methoxy or tert-butoxy;
$R^2$ is selected from the group consisting of $(C_1-C_7)$alkyl, $(C_3-C_6)$cycloalkyl$(C_1-C_4)$alkyl, $(C_1-C_7)$alkoxy$(C_1-C_4)$alkyl, phenyl, $(C_3-C_6)$cycloalkyl, and fluoro$(C_1-C_4)$alkyl; or
$R^1$ and $R^2$ taken together with the nitrogen atom to which they are bonded form a ring selected from the group consisting of pyrrolidinyl, morpholinyl, azetidinyl, piperidinyl, octahydrocyclopenta[c]pyrrolyl, isoindolinyl, indazolyl, imidazolyl, pyrazolyl, triazolyl, and tetrazolyl, wherein the ring formed by $R^1$ and $R^2$ taken together with the nitrogen atom to which they are bonded is optionally substituted with fluoro, —OH, —OCH$_3$, or N(CH$_3$)$_2$. Values and alternative values for the remaining variables are as defined in the first embodiment, or any aspect thereof, or the second embodiment, or first through eleventh aspects thereof.

In a thirteenth aspect of the second embodiment:
$R^1$ hydrogen, methyl, or ethyl; and
$R^2$ is selected from the group consisting of methyl, ethyl, n-propyl, isopropyl, n-butyl, 2,2-dimethylpropyl, t-butyl, isobutyl, n-pentyl, $(C_4-C_6)$cycloalkyl, $(C_3-C_5)$cycloalkylmethyl, methoxyethyl, and 2-fluoroethyl; or
$R^1$ and $R^2$ taken together with the nitrogen atom to which they are bonded form a ring selected from the group consisting of azetidinyl, pyrrolidinyl, piperidinyl, tetrazolyl, or octahydrocyclopenta[c]pyrrolyl, and wherein the ring formed by $R^1$ and $R^2$ taken together with the nitrogen atom to which they are bonded is optionally substituted with fluoro. Values and alternative values for the remaining variables are as defined in the first embodiment, or any aspect thereof, or the second embodiment, or first through twelfth aspects thereof.

In a fourteenth aspect of the second embodiment, $R^F$ is hydrogen. Values and alternative values for the remaining variables are as defined in the first embodiment, or any aspect thereof, or the second embodiment, or first through thirteenth aspects thereof.

A third embodiment is a compound represented by Structural Formula X:

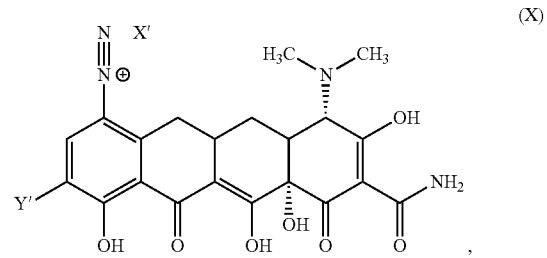

or a salt, solvate or combination thereof, wherein:

X' is $BF_4^-$, $PF_6^-$, $AsF_6^-$ or $HSiF_6^-$;

Y' is selected from the group consisting of halo, nitro, —$N(R^A)(R^B)$, —$N(R^F)$—C(O)—[C(R^D)(R^E)]_{1-4}$—N$(R^A)(R^B)$, —$N(R^F)$—C(O)—N(R^A)(R^B)$, —$N(R^F)$—C(O)—($C_1$-$C_6$)alkyl, —$N(R^F)$—C(O)—OR^A$, —$N(R^F)$—C(O)-heterocyclyl, —$N(R^F)$—C(O)-heteroaryl, —$N(R^F)$—C(O)-carbocyclyl, —$N(R^F)$—C(O)-aryl, —$N(R^F)$—S(O)$_m$—($C_1$-$C_4$)alkylene-N(R^A)(R^B)$, —$N(R^F)$—S(O)$_m$—($C_1$-$C_4$)alkylene-carbocyclyl, and —$N(R^F)$—S(O)$_m$—($C_1$-$C_4$)alkylene-aryl (e.g., —$N(R^A)(R^B)$, —$N(R^F)$—C(O)—[C(R^D)(R^E)]_{1-4}$—N(R^A)(R^B)$, —$N(R^F)$—C(O)—N(R^A)(R^B)$, —$N(R^F)$—C(O)—($C_1$-$C_6$)alkyl, —$N(R^F)$—C(O)—OR^A$. —$N(R^F)$—C(O)-heterocyclyl, —$N(R^F)$—C(O)-heteroaryl, —$N(R^F)$—C(O)-carbocyclyl, —$N(R^F)$—C(O)-aryl, —$N(R^F)$—S(O)$_m$—($C_1$-$C_4$)alkylene-N(R^A)(R^B)$, —$N(R^F)$—S(O)$_m$—($C_1$-$C_4$)alkylene-carbocyclyl, and —$N(R^F)$—S(O)$_m$—($C_1$-$C_4$)alkylene-aryl);

each $R^A$ and $R^B$ are independently selected from the group consisting of hydrogen, ($C_1$-$C_7$)alkyl, —O—($C_1$-$C_7$)alkyl, —($C_0$-$C_6$)alkylene-carbocyclyl, —($C_0$-$C_6$)alkylene-aryl, —($C_0$-$C_6$)alkylene-heterocyclyl, —($C_0$-$C_6$)alkylene-heteroaryl, —($C_1$-$C_6$)alkylene-O—($C_1$-$C_7$)alkyl, —($C_1$-$C_6$)alkylene-O-carbocyclyl, —($C_1$-$C_6$)alkylene-O-aryl, —($C_1$-$C_6$)alkylene-O-heterocyclyl, —($C_1$-$C_6$)alkylene-O-heteroaryl, —S(O)$_m$—($C_1$-$C_6$)alkyl, —($C_0$-$C_4$)alkylene-S(O)$_m$-carbocyclyl, —($C_0$-$C_4$)alkylene-S(O)$_m$-aryl, —($C_0$-$C_4$)alkylene-S(O)$_m$-heterocyclyl and —($C_0$-$C_4$)alkylene-S(O)$_m$-heteroaryl; or $R^A$ and $R^B$ taken together with the nitrogen atom to which they are bound form a heterocyclyl or heteroaryl, wherein the heterocycle or heteroaryl optionally comprises 1 to 4 additional heteroatoms independently selected from the group consisting of N, S and O;

$R^D$ and $R^E$ are each independently selected from the group consisting of hydrogen, ($C_1$-$C_6$)alkyl, carbocyclyl, aryl, heterocyclyl or heteroaryl; or $R^D$ and $R^E$ taken together with the carbon atom to which they are bound form a 3-7 membered carbocyclyl or a 4-7 membered heterocyclyl, wherein the heterocyclyl formed by $R^D$ and $R^E$ optionally comprises one or two additional heteroatoms independently selected from the group consisting of N, S and O;

$R^F$ is selected from the group consisting of hydrogen, ($C_1$-$C_7$)alkyl, carbocyclyl, aryl and heteroaryl; and m is 0, 1 or 2, wherein:

each carbocyclyl, aryl, heterocyclyl or heteroaryl is optionally and independently substituted with one or more substituents independently selected from the group consisting of halo, —($C_1$-$C_4$)alkyl, —OH, =O, —O—($C_1$-$C_4$)alkyl, —($C_1$-$C_4$)alkylene-O—($C_1$-$C_4$)alkyl, halo-substituted —($C_1$-$C_4$)alkyl, halo-substituted —O—($C_1$-$C_4$)alkyl, —C(O)—($C_1$-$C_4$)alkyl, —C(O)-(fluoro-substituted-($C_1$-$C_4$)alkyl), —S(O)$_m$—($C_1$-$C_4$)alkyl, —N(R^G)(R^G)$, and CN; and each alkyl in the group represented by $R^A$, $R^B$, $R^D$ and $R^E$ is optionally and independently substituted with one or more substituents independently selected from the group consisting of halo, —($C_1$-$C_4$)alkyl, —OH, —O—($C_1$-$C_7$)alkyl, —($C_1$-$C_4$)alkylene-O—($C_1$-$C_4$)alkyl, fluoro-substituted-($C_1$-$C_4$)alkyl, —S(O)$_m$—($C_1$-$C_4$)alkyl, and —N(R^G)(R^G)$, wherein each $R^G$ is hydrogen or ($C_1$-$C_4$)alkyl, wherein each alkyl in the group represented by $R^G$ is optionally and independently substituted with one or more substituents independently selected from the group consisting of —($C_1$-$C_4$)alkyl, ($C_3$-$C_6$)cycloalkyl, halo, —OH, —O—($C_1$-$C_4$)alkyl, and ($C_1$-$C_4$)alkyl-O—($C_1$-$C_4$)alkyl.

In a first aspect of the third embodiment, X' is $BF_4^-$. Values and alternative values for the remaining variables are as defined in the third embodiment.

In a second aspect of the third embodiment, the compound is represented by Structural Formula (Xa):

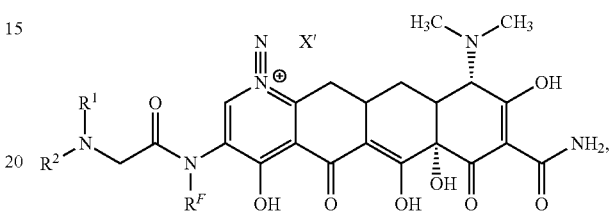

or a salt, solvate or combination thereof, wherein:

X' is $BF_4^-$, $PF_6^-$, $AsF_6^-$ or $HSiF_6^-$;

$R^1$ and $R^2$ are each independently selected from the group consisting of hydrogen, ($C_1$-$C_7$)alkyl, ($C_3$-$C_6$)cycloalkyl($C_1$-$C_4$)alkyl, ($C_1$-$C_7$)alkoxy($C_1$-$C_4$)alkyl, ($C_3$-$C_6$)cycloalkoxy($C_1$-$C_4$)alkyl, ($C_3$-$C_6$)cycloalkyl, aryl, aryl($C_1$-$C_4$)alkyl, aryloxy($C_1$-$C_4$)alkyl, arylthio($C_1$-$C_4$)alkyl, arylsufinyl($C_1$-$C_4$)alkyl, arylsulfonyl($C_1$-$C_4$)alkyl, and —O—($C_1$-$C_7$)alkyl; or $R^1$ and $R^2$ taken together with the nitrogen atom to which they are bonded form a monocyclic or bicyclic heteroaryl, or a monocyclic, fused bicyclic, bridged bicyclic or spiro bicyclic heterocycle, wherein the heteroaryl or heterocycle optionally contains one or two additional heteroatoms independently selected from the group consisting of N, O and S, wherein each alkyl, cycloalkyl, alkoxy and cycloalkoxy moiety in the groups represented by $R^1$ and $R^2$ and each heterocycle represented by $NR^1R^2$ taken together is optionally substituted with one or more substituents independently selected from the group consisting of ($C_1$-$C_4$)alkyl, halo, —OH, ($C_1$-$C_4$)alkoxy, ($C_1$-$C_4$)alkylthio, ($C_1$-$C_4$)alkylsulfinyl, ($C_1$-$C_4$)alkylsulfonyl, ($C_1$-$C_4$)alkoxy($C_1$-$C_4$)alkyl, and —N(R^3)(R^4)$; and each aryl, aryloxy, arylthio, arylsufinyl and arylsulfonyl moiety in the groups represented by $R^1$ and $R^2$ and each heteroaryl represented by $NR^1R^2$ taken together is optionally substituted with one or more substituents independently selected from the group consisting of ($C_1$-$C_4$)alkyl, halo, —OH, ($C_1$-$C_4$)alkoxy, —S—($C_1$-$C_4$)alkyl, —S(O)($C_1$-$C_4$)alkyl, —S(O)$_2$($C_1$-$C_4$)alkyl, ($C_1$-$C_4$)alkoxy($C_1$-$C_4$)alkyl, —N(R^3)(R^4)$; —CN, halo($C_1$-$C_4$)alkyl, and halo($C_1$-$C_4$)alkoxy; and $R^3$ and $R^4$ are each independently selected from the group consisting of —H and ($C_1$-$C_4$)alkyl, wherein the ($C_1$-$C_4$)alkyl represented by $R^3$ and $R^4$ is optionally substituted with one or more substituents independently selected from the group consisting of ($C_1$-$C_4$)alkyl, halo, —OH, ($C_1$-$C_4$)alkoxy, and ($C_1$-$C_4$)alkoxy($C_1$-$C_4$)alkyl. Values and alternative values for the variables are as defined in the second embodiment, or any aspect thereof, or the third embodiment, or first aspect thereof.

In a third aspect of the third embodiment, the compound is represented by Structural Formula Xb:

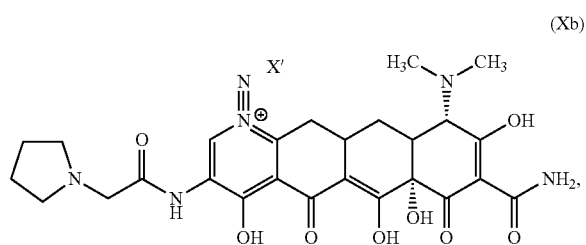

(Xb)

or a salt, solvate or combination thereof. Values and alternative values for the variables are as defined in the third embodiment, or first aspect thereof.

A fourth embodiment provides a compound represented by Structural Formula II:

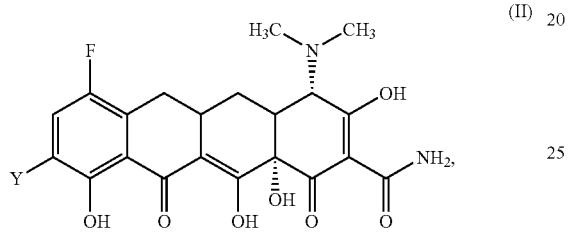

(II)

or a salt, solvate or combination thereof, wherein:

Y is selected from the group consisting of hydrogen, halo, nitro, —($C_1$-$C_7$)alkyl, carbocyclyl, —($C_1$-$C_4$)alkylene-N($R^A$)($R^B$), —($C_1$-$C_4$)alkylene-N($R^F$)—C(O)—[C($R^D$)($R^E$)]$_{0-4}$—N($R^A$)($R^B$), —CH=N—O$R^A$, —N($R^A$)($R^B$), —N($R^F$)—C(O)—[C($R^D$)($R^E$)]$_{1-4}$—N($R^A$)($R^B$), —N($R^F$)—C(O)—N($R^A$)($R^B$), —N($R^F$)—C(O)—($C_1$-$C_6$)alkyl, —N($R^F$)—C(O)—O$R^A$, —N($R^F$)—C(O)-heterocyclyl, —N($R^F$)—C(O)-heteroaryl, —N($R^F$)—C(O)-carbocyclyl, —N($R^F$)—C(O)-aryl, —N($R^F$)—S(O)$_m$—($C_1$-$C_4$)alkylene-N($R^A$)($R^B$), —N($R^F$)—S(O)$_m$—($C_1$-$C_4$)alkylene-carbocyclyl, and —N($R^F$)—S(O)$_m$—($C_1$-$C_4$)alkylene-aryl (e.g., hydrogen, —($C_1$-$C_7$)alkyl, carbocyclyl, —($C_1$-$C_4$)alkylene-N($R^A$)($R^B$), —($C_1$-$C_4$)alkylene-N($R^F$)—C(O)—[C($R^D$)($R^E$)]$_{0-4}$—N($R^A$)($R^B$), —CH=N—O$R^A$, —N($R^A$)($R^B$), —N($R^F$)—C(O)—[C($R^D$)($R^E$)]$_{1-4}$—N($R^A$)($R^B$), —N($R^F$)—C(O)—N($R^A$)($R^B$), —N($R^F$)—C(O)—($C_1$-$C_6$)alkyl, —N($R^F$)—C(O)—O$R^A$, —N($R^F$)—C(O)-heterocyclyl, —N($R^F$)—C(O)-heteroaryl, —N($R^F$)—C(O)-carbocyclyl, —N($R^F$)—C(O)-aryl, —N($R^F$)—S(O)$_m$—($C_1$-$C_4$)alkylene-N($R^A$)($R^B$), —N($R^F$)—S(O)$_m$—($C_1$-$C_4$)alkylene-carbocyclyl, and —N($R^F$)—S(O)$_m$—($C_1$-$C_4$)alkylene-aryl) wherein:

each $R^A$ and $R^B$ are independently selected from the group consisting of hydrogen, ($C_1$-$C_7$)alkyl, —O—($C_1$-$C_7$)alkyl, —($C_0$-$C_6$)alkylene-carbocyclyl, —($C_0$-$C_6$)alkylene-aryl, —($C_0$-$C_6$)alkylene-heterocyclyl, —($C_0$-$C_6$)alkylene-heteroaryl, —($C_1$-$C_6$)alkylene-O—($C_1$-$C_7$)alkyl, —($C_1$-$C_6$)alkylene-O-carbocyclyl, —($C_1$-$C_6$)alkylene-O-aryl, —($C_1$-$C_6$)alkylene-O-heterocyclyl, —($C_1$-$C_6$)alkylene-O-heteroaryl, —S(O)$_m$—($C_1$-$C_6$)alkyl, —($C_0$-$C_4$)alkylene-S(O)$_m$-carbocyclyl, —($C_0$-$C_4$)alkylene-S(O)$_m$-aryl, —($C_0$-$C_4$)alkylene-S(O)$_m$-heterocyclyl and —($C_0$-$C_4$)alkylene-S(O)$_m$-heteroaryl; or $R^A$ and $R^B$ taken together with the nitrogen atom to which they are bound form a heterocyclyl or heteroaryl, wherein the heterocycle or heteroaryl optionally comprises 1 to 4 additional heteroatoms independently selected from the group consisting of N, S and O;

each $R^D$ and each $R^E$ is independently selected from the group consisting of hydrogen, ($C_1$-$C_6$)alkyl, carbocyclyl, aryl, heterocyclyl or heteroaryl, or $R^D$ and $R^E$ taken together with the carbon atom to which they are bound form a 3-7 membered carbocyclyl, or a 4-7 membered heterocyclyl, wherein the heterocyclyl formed by $R^D$ and $R^E$ optionally comprises one to two additional heteroatoms independently selected from the group consisting of N, S and O;

$R^F$ is selected from the group consisting of hydrogen, ($C_1$-$C_7$)alkyl, carbocyclyl, aryl and heteroaryl; and m is 0, 1 or 2, wherein:

each carbocyclyl, aryl, heterocyclyl or heteroaryl is optionally and independently substituted with one or more substituents independently selected from the group consisting of halo, —($C_1$-$C_4$)alkyl, —OH, =O, —O—($C_1$-$C_4$)alkyl, —($C_1$-$C_4$)alkylene-O—($C_1$-$C_4$)alkyl, halo-substituted —($C_1$-$C_4$)alkyl, halo-substituted —O—($C_1$-$C_4$)alkyl, —C(O)—($C_1$-$C_4$)alkyl, —C(O)-(fluoro-substituted-($C_1$-$C_4$)alkyl), —S(O)$_m$—($C_1$-$C_4$)alkyl, —N($R^G$)($R^G$), and CN;

each alkyl in the group represented by $R^A$, $R^B$, $R^D$ and $R^E$ is optionally and independently substituted with one or more substituents independently selected from the group consisting of halo, —($C_1$-$C_4$)alkyl, —OH, —O—($C_1$-$C_7$)alkyl, —($C_1$-$C_4$)alkylene-O—($C_1$-$C_4$)alkyl, fluoro-substituted-($C_1$-$C_4$)alkyl, —S(O)$_m$—($C_1$-$C_4$)alkyl, and —N($R^G$)($R^G$), wherein each $R^G$ is hydrogen or ($C_1$-$C_4$)alkyl, wherein each alkyl in the group represented by $R^G$ is optionally and independently substituted with one or more substituents independently selected from the group consisting of —($C_1$-$C_4$)alkyl, ($C_3$-$C_6$)cycloalkyl, halo, —OH, —O—($C_1$-$C_4$)alkyl, and ($C_1$-$C_4$)alkyl-O—($C_1$-$C_4$)alkyl. Alternative values for the variables in Structural Formula II are as described in the first or second embodiment, or any aspect of the foregoing.

In a first aspect of the fourth embodiment, the compound is represented by Structural Formula IIa:

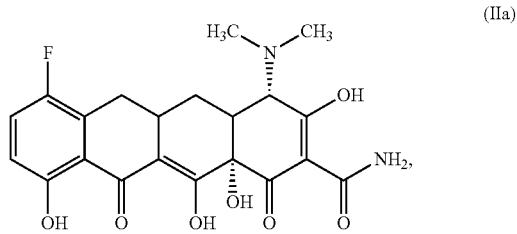 [SMILES: CN(C)[C@@H]1C(O)=C(C(N)=O)C(=O)[C@@]2(O)C(O)=C3C(=O)c4c(O)ccc(F)c4CC3CC12]

(IIa)

or a salt, solvate or combination thereof.

A fifth embodiment provides a compound of Structural Formula III:

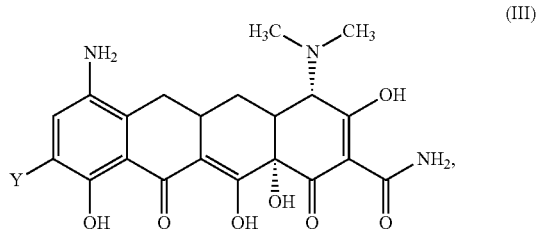

(III)

or a salt, solvate or combination thereof, wherein values and alternative values for Y are as described in the first, second or fourth embodiment, or any aspect of the foregoing.

In a first aspect of the fifth embodiment, Y is selected from the group consisting of hydrogen, halo, nitro, —($C_1$-$C_7$)alkyl, carbocyclyl, —($C_1$-$C_4$)alkylene-N($R^A$)($R^B$), —($C_1$-$C_4$)alkylene-N($R^F$)—C(O)—[C($R^D$)($R^E$)]$_{1-4}$—N($R^A$)($R^B$), —CH=N—O$R^A$, —N($R^A$)($R^B$), —N($R^F$)—C(O)—[C($R^D$)($R^E$)]$_{1-4}$—N($R^A$)($R^B$), —N($R^F$)—C(O)—N($R^A$)($R^B$), —N($R^F$)—C(O)—($C_1$-$C_4$)alkyl, —N($R^F$)—C(O)—O$R^A$, —N($R^F$)—C(O)-heterocyclyl, —N($R^F$)—C(O)-heteroaryl, —N($R^F$)—C(O)-carbocyclyl, —N($R^F$)—C(O)-aryl, —N($R^F$)—S(O)$_m$—($C_1$-$C_4$)alkylene-N($R^A$)($R^B$), —N($R^F$)—S(O)$_m$—($C_1$-$C_4$)alkylene-carbocyclyl, and —N($R^F$)—S(O)$_m$—($C_1$-$C_4$)alkylene-aryl, preferably, hydrogen, —($C_1$-$C_7$)alkyl, carbocyclyl, —($C_1$-$C_4$)alkylene-N($R^A$)($R^B$). —($C_1$-$C_4$)alkylene-N($R^F$)—C(O)—[C($R^D$)($R^E$)]$_{0-4}$—N($R^A$)($R^B$), —CH=N—O$R^A$, —N($R^A$)($R^B$), —N($R^F$)—C(O)—[C($R^D$)($R^E$)]$_{1-4}$—N($R^A$)($R^B$), —N($R^F$)—C(O)—N($R^A$)($R^B$), —N($R^F$)—C(O)—($C_1$-$C_6$)alkyl, —N($R^F$)—C(O)—O$R^A$, —N($R^F$)—C(O)-heterocyclyl, —N($R^F$)—C(O)-heteroaryl, —N($R^F$)—C(O)-carbocyclyl, —N($R^F$)—C(O)-aryl, —N($R^F$)—S(O)$_m$—($C_1$-$C_4$)alkylene-N($R^A$)($R^B$), —N($R^F$)—S(O)$_m$—($C_1$-$C_4$)alkylene-carbocyclyl, and —N($R^F$)—S(O)$_m$—($C_1$-$C_4$)alkylene-aryl, wherein at least one of $R^A$ and $R^B$ is not hydrogen when Y is —($C_1$-$C_4$)alkylene-N($R^A$)($R^B$), —($C_1$-$C_4$)alkylene-N($R^F$)—C(O)—[C($R^D$)($R^E$)]$_{1-4}$—N($R^A$)($R^B$), —N($R^A$)($R^B$), —N($R^F$)—C(O)—[C($R^D$)($R^E$)]$_{1-4}$—N($R^A$)($R^B$), or —N($R^F$)—S(O)$_m$—($C_1$-$C_4$)alkylene-N($R^A$)($R^B$). Values for the remaining variables are as described in the first, second or fourth embodiment, or any aspect of the foregoing, or the fifth embodiment.

A sixth embodiment provides a compound of Structural Formula XI:

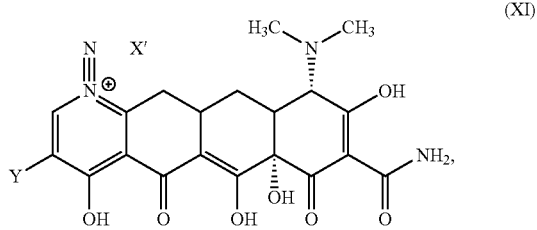

(XI)

or a salt, solvate or combination thereof, wherein X' is $BF_4^-$, $PF_6^-$, $AsF_6^-$ or $HSiF_6^-$; and values and alternative values for Y are as described in the first, second or fourth embodiment, or any aspect of the foregoing. Alternative values for X' are as described in the third embodiment, or any aspect thereof.

In a first aspect of the sixth embodiment, the compound is represented by Structural Formula XIa:

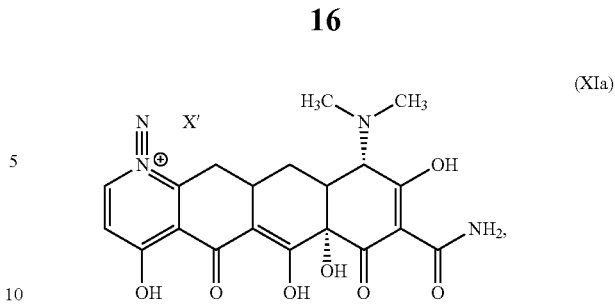

(XIa)

or a salt, solvate or combination thereof. Values and alternative values for X' are as described in the third embodiment, or any aspect thereof, or the sixth embodiment.

A seventh embodiment provides a compound of Structural Formula XII:

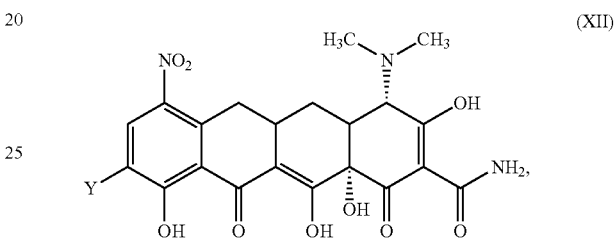

(XII)

or a salt, solvate or combination thereof, wherein values and alternative values for Y are as described in the first, second or fourth embodiment, or any aspect of the foregoing.

In a first aspect of the seventh embodiment, Y is selected from the group consisting of hydrogen, halo, —($C_1$-$C_7$)alkyl, carbocyclyl, —($C_1$-$C_4$)alkylene-N($R^A$)($R^B$), —($C_1$-$C_4$)alkylene-N($R^F$)—C(O)—[C($R^D$)($R^E$)]$_{0-4}$—N($R^A$)($R^B$), —CH=N—O$R^A$, —N($R^A$)($R^B$), —N($R^F$)—C(O)—[C($R^D$)($R^E$)]$_{1-4}$—N($R^A$)($R^B$), —N($R^F$)—C(O)—N($R^A$)($R^B$), —N($R^F$)—C(O)—($C_1$-$C_6$)alkyl, —N($R^F$)—C(O)—O$R^A$, —N($R^F$)—C(O)-heterocyclyl, —N($R^F$)—C(O)-heteroaryl, —N($R^F$)—C(O)-carbocyclyl, —N($R^F$)—C(O)-aryl, —N($R^F$)—S(O)$_m$—($C_1$-$C_4$)alkylene-N($R^A$)($R^B$), —N($R^F$)—S(O)$_m$—($C_1$-$C_4$)alkylene-carbocyclyl, and —N($R^F$)—S(O)$_m$—($C_1$-$C_4$)alkylene-aryl (e.g., hydrogen, —($C_1$-$C_7$)alkyl, carbocyclyl, —($C_1$-$C_4$)alkylene-N($R^A$)($R^B$), —($C_1$-$C_4$)alkylene-N($R^F$)—C(O)—[C($R^D$)($R^E$)]$_{0-4}$—N($R^A$)($R^B$), —CH=N—O$R^A$, —N($R^A$)($R^B$), —N($R^F$)—C(O)—[C($R^D$)($R^E$)]$_{1-4}$—N($R^A$)($R^B$), —N($R^F$)—C(O)—N($R^A$)($R^B$), —N($R^F$)—C(O)—($C_1$-$C_6$)alkyl, —N($R^F$)—C(O)—O$R^A$, —N($R^F$)—C(O)-heterocyclyl, —N($R^F$)—C(O)-heteroaryl, —N($R^F$)—C(O)-carbocyclyl, —N($R^F$)—C(O)-aryl, —N($R^F$)—S(O)$_m$—($C_1$-$C_4$)alkylene-N($R^A$)($R^B$), —N($R^F$)—S(O)$_m$—($C_1$-$C_4$)alkylene-carbocyclyl, and —N($R^F$)—S(O)$_m$—($C_1$-$C_4$)alkylene-aryl)), wherein Y is not nitro and at least one of $R^A$ and $R^B$ is not hydrogen when Y is —($C_1$-$C_4$)alkylene-N($R^A$)($R^B$), —($C_1$-$C_4$)alkylene-N($R^F$)—C(O)—[C($R^D$)($R^E$)]$_{1-4}$—N($R^A$)($R^B$), —N($R^A$)($R^B$), —N($R^F$)—C(O)—[C($R^D$)($R^E$)]$_{1-4}$—N($R^A$)($R^B$), or —N($R^F$)—S(O)$_m$—($C_1$-$C_4$)alkylene-N($R^A$)($R^B$). Values for the remaining variables are as described in the first, second or fourth embodiment, or any aspect of the foregoing, or the seventh embodiment.

An eighth embodiment provides a compound of Structural Formula VI:

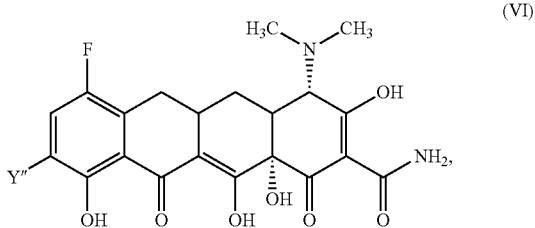

(VI)

or a salt, solvate or combination thereof, wherein:
Y" is selected from the group consisting of —N(R$^A$)(R$^B$), —N(R$^F$)—C(O)—[C(R$^D$)(R$^E$)]$_{1-4}$—N(R$^A$)(R$^B$), —N(R$^F$)—C(O)—N(R$^A$)(R$^B$), —N(R$^F$)—C(O)—(C$_1$-C$_6$)alkyl, —N(R$^F$)—C(O)-heterocyclyl, —N(R$^F$)—C(O)-heteroaryl, —N(R$^F$)—C(O)-carbocyclyl, —N(R$^F$)—C(O)-aryl, —N(R$^F$)—S(O)$_m$—(C$_1$-C$_4$)alkylene-N(R$^A$)(R$^B$), —N(R$^F$)—S(O)$_m$—(C$_1$-C$_4$)alkylene-carbocyclyl, and —N(R$^F$)—S(O)$_m$—(C$_1$-C$_4$)alkylene-aryl, wherein:
at least one of R$^A$ and R$^B$ is not hydrogen when Y" is —N(R$^A$)(R$^B$);
each R$^A$ and R$^B$ are independently selected from the group consisting of hydrogen, (C$_1$-C$_7$)alkyl, —O—(C$_1$-C$_7$)alkyl, —(C$_0$-C$_6$)alkylene-carbocyclyl, —(C$_0$-C$_6$)alkylene-aryl, —(C$_0$-C$_6$)alkylene-heterocyclyl, —(C$_0$-C$_6$)alkylene-heteroaryl, —(C$_1$-C$_6$)alkylene-O—(C$_1$-C$_7$)alkyl, —(C$_1$-C$_6$)alkylene-O-carbocyclyl, —(C$_1$-C$_6$)alkylene-O-aryl, —(C$_1$-C$_6$)alkylene-O-heterocyclyl, —(C$_1$-C$_6$)alkylene-O-heteroaryl, —S(O)$_m$—(C$_1$-C$_6$)alkyl, —(C$_0$-C$_4$)alkylene-S(O)$_m$-carbocyclyl, —(C$_0$-C$_4$)alkylene-S(O)$_m$-aryl, —(C$_0$-C$_4$)alkylene-S(O)$_m$-heterocyclyl and —(C$_0$-C$_4$)alkylene-S(O)$_m$-heteroaryl; or
R$^A$ and R$^B$ taken together with the nitrogen atom to which they are bound form a heterocyclyl or heteroaryl, wherein the heterocycle or heteroaryl optionally comprises 1 to 4 additional heteroatoms independently selected from the group consisting of N, S and O;
each R$^D$ and each R$^E$ is independently selected from the group consisting of hydrogen, (C$_1$-C$_6$)alkyl, carbocyclyl, aryl, heterocyclyl or heteroaryl, or
R$^D$ and R$^E$ taken together with the carbon atom to which they are bound form a 3-7 membered carbocyclyl, or a 4-7 membered heterocyclyl, wherein the heterocyclyl formed by R$^D$ and R$^E$ optionally comprises one to two additional heteroatoms independently selected from the group consisting of N, S and O;
R$^F$ is selected from the group consisting of hydrogen, (C$_1$-C$_7$)alkyl, carbocyclyl, aryl and heteroaryl; and
m is 0, 1 or 2, wherein:
each carbocyclyl, aryl, heterocyclyl or heteroaryl is optionally and independently substituted with one or more substituents independently selected from the group consisting of halo, —(C$_1$-C$_4$)alkyl, —OH, =O, —O—(C$_1$-C$_4$)alkyl, —(C$_1$-C$_4$)alkylene-O—(C$_1$-C$_4$)alkyl, halo-substituted —(C$_1$-C$_4$)alkyl, halo-substituted —O—(C$_1$-C$_4$)alkyl, —C(O)—(C$_1$-C$_4$)alkyl, —C(O)-(fluoro-substituted-(C$_1$-C$_4$)alkyl), —S(O)$_m$—(C$_1$-C$_4$)alkyl, —N(R$^G$)(R$^G$), and CN;
each alkyl in the group represented by R$^A$, R$^B$, R$^D$ and R$^E$ is optionally and independently substituted with one or more substituents independently selected from the group consisting of halo, —(C$_1$-C$_4$)alkyl, —OH, —O—(C$_1$-C$_7$)alkyl, —(C$_1$-C$_4$)alkylene-O—(C$_1$-C$_4$)alkyl, fluoro-substituted-(C$_1$-C$_4$)alkyl, —S(O)$_m$—(C$_1$-C$_4$)alkyl, and —N(R$^G$)(R$^G$), wherein
each R$^G$ is hydrogen or (C$_1$-C$_4$)alkyl, wherein each alkyl in the group represented by R$^G$ is optionally and independently substituted with one or more substituents independently selected from the group consisting of —(C$_1$-C$_4$)alkyl, (C$_3$-C$_6$)cycloalkyl, halo, —OH, —O—(C$_1$-C$_4$)alkyl, and (C$_1$-C$_4$)alkyl-O—(C$_1$-C$_4$)alkyl. Alternative values for the variables are as defined in the first embodiment, or any aspect thereof.

In a first aspect of the eighth embodiment:
Y" is —N(R$^F$)—C(O)—CH$_2$—N(R$^1$)(R$^2$), wherein:
R$^1$ and R$^2$ are each independently selected from the group consisting of hydrogen, (C$_1$-C$_7$)alkyl, (C$_3$-C$_6$)cycloalkyl(C$_1$-C$_4$)alkyl, (C$_1$-C$_7$)alkoxy(C$_1$-C$_4$)alkyl, (C$_3$-C$_6$)cycloalkoxy(C$_1$-C$_4$)alkyl, (C$_3$-C$_6$)cycloalkyl, aryl, aryl(C$_1$-C$_4$)alkyl, aryloxy(C$_1$-C$_4$)alkyl, arylthio(C$_1$-C$_4$)alkyl, arylsufinyl(C$_1$-C$_4$)alkyl, arylsulfonyl(C$_1$-C$_4$)alkyl, and —O—(C$_1$-C$_7$)alkyl; or
R$^1$ and R$^2$ taken together with the nitrogen atom to which they are bonded form a monocyclic or bicyclic heteroaryl, or a monocyclic, fused bicyclic, bridged bicyclic or spiro bicyclic heterocycle, wherein the heteroaryl or heterocycle optionally contains one or two additional heteroatoms independently selected from the group consisting of N, O and S, wherein
each alkyl, cycloalkyl, alkoxy and cycloalkoxy moiety in the groups represented by R$^1$ and R$^2$ and each heterocycle represented by NR$^1$R$^2$ taken together is optionally substituted with one or more substituents independently selected from the group consisting of the group consisting of (C$_1$-C$_4$)alkyl, halo, —OH, (C$_1$-C$_4$)alkoxy, (C$_1$-C$_4$)alkylthio, (C$_1$-C$_4$)alkylsulfinyl, (C$_1$-C$_4$)alkylsulfonyl, (C$_1$-C$_4$)alkoxy(C$_1$-C$_4$)alkyl, and —N(R$^3$)(R$^4$); and
each aryl, aryloxy, arylthio, arylsufinyl and arylsulfonyl moiety in the groups represented by R$^1$ and R$^2$ and each heteroaryl represented by NR$^1$R$^2$ taken together is optionally substituted with one or more substituents independently selected from the group consisting of (C$_1$-C$_4$)alkyl, halo, —OH, (C$_1$-C$_4$)alkoxy, —S—(C$_1$-C$_4$)alkyl, —S(O)(C$_1$-C$_4$)alkyl, —S(O)$_2$(C$_1$-C$_4$)alkyl, (C$_1$-C$_4$)alkoxy(C$_1$-C$_4$)alkyl, —N(R$^3$)(R$^4$); —CN, halo(C$_1$-C$_4$)alkyl, and halo(C$_1$-C$_4$)alkoxy; and
R$^3$ and R$^4$ are each independently selected from the group consisting of —H and (C$_1$-C$_4$)alkyl, wherein the (C$_1$-C$_4$)alkyl represented by R$^3$ and R$^4$ is optionally substituted with one or more substituents independently selected from the group consisting of (C$_1$-C$_4$)alkyl, halo, —OH, (C$_1$-C$_4$)alkoxy, and (C$_1$-C$_4$)alkoxy(C$_1$-C$_4$)alkyl. Alternative values for the variables are as defined in the second embodiment, or any aspect of the foregoing.

A ninth embodiment provides a compound of Structural Formula VII:

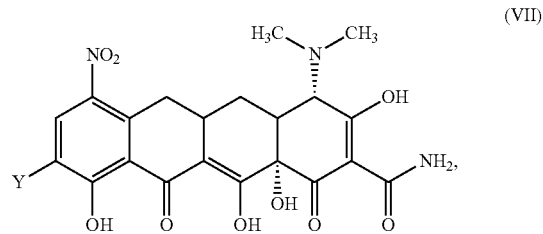

(VII)

or a salt, solvate or combination thereof, wherein values and alternative values for Y are as described in the first, second or fourth embodiment, or any aspect of the foregoing.

In a first aspect of the ninth embodiment. Y is selected from the group consisting of —N($R^A$)($R^B$), —N($R^F$)—C(O)—[C($R^D$)($R^E$)]$_{1-4}$—N($R^A$)($R^B$), —N($R^F$)—C(O)—N($R^A$)($R^B$), —N($R^F$)—C(O)—($C_1$-$C_6$)alkyl, —N($R^F$)—C(O)-heterocyclyl, —N($R^F$)—C(O)-heteroaryl, —N($R^F$)—C(O)-carbocyclyl, —N($R^F$)—C(O)-aryl, —N($R^F$)—S(O)$_m$—($C_1$-$C_4$)alkylene-N($R^A$)($R^B$), —N($R^F$)—S(O)$_m$—($C_1$-$C_4$)alkylene-carbocyclyl, and —N($R^F$)—S(O)$_m$—($C_1$-$C_4$)alkylene-aryl, wherein at least one of $R^A$ and $R^B$ is not hydrogen when Y is —N($R^A$)($R^B$), —N($R^F$)—C(O)—[C($R^D$)($R^E$)]$_{1-4}$—N($R^A$)($R^B$) or —N($R^F$)—S(O)$_m$—($C_1$-$C_4$)alkylene-N($R^A$)($R^B$). Values for the remaining variables are as defined in the first, second or fourth embodiment, or any aspect of the foregoing, or the ninth embodiment.

"Alkyl" means a saturated aliphatic branched or straight-chain monovalent hydrocarbon radical having the specified number of carbon atoms. Thus. "($C_1$-$C_7$)alkyl" means a radical having from 1-7 carbon atoms in a linear or branched arrangement. "($C_1$-$C_7$)alkyl" includes methyl, ethyl, propyl, butyl, pentyl, hexyl and heptyl. Suitable substitutions for a "substituted alkyl" include, but are not limited to, -halogen, —OH, ($C_1$-$C_4$)alkyl, ($C_1$-$C_4$)alkoxy, ($C_1$-$C_4$)alkylthio, ($C_1$-$C_4$)alkylsulfinyl, ($C_1$-$C_4$)alkylsulfonyl, ($C_1$-$C_4$)alkoxy($C_1$-$C_4$)alkyl, and —N($R^3$)($R^4$), wherein $R^3$ and $R^4$ are as described above.

"Alkylene" means a saturated aliphatic branched or straight-chain divalent hydrocarbon radical having the specified number of carbon atoms. Thus. "($C_1$-$C_4$)alkylene" means a diradical having from 1-4 carbon atoms in a linear or branched arrangement. "($C_1$-$C_4$)alkylene" includes methylene, ethylene, propylene and butylene.

"Cycloalkyl" means a saturated aliphatic cyclic hydrocarbon radical having the specified number of carbon atoms, ($C_3$-$C_6$)cycloalkyl includes cyclopropyl, cyclobutyl, cyclopentyl, and cyclohexyl. Suitable substituents for a "substituted cycloalkyl" include halogen, —OH, ($C_1$-$C_4$)alkyl, ($C_1$-$C_4$)alkoxy, ($C_1$-$C_4$)alkylthio, ($C_1$-$C_4$)alkylsulfinyl, ($C_1$-$C_4$)alkylsulfonyl, ($C_1$-$C_4$)alkoxy($C_1$-$C_4$)alkyl, and —N($R^3$)($R^4$), wherein $R^3$ and $R^4$ are as described above.

"Heterocycle" or "heterocyclyl" means a 4-12 membered partially unsaturated or saturated heterocyclic ring containing 1, 2, or 3 heteroatoms independently selected from N, O or S. When one heteroatom is S, it can be optionally mono- or di-oxygenated (i.e. —S(O)— or —S(O)$_2$—). The heterocycle can be monocyclic, fused bicyclic, bridged bicyclic, or spiro bicyclic.

Examples of monocyclic heterocycle include, but not limited to, azetidine, pyrrolidine, piperidine, piperazine, hexahydropyrimidine, tetrahydrofuran, tetrahydropyran, morpholine, thiomorpholine, thiomorpholine 1,1-dioxide, tetrahydro-2H-1,2-thiazine, tetrahydro-2H-1,2-thiazine 1,1-dioxide, isothiazolidine, isothiazolidine 1,1-dioxide.

A fused bicyclic heterocycle has two rings which have two adjacent ring atoms in common. The first ring is a monocyclic heterocycle and the second ring is a cycloalkyl, partially unsaturated carbocycle, phenyl, heteroaryl or a monocyclic heterocycle. For example, the second ring is a ($C_3$-$C_6$)cycloalkyl, such as cyclopropyl, cyclobutyl, cyclopentyl and cyclohexyl. Alternatively, the second ring is phenyl. Example of fused bicyclic heterocycles includes, but not limited to, indoline, isoindoline, 2,3-dihydro-1H-benzo[d]imidazole, 2,3-dihydrobenzo[d]oxazole, 2,3-dihydrobenzo[d]thiazole, octahydrobenzo[d]oxazole, octahydro-1H-benzo[d]imidazole, octahydrobenzo[d]thiazole, octahydrocyclopenta[c]pyrrole, 3-azabicyclo[3.1.0]hexane, and 3-azabicyclo[3.2.0]heptane.

A spiro bicyclic heterocycle has two rings which have only one ring atom in common. The first ring is a monocyclic heterocycle and the second ring is a cycloalkyl, partially unsaturated carbocycle or a monocyclic heterocycle. For example, the second ring is a ($C_3$-$C_6$)cycloalkyl. Example of spiro bicyclic heterocycle includes, but not limited to, azaspiro[4.4]nonane, 7-azaspiro[4.4]nonane, azaspiro[4.5]decane, 8-azaspiro[4.5]decane, azaspiro[5.5]undecane, 3-azaspiro[5.5]undecane and 3,9-diazaspiro[5.5]undecane.

A bridged bicyclic heterocycle has two rings which have three or more adjacent ring atoms in common. The first ring is a monocyclic heterocycle and the other ring is a cycloalkyl (such as ($C_1$-$C_6$)cycloalkyl), partially unsaturated carbocycle or a monocyclic heterocycle. Examples of bridged bicyclic heterocycles include, but are not limited to, azabicyclo[3.3.1]nonane, 3-azabicyclo[3.3.1]nonane, azabicyclo[3.2.1]octane, 3-azabicyclo[3.2.1]octane, 6-azabicyclo[3.2.1]octane and azabicyclo[2.2.2]octane, 2-azabicyclo[2.2.2]octane.

When the heterocycle contains a N atom other than the nitrogen atom to which $R^1$ and $R^2$ are bonded, the N atom can be substituted with H, alkyl, cycloalkyl, cycloalkylalkyl, aryl, arylalkyl, heteroaryl, heteroarylalkyl, each of which can be optionally substituted with halogen, hydroxy, alkoxy, haloalkyl, alkyl, etc. The heterocycle can be optionally substituted with an oxo group (C═O) and oxo substituted heterocyclic rings include, but are not limited to, thiomorpholine 1-oxide, thiomorpholine 1,1-dioxide, tetrahydro-2H-1,2-thiazine 1,1-dioxide, and isothiazolidine 1,1-dioxide, pyrrolidin-2-one, piperidin-2-one, piperazin-2-one, and morpholin-2-one. Other optional substituents for a heterocycle include ($C_1$-$C_4$)alkyl, halo, —OH, ($C_1$-$C_4$)alkoxy, ($C_1$-$C_4$)alkylthio, ($C_1$-$C_4$)alkylsulfinyl, ($C_1$-$C_4$)alkylsulfonyl, ($C_1$-$C_4$)alkoxy($C_1$-$C_4$)alkyl, —N($R^3$)($R^4$), —CN, halo($C_1$-$C_4$)alkyl, and halo($C_1$-$C_4$)alkoxy.

"Heteroaryl" means a 5-12 membered monovalent heteroaromatic monocyclic or bicyclic ring radical. A heteroaryl contains 1, 2 or 3 heteroatoms independently selected from N, O, and S. Heteroaryls include, but are not limited to pyrrole, imidazole, pyrazole, oxazole, isoxazole, thiazole, isothiazole, 1,2,3-triazole, 1,2,4-triazole, 1,3,4-oxadiazole, 1,2,5-thiadiazole, 1,2,5-thiadiazole 1-oxide, 1,2,5-thiadiazole 1,1-dioxide, 1,3,4-thiadiazole, pyridine, pyrazine, pyrimidine, pyridazine, 1,2,4-triazine, 1,3,5-triazine, and tetrazole. Bicyclic heteroaryl rings include, but are not limited to, bicyclo[4.4.0] and bicyclo[4.3.0] fused ring systems such as indolizine, indole, isoindole, indazole, benzimidazole, benzthiazole, purine, quinoline, isoquinoline, cinnoline, phthalazine, quinazoline, quinoxaline, 1,8-naphthyridine, and pteridine.

"Carbocycle" or "carbocyclyl" means 4-12 membered saturated or unsaturated aliphatic cyclic hydrocarbon ring.

"Alkoxy" means an alkyl radical attached through an oxygen linking atom. "Alkoxy" can also be depicted as —O-alkyl. For example, ($C_1$-$C_4$)-alkoxy can also depicted as —O—($C_1$-$C_4$)alkyl. "($C_1$-$C_4$)-alkoxy" includes methoxy, ethoxy, propoxy, and butoxy.

"Alkylthio" means an alkyl radical attached through a sulfur linking atom. "Alkylthio" can also be depicted as —S-alkyl. For example, "($C_1$-$C_4$)alkylthio" can be depicted as —S—($C_1$-$C_4$)alkyl. "($C_1$-$C_4$)alkylthio" include methylthio, ethylthio, propylthio and butylthio.

"Alkylsulfinyl" means an alkyl radical attached through a —S(O)— linking group. "Alkylsulfinyl" can be depicted as —S(O)-alkyl. For example, "($C_1$-$C_4$)alkylsulfinyl" can be depicted as —S(O)—(C$_1$-C$_4$)alkyl. "(C$_1$-C$_4$)alkylsulfinyl" include methylsulfinyl, ethylsulfinyl, propylsulfinyl and butylsulfinyl.

"Alkylsulfonyl" means an alkyl radical attached through a —S(O)$_2$— linking group. "Alkylsulfonyl" can be depicted as —S(O)$_2$-alkyl. For example, "(C$_1$-C$_4$)alkylsulfinyl" can be depicted as —S(O)$_2$—(C$_1$-C$_4$)alkyl. "(C$_1$-C$_4$)alkylsulfonyl" include methylsulfonyl, ethylsulfonyl, propylsulfonyl and butylsulfonyl.

"Haloalkyl" includes mono, poly, and perhaloalkyl groups where each halogen is independently selected from fluorine, chlorine, and bromine. Haloalkyl can also be referred as halo-substituted alkyl.

"Cycloalkoxy" means a cycloalkyl radical attached through an oxygen linking atom. "Cycloalkoxy" can also be depicted as —O-cycloalkyl. For example, "(C$_3$-C$_6$)cycloalkoxy" can be depicted as —O—(C$_3$-C$_6$)cycloalkyl. "(C$_3$-C$_6$)cycloalkoxy" includes cyclopropyloxy, cyclobutyloxy, cyclopentyloxy and cyclohexyloxy.

"Aryl" means an aromatic monocyclic or polycyclic (e.g., bicyclic or tricyclic) carbocyclic ring system. In one embodiment, "aryl" is a 6-12 membered monocyclic or bicyclic systems. Aryl systems include, but not limited to, phenyl, naphthalenyl, fluorenyl, indenyl, azulenyl, and anthracenyl.

"Aryloxy" means an aryl moiety attached through an oxygen linking atom. "Aryloxy" can be also depicted as —O-aryl. Aryloxy includes, but not limited to, phenoxy.

"Arylthio" means an aryl moiety attached through a sulfur linking atom. "Arylthio" can be also depicted as —S-aryl. Arylthio includes, but not limited to, phenylthio.

"Arylsulfinyl" means an aryl moiety attached through a —S(O)— linking group. "Arylsulfinyl" can be also depicted as —S(O)-aryl. Arylsulfinyl includes, but not limited to, phenylsulfinyl.

"Arylsulfonyl" means an aryl moiety attached through a —S(O)$_2$— linking group. "Arylsulfonyl"" can be also depicted as —S(O)$_2$-aryl. Arylsulfonyl includes, but not limited to, phenylsulfonyl.

"Diazo" refers to —N$^+$≡N.

"Hetero" refers to the replacement of at least one carbon atom member in a ring system with at least one heteroatom selected from N, S, and O. "Hetero" also refers to the replacement of at least one carbon atom member in a acyclic system. A hetero ring system or a hetero acyclic system may have 1, 2, or 3 carbon atom members replaced by a heteroatom.

"Halogen" or "halo" refers to fluorine, chlorine, bromine, or iodine.

As used herein, cycloalkylalkyl can be depicted as -alkylene-cycloalkyl. For example, (C$_3$-C$_6$)cycloalkyl(C$_1$-C$_4$)alkyl can be depicted as —(C$_1$-C$_4$)alkylene-(C$_3$-C$_6$)cycloalkyl.

As used herein, alkoxyalkyl can be depicted as -alkylene-O-alkyl. For example, (C$_1$-C$_7$)alkoxy(C$_1$-C$_4$)alkyl can be depicted as —(C$_1$-C$_4$)alkylene-O—(C$_1$-C$_7$)alkyl.

As used herein, cycloalkoxyalkyl can be depicted as -alkylene-O-cycloalkyl. For example, (C$_3$-C$_6$)cycloalkoxy(C$_1$-C$_4$)alkyl can be depicted as —(C$_1$-C$_4$)alkylene-O—(C$_3$-C$_6$)alkyl.

As used herein, arylalkyl can be depicted as -alkylene-aryl. For example, aryl(C$_1$-C$_4$)alkyl can be depicted as —(C$_1$-C$_4$)alkylene-aryl.

As used herein, aryloxyalkyl can be depicted as -alkylene-O-aryl. For example, aryloxy(C$_1$-C$_4$)alkyl can be depicted as —(C$_1$-C$_4$)alkylene-O-aryl.

As used herein, arylthioalkyl can be depicted as -alkylene-S-aryl. For example, arylthio(C$_1$-C$_4$)alkyl can be depicted as —(C$_1$-C$_4$)alkylene-S-aryl.

As used herein, arylsulfinylalkyl can be depicted as -alkylene-S(O)-aryl. For example, arylsufinyl(C$_1$-C$_4$)alkyl can be depicted as —(C$_1$-C$_4$)alkylene-S(O)-aryl.

As used herein, arylsulfonylalkyl can be depicted as -alkylene-S(O)$_2$-aryl. For example, arylsulfonyl(C$_1$-C$_4$)alkyl can be depicted as —(C$_1$-C$_4$)alkylene-S(O)$_2$-aryl.

The compounds described herein can exist as salts. For example, an acid salt containing an amine or other basic group can be obtained by reacting a compound with a suitable organic or inorganic acid, resulting in anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts. Other examples of anionic salts include tetrafluoroborate, hexafluorophosphate, hexafluoroarsenate and hexafluorosilicate (or monohydrogen hexafluorosilicate) salts.

Base salts containing a carboxylic acid or other acidic functional group can be prepared by reacting with a suitable base. Such a pharmaceutically acceptable salt may be made, for example, with alkali metal salts (especially sodium and potassium), alkaline earth metal salts (especially calcium and magnesium), aluminum salts or ammonium salts, as well as salts made from organic bases such as trimethylamine, triethylamine, morpholine, pyridine, piperidine, picoline, dicyclohexylamine. N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine. N,N'-bisdehydroabietylamine, glucamine, N-methylglucamine, collidine, quinine, quinoline, and basic amino acids, such as lysine and arginine.

The compounds described herein (e.g., compounds of Structural Formula I) can exist as solvates. As used herein, "solvate" refers to a chemical compound formed by the interactive of a solute (e.g., a compound or salt described herein) and one or more solvents. Thus, "solvate" includes solvates containing more than one type of solvent molecule (mixed solvates), for example, a toluene-ethyl acetate solvate or a (trifluoromethyl)benzene-diethyl ether-tetrahydrofuran solvate. Typically, the one or more solvents in solvates described herein is an organic solvent or a combination of organic solvents, although water can also form solvates, called hydrates. Exemplary solvates include (trifluoromethyl)benzene, ethyl acetate, toluene, diethyl ether and tetrahydrofuran solvates, or any combination thereof.

In some embodiments, the compound or salt (e.g., the compound of Structural Formula I) is a (trifluoromethyl)benzene solvate. In some embodiments of a solvate (e.g., a solvate of a compound of Structural Formula I), the solvate comprises (trifluoromethyl)benzene.

The compounds described herein (e.g., compounds of Structural Formula I) can also exist as a combination of a salt and solvate. A combination of a salt and a solvate can also be referred to as a solvated salt. An example of a solvated salt is a (trifluoromethyl)benzene solvate of the salt represented by the following structural formula:

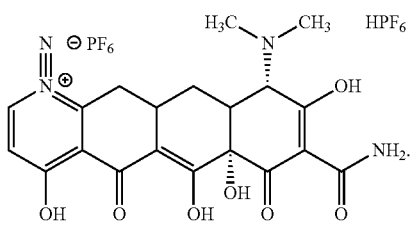

In some embodiments, a solvate (e.g., a mixed solvate, a solvated salt, a solvate of a compound of Structural Formula I) comprises from about 0.1 to about 2.5, from about 0.1 to about 1, from about 0.5 to about 1, from about 0.75 to about 1 or about 0.8 molar equivalents of solute per molar equivalent of the compound or salt.

Each carbon atom in a tetracycline compound described herein can be referred to using the numbering system depicted in the tetracycline compound depicted below:

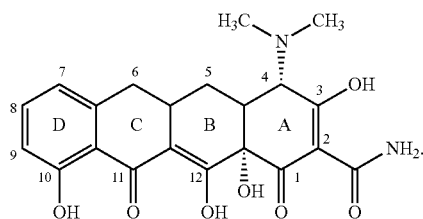

For example, a C7- or 7-substituted tetracycline compound refers to a tetracycline compound substituted with an indicated substituent (e.g., fluoro, diazo) at the carbon atom labeled with a "7" in the structure above. A C9- or 9-substituted tetracycline compound refers to a tetracycline compound substituted with an indicated substituent (e.g., fluoro, diazo) at the carbon atom labeled with a "9" in the structure above. A 7,9-disubstituted tetracycline compound refers to a tetracycline compound substituted with an indicated substituent at the carbon atom labeled with a "7" in the structure above and an indicated substituent at the carbon atom labeled with a "9" in the structure above.

Each ring in a tetracycline compound described herein can be referred to using the lettering scheme depicted in the tetracycline compound depicted above. For example, a tetracycline compound having a D ring substituent refers to a tetracycline compound substituted at the 7-, 8- or 9-position in the structure above.

The compounds described herein can also include various isomers and mixtures thereof. Certain of the compounds may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. When a chiral center is not defined as R or S, either a pure enantiomer or a mixture of both configurations is present.

"Racemate" or "racemic mixture" means a compound of equimolar quantities of two enantiomers, wherein such mixtures exhibit no optical activity; i.e., they do not rotate a plane of polarized light.

The compounds described herein can be prepared as individual isomers by either isomer-specific synthesis or by resolution from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer that is present divided by the combined weight of the enantiomer that is present and the weight of its optical isomer(s).

Methods Comprising Thermal Fluorination

One embodiment is a method of preparing a compound represented by Structural Formula II:

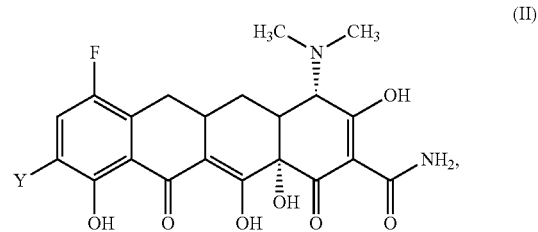

or a salt, solvate or combination thereof, by thermal fluorination. The values and alternative values for variable Y are as defined in the first, second or fourth embodiment, or any aspect of the foregoing. The method comprises heating a suspension comprising a non-polar organic solvent and a compound of Structural Formula I:

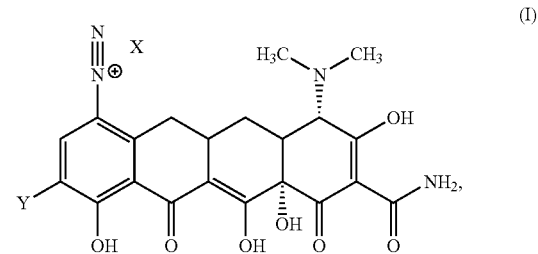

or a salt, solvate or combination thereof, wherein X is $PF_6^-$, $AsF_6^-$ or $HSiF_6^-$; and Y is as defined for the compound of Structural Formula II, at a temperature of from about 95° C. to about 200° C. to provide the compound of Structural Formula II, or the salt, solvate or combination thereof.

As used herein, "suspension" refers to a heterogeneous mixture comprising solid particles in a medium. Typically, the suspensions described herein are formed by suspending the compound of Structural Formula I in a non-polar organic solvent in which the compound of Structural Formula I is poorly soluble or insoluble.

Non-polar organic solvents useful in the thermal fluorinations of the invention are not particularly limited, except that they should not dissolve or only poorly dissolve a compound of Structural Formula I. Typically, a non-polar organic solvent has a dielectric constant of less than or about 15, more particularly, less than or about 10, yet more particularly, less than or about 5, or less than or about 2. Exemplary non-polar organic solvents useful in the thermal fluorinations of the invention include saturated or aromatic hydrocarbons (e.g., mineral oil, xylene, toluene, mesitylene), halogenated hydrocarbons (e.g., chlorobenzene, trifluorotoluene, perfluoromethyldecalin, perfluoro-1,2-dimethylhexane, perfluorodecalin, perfluorotoluene, perfluorooctane, perfluorononane), ethers (e.g., diphenylether, ligroin) and fluorinated organic solvents (e.g., partially fluorinated organic solvents, perfluorinated organic solvents).

"Perfluorinated organic solvent" refers to an organic compound in which each C—H bond has been replaced with a C—F bond. A "perfluorinated organic solvent" does not contain any C—H bonds. "Perfluorinated organic solvents" can contain heteroatoms, such as nitrogen, oxygen and sulfur, in addition to carbon and fluorine. Exemplary perfluorinated organic solvents include perfluoromethyldecalin, perfluoro-1,2-dimethylhexane, perfluorodecalin, perfluorotoluene, perfluorooctane, perfluorononane, perfluoroalkylamines (Fluorinert® FC-40), perfluorotributylamines (Fluorinert® FC-43), perfluorotripentylamine (Fluorinert® FC-70) and perfluorotripropylamine (Fluorinert® FC-3283). In preferred embodiments, the non-polar organic solvent is a perfluorinated organic solvent, in particular, a perfluorinated organic solvent sold under the trade name Fluorinert® (e.g., perfluorotributylamines (Fluorinert® FC-43)).

In some embodiments, the non-polar organic solvent has a boiling point of at least or about 100° C., preferably, at least or about 125° C., more preferably, at least or about 150° C.

In some embodiments, the method comprises heating the suspension at a temperature of from about 100° C. to about 160° C. from about 120° C. to about 160° C., from about 125° C. to about 140° C. or from about 130° C. to about 135° C.

When the boiling point of the non-polar organic solvent is less than the temperature at which the suspension is heated, undesired solvent loss through evaporation can occur. Thus, in preferred embodiments, the boiling point of the non-polar organic solvent is greater than or approximately equal to the temperature at which the suspension is heated. Undesired solvent loss can also be mitigated when the boiling point of a solvent is less than the temperature at which the suspension is heated by conducting the thermal fluorination in a scaled pressure vessel.

The thermal fluorination can be conducted in an inert vessel. As used herein, "inert vessel" refers to any vessel that does not react chemically with the chemical species or the combination of chemical species in a reaction for which it is being used or does not cause the chemical species or combination of chemical species to react chemically. Particularly preferred inert vessels include vessels constructed of or coated with a perfluoropolymer, such as polytetrafluoroethylene or perfluoroalkoxy alkanes (PFA). Other inert vessels include steel-based (e.g., stainless steel) vessels or Hastelloy® vessels, which can be inert, for example, under thermal fluorinations involving a suspension of a compound of Structural Formula I in a non-polar organic solvent in which the compound of Structural Formula I has near-zero solubility in the non-polar organic solvent.

In certain embodiments, the method of preparing a compound of Structural Formula II by thermal fluorination, further comprises diazotizing a compound of Structural Formula III:

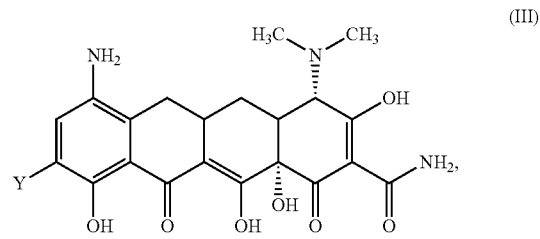

or a salt, solvate or combination thereof, wherein Y is as defined for the compound of Structural Formula II wherein at least one of $R^A$ and $R^B$ is not hydrogen when Y is —$(C_1$-$C_4)$alkylene-N($R^A$)($R^B$), —$(C_1$-$C_4)$alkylene-N($R^F$)—C(O)—[C($R^D$)($R^E$)]$_{1-4}$—N($R^A$)($R^B$), —N($R^A$)($R^B$), —N($R^F$)—C(O)—[C($R^D$)($R^E$)]$_{1-4}$—N($R^A$)($R^B$) or —N($R^F$)—(O)$_m$—$(C_1$-$C_4)$alkylene-N($R^A$)($R^B$), to provide the compound of Structural Formula I, or salt, solvate or combination thereof. The purpose of the proviso for Y in Structural Formula (III) is to remove the possibility that there are two primary amino groups simultaneously present in the molecule in the diazotization reaction.

As used herein, "diazotizing" or "diazotization" refers to a chemical reaction in which a primary amino group is replaced with a diazo group. Typical conditions for diazo formation are known to those of skill in the art and include treatment of a compound comprising a primary amino group (e.g., a compound of Structural Formula III) with nitrous acid, typically generated in situ, for example, from sodium nitrite in the presence of a mineral acid. Diazotization can also be accomplished by treating a compound comprising a primary amino group (e.g., a compound, salt, solvate or combination thereof of Structural Formula III) with an alkylnitrite, such as butyl nitrite, in the presence of a mineral acid. In some embodiments, the diazotization reaction is conducted in the presence of an aqueous solution of a mineral acid.

As used herein, "mineral acid" refers to an acid derived from one or more inorganic compounds. A "mineral acid" forms a hydrogen ion and a conjugate base ion when dissolved in water. Exemplary mineral acids include hydrochloric acid, nitric acid, phosphoric acid, sulfuric acid, boric acid, hydrofluoric acid, hydrobromic acid, perchloric acid, hexafluorophosphoric acid, fluoroboric acid, hexafluoroarsenic acid and hexafluorosilicilic acid. Preferred mineral acids (for use in the diazotization reactions described herein) include hexafluorophosphoric acid, fluoroboric acid, hexafluoroarsenic acid and hexafluorosilicilic acid.

Typically, the diazo compound is isolated as the diazonium salt of the mineral acid used in the diazotization reaction.

In some embodiments of a method of preparing a compound of Structural Formula II by thermal fluorination, Y is hydrogen. In an aspect of these embodiments, the method further comprises nitrating the compound of Structural Formula II, or the salt, solvate or combination thereof, to provide a compound of Structural Formula IV having a nitro group:

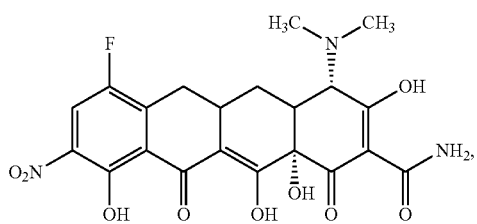

(IV)

or a salt, solvate or combination thereof.

As used herein, "nitrating" or "nitration" refers to a chemical reaction in which a hydrogen atom is replaced with a nitro (—NO$_2$) group. An aromatic nitration is a chemical reaction in which the hydrogen atom and the nitro group are substituents on an aromatic ring. Nitration of a compound of Structural Formula II, for example, involves aromatic nitration and, consequently, can be accomplished using electrophilic aromatic substitution. Conditions for nitration and, in particular, aromatic nitration, of a compound are known to those of skill in the art, and include treating a compound (e.g., a compound of Structural Formula II wherein Y is hydrogen, a compound of Structural Formula IX) with an alkyl nitrate, such as isopropyl nitrate, in the presence of a mineral acid, such as sulfuric acid. Alternative conditions for nitration include treating a compound (e.g., a compound of Structural Formula II wherein Y is hydrogen, a compound of Structural Formula IX) with an alkali metal nitrate salt, such as sodium nitrate or potassium nitrate, in the presence of a mineral acid, such as sulfuric acid, or treating a compound directly with nitric acid.

In a further aspect of the embodiments of a method of preparing a compound of Structural Formula II wherein Y is hydrogen by thermal fluorination, the method further comprises reducing the nitro group of the compound of Structural Formula IV, or the salt, solvate or combination thereof, to provide a compound of Structural Formula V:

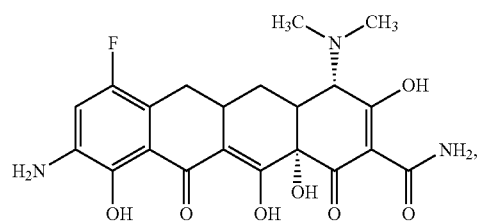

(V)

or a salt, solvate or combination thereof.

Conditions for reducing an aromatic nitro group to a primary amino group are known to those of skill in the art and include catalytic hydrogenation, iron in acidic media, sodium hydrosulfite, sodium sulfide or hydrogen sulfide and a base, tin(II) chloride, titanium(III) chloride, zinc and samarium. In some embodiments, the nitro group of the compound of Structural Formula IV or the compound of Structural Formula VII is reduced to the primary amino group by catalytic hydrogenation, for example, using palladium on carbon or platinum on carbon, in the presence of hydrogen.

In a yet further aspect of a method of preparing a compound of Structural Formula II wherein Y is hydrogen by thermal fluorination, the method further comprises functionalizing the primary amino group of the compound of Structural Formula V, or the salt, solvate or combination thereof, to provide a compound of Formula (VI):

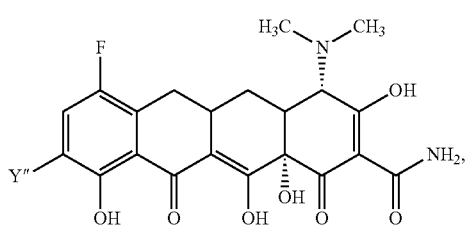

(VI)

or a salt, solvate or combination thereof, wherein the values and alternative values for Y'', and the variables forming Y'', are as described in the first, second or eighth embodiment, or any aspect of the foregoing.

As used herein, "functionalize" or "functionalization" refers to a chemical reaction in which one or more hydrogen atoms of a primary amino group is independently replaced with a recited substituent. For example, to form a compound of Structural Formula VI wherein Y'' is —N(H)—C(O)—CH$_2$-pyrrolidin-1-yl, one hydrogen atom of the primary amino group on the D ring of the compound of Structural Formula V is functionalized with —C(O)—CH$_2$-pyrrolidin-1-yl.

Functionalization of a primary amino group can be effected by a variety of methods known to those of skill in the art. For example, a compound of Structural Formula V or Structural Formula VIII can be treated with an addition reagent designed to react with the primary amino group on the D ring of the compound of Structural Formula V or Structural Formula VIII, respectively, to form a compound of Structural Formula VI or Structural Formula VII, respectively, thereby functionalizing the amino group by addition of all, or a component of, the addition reagent to the amino group. Various addition reagents can be used to functionalize a primary amino group. For example, an addition reagent such as R—C(O)-LG, wherein R—C(O)— is the substituent to be added to the amino group and LG is a leaving group (e.g., chloride), can be used to functionalize a primary amino group. Addition reagents can also be, for example, isocyanates (R—N=C=O), activated esters (such as N-hydroxy-succinimidyl esters), acid chlorides (R—C(O)—Cl), sulfonyl chlorides (R—S(O)$_2$Cl), activated sulfonamides, activated heterocycles, activated heteroaryls, chloroformates (R—O—C(O)Cl) and cyanoformates (R—O—C(O)—CN). An addition reagent can also be an aldehyde or ketone that reacts with the amine under reductive conditions to form an alkylated amine. Other reagents that can be used to functionalize a primary amino group or form an addition reagent to functionalize a primary amino group include peptide coupling reagents, e.g., PyBOP® (benzotriazole-1-yl-oxy-tris-pyrrolidino-phosphonium hexafluorophosphate), HBtU (2-(1H-benzotriazole-1-yl)-1,1,3,3-tetramethyluronium hexafluorophosphate), HBtU/HOBt (2-(1H-benzotriazole-1-yl)-1,1,3,3-tetramethyluronium hexafluorophosphate/N-hydroxybenzotriazole) and DCC (dicyclohexylcarbodiimide).

In some embodiments of a method of preparing a compound of Structural Formula II by thermal fluorination, Y is selected from the group consisting of —N($R^A$)($R^B$), —N($R^F$)—C(O)—[C($R^D$)($R^E$)]$_{1-4}$—N($R^A$)($R^B$), —N($R^F$)—C(O)—N($R^A$)($R^B$), —N($R^F$)—C(O)—($C_1$-$C_6$)alkyl, —N($R^F$)—C(O)-heterocyclyl, —N($R^F$)—C(O)-heteroaryl, —N($R^F$)—C(O)-carbocyclyl, —N($R^F$)—C(O)-aryl, —N($R^F$)—S(O)$_m$—($C_1$-$C_4$)alkylene-N($R^A$)($R^B$), —N($R^F$)—S(O)$_m$—($C_1$-$C_4$)alkylene-carbocyclyl, and —N($R^F$)—S(O)—($C_1$-$C_4$)alkylene-aryl, for example, Y is —N(H)—C(O)—CH$_2$-pyrrolidin-1-yl. In some embodiments of a method of preparing a compound of Structural Formula II by thermal fluorination, Y is selected from the group consisting of —N($R^A$)($R^B$), —N($R^F$)—C(O)—[C($R^D$)($R^E$)]$_{1-4}$—N($R^A$)($R^B$), —N($R^F$)—C(O)—N($R^A$)($R^B$), —N($R^F$)—C(O)—($C_1$-$C_6$)alkyl, —N($R^F$)—C(O)-heterocyclyl, —N($R^F$)—C(O)-heteroaryl, —N($R^F$)—C(O)-carbocyclyl, —N($R^F$)—C(O)-aryl, —N($R^F$)—S(O)$_m$—($C_1$-$C_4$)alkylene-N($R^A$)($R^B$), —N($R^F$)—S(O)$_m$—($C_1$-$C_4$)alkylene-carbocyclyl, and —N($R^F$)—S(O)$_m$—($C_1$-$C_4$)alkylene-aryl, wherein at least one of $R^A$ and $R^B$ is not hydrogen when Y is —N($R^A$)($R^B$), —N($R^F$)—C(O)—[C($R^D$)($R^E$)]$_{1-4}$—N($R^A$)($R^B$) or —N($R^F$)—S(O)$_m$—($C_1$-$C_4$)alkylene-N($R^A$)($R^B$), for example, Y is —N(H)—C(O)—CH$_2$-pyrrolidin-1-yl.

In an aspect of these embodiments, the method further comprises reducing the nitro group of a compound of Structural Formula VII:

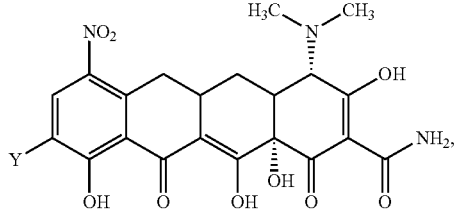

or a salt, solvate or combination thereof, to form the compound of Structural Formula III, or salt, solvate or combination thereof. Specific conditions for reducing a nitro group to a primary amino group are as discussed above.

In a further aspect of these embodiments, the method further comprises functionalizing a primary amino group of a compound of Structural Formula VIII:

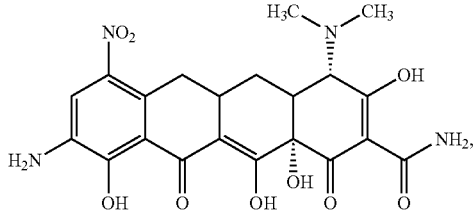

or a salt, solvate or combination thereof, to form the compound of Structural Formula VII, or salt, solvate or combination thereof. Specific conditions for functionalizing a primary amino group are as discussed above.

In a yet further aspect of these embodiments, the method further comprises nitrating a compound of Structural Formula IX:

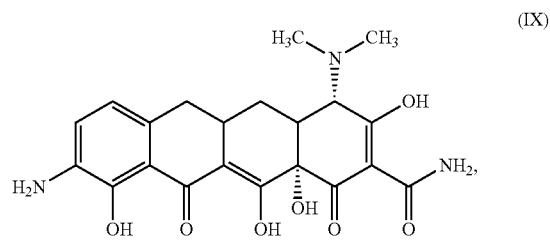 [SMILES: CN(C)[C@@H]1C(O)=C(C(N)=O)C(=O)[C@@]2(O)C(O)=C3C(=O)c4c(ccc(N)c4O)CC3CC12]

or a salt, solvate or combination thereof, to form the compound of Structural Formula VIII, or salt, solvate or combination thereof. Specific conditions for nitration and, in particular, aromatic nitration, are as discussed above.

Another particular embodiment of a method comprising thermal fluorination provides a method of preparing a compound represented by Structural Formula Ia:

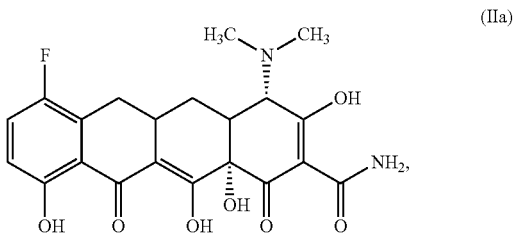 [SMILES: CN(C)[C@@H]1C(O)=C(C(N)=O)C(=O)[C@@]2(O)C(O)=C3C(=O)c4c(O)ccc(F)c4CC3CC12]

or a salt, solvate or combination thereof. The method comprises heating a suspension comprising a perfluorinated organic solvent and a compound of Structural Formula Ia:

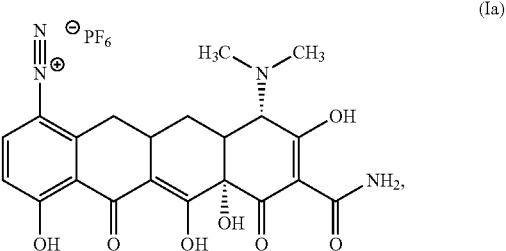

or a salt, solvate or combination thereof, at a temperature of from about 120° C. to about 160° C. to provide the compound of Structural Formula IIa, or the salt, solvate or combination thereof. Alternative solvents and conditions (e.g., temperature ranges) for the thermal fluorination are as discussed above.

In an aspect of this particular embodiment, the method further comprises nitrating the compound of Structural Formula IIa, or the salt, solvate or combination thereof, to provide a compound of Structural Formula IV:

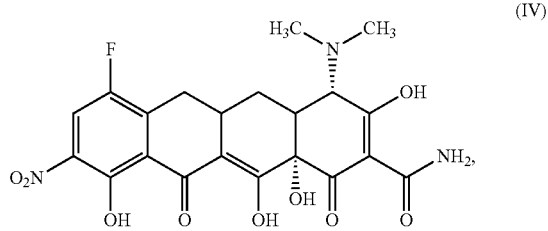 [SMILES: CN(C)[C@@H]1C(O)=C(C(N)=O)C(=O)[C@@]2(O)C(O)=C3C(=O)c4c(O)c([N+](=O)[O-])cc(F)c4CC3CC12]

(IV)

or a salt, solvate or combination thereof. Specific conditions for nitration and, in particular, aromatic nitration, are as discussed above.

In a further aspect of this particular embodiment, the method further comprises reducing the nitro group of the compound of Structural Formula IV, or the salt, solvate or combination thereof, to provide a compound of Structural Formula V:

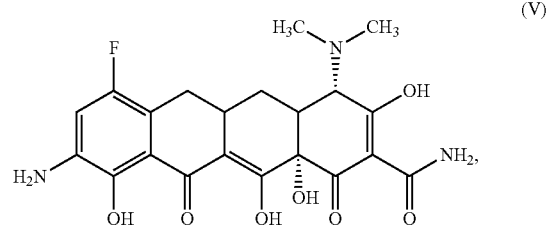 [SMILES: CN(C)[C@@H]1C(O)=C(C(N)=O)C(=O)[C@@]2(O)C(O)=C3C(=O)c4c(O)c(N)cc(F)c4CC3CC12]

(V)

or a salt, solvate or combination thereof. Specific conditions for reduction of an aromatic nitro group to a primary amino group are as discussed above.

In a yet further aspect of this particular embodiment, the method further comprises functionalizing the primary amino group of the compound of Structural Formula V, or the salt, solvate or combination thereof, to provide a compound of Formula (VIa):

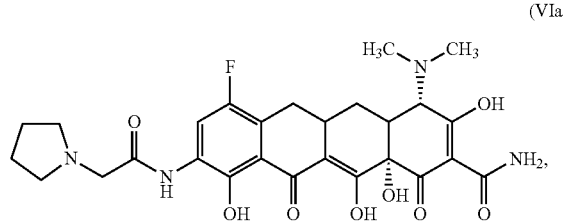

(VIa)

or a salt, solvate or combination thereof. Specific conditions for functionalizing a primary amino group are as discussed above. In a preferred aspect of this particular aspect of this particular embodiment, the compound of Structural Formula V, or the salt, solvate or combination thereof, is treated with Cl—C(O)—CH$_2$-pyrrolidin-1-yl to provide the compound of Structural Formula VIa, or the salt, solvate or combination thereof.

In another aspect of this particular embodiment, the method further comprises diazotizing a compound of Structural Formula IIIa:

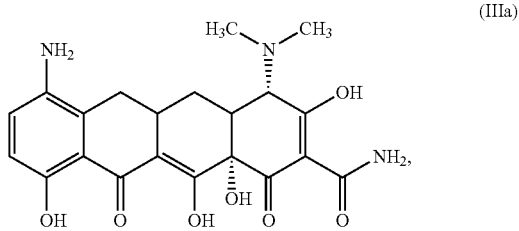 [SMILES: CN(C)[C@@H]1C(O)=C(C(N)=O)C(=O)[C@@]2(O)C(O)=C3C(=O)c4c(O)ccc(N)c4CC3CC12]

(IIIa)

or a salt, solvate or combination thereof, to provide the compound of Structural Formula Ia, or salt, solvate or combination thereof. Specific conditions for diazotizing a compound are as discussed above.

Methods Comprising Photolylic Fluorination

Another embodiment is a method of preparing a compound represented by Structural Formula II, or a salt, solvate or combination thereof, by photolytic fluorination. The values and alternative values for variable Y in Structural Formula II are as defined in the first, second or fourth embodiment, or any aspect of the foregoing. The method comprises irradiating a solution comprising an ionic liquid and a compound of Structural Formula XI:

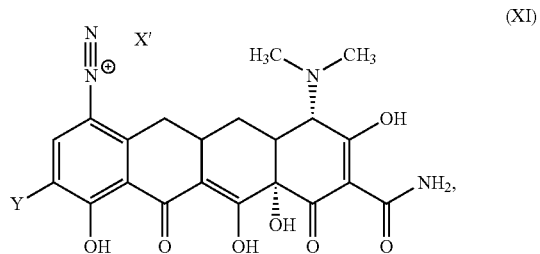

(XI)

or a salt, solvate or combination thereof, wherein X' is $BF_4^-$, $PF_6^-$, $AsF_6^-$ or $HSiF_6^-$, preferably $BF_4^-$; and Y is as defined above for the compound of Structural Formula II, to provide the compound of Structural Formula II, or the salt, solvate or combination thereof.

As used herein, "solution" refers to a homogeneous mixture. Typically, the solutions described herein are formed by dissolving the compound of Structural Formula XI in an ionic liquid in which the compound of Structural Formula I is soluble.

As used herein, "ionic liquid" refers to a salt (comprising a cation and an anion) in a liquid state. Typically, ionic liquids are liquid below about 100° C. Exemplary cations used in ionic liquids include 1,3-dialkyl imidazolium (as in 1-butyl-3-methylimidazolium tetrafluoroborate, 1-butyl-2,3-dimethylimidazolium tetrafluoroborate, for example); 1-alkylpyridinium (as in 1-butyl-3-methylpyridinium tetrafluoroborate, for example); 1,2-dialkylpyrazolium (as in 1,2,4-trimethylpyrazolium methylsulfate, for example); 1,1-dialkylpyrrolidinium (as in 1-butyl-1-methylpyrrolidium chloride, for example); ammonium (as in benzyltrimethylammonium tribromide or tributylmethylammonium methyl sulfate, for example); phosphonium (as in tetrabutylphosphonium methanesulfonate or trihexyltetradecylphosphonium bromide, for example); and sulfonium (as in cyclopropyldiphenylsulfonium tetrafluoroborate, for example). Preferred cations include the 1,3-dialkyl imidazolium cation.

Exemplary anions used in ionic liquids include halides, acetate, dicyanamide, hexafluorophosphate, hexafluoroantimonate, tetrafluoroborate, bis(trifluoromethylsulfonyl)imide, tribromide, triiodide, hydroxide, hydrogen sulfate, trifluoromethanesulfonate, alkylcarbonate, alkylsulfate, dialkylphosphate, alkanoate, tosylate, formate, alkylsulfate, alkylphosphate and glycolate. Preferred anions include hexafluorophosphate and tetrafluoroborate.

Exemplary ionic liquids include any combination of a cation and an anion listed above. Preferred ionic liquids include 1-butyl-3-methylimidazolium tetrafluoroborate, 1-butyl-2,3-dimethylimidazolium tetrafluoroborate, 1-butyl-3-methylpyridinium tetrafluoroborate and 1-butyl-3-methylimidazolium hexafluorophosphate.

As used herein, "irradiating" means exposing to radiation. Typically, the radiation is ultraviolet radiation (electromagnetic radiation having a wavelength of about 10 nm to about 400 nm). In some embodiments, the method of preparing a compound represented by Structural Formula II, or a salt, solvate or combination thereof, by photolytic fluorination comprises irradiating the solution with ultraviolet light. For example, 254 nm-wavelength light has been found to be quite effective in the photolytic fluorination reactions described herein.

In certain embodiments of a method of preparing a compound of Structural Formula II by photolytic fluorination, the method further comprises diazotizing a compound of Structural Formula III:

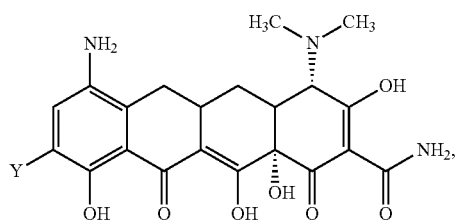

(III)

or a salt, solvate or combination thereof, wherein Y is as defined for the compound of Structural Formula II wherein at least one of $R^A$ and $R^B$ is not hydrogen when Y is —$(C_1-C_4)$alkylene-$N(R^A)(R^B)$, —$(C_1-C_4)$alkylene-$N(R^F)$—$C(O)$—$[C(R^D)(R^E)]_{1-4}$—$N(R^A)(R^B)$, —$N(R^A)(R^B)$, —$N(R^F)$—$C(O)$—$[C(R^D)(R^E)]_{1-4}$—$N(R^A)(R^B)$, or —$N(R^F)$—$S(O)_m$—$(C_1-C_4)$alkylene-$N(R^A)(R^B)$, to provide the compound of Structural Formula I, or salt, solvate or combination thereof. Specific conditions for diazotizing a compound are as discussed above for methods comprising thermal fluorination.

In an aspect of these certain embodiments of a method of preparing a compound of Structural Formula II by photolytic fluorination, the method further comprises reducing the nitro group of a compound of Structural Formula XII:

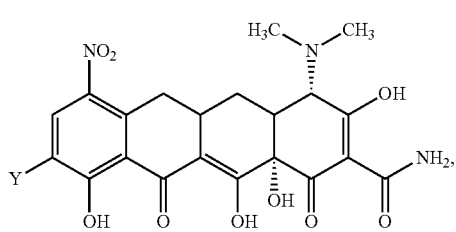

(XII)

or a salt, solvate or combination thereof, wherein Y is as defined for Structural Formula II wherein Y is not nitro and at least one of $R^A$ and $R^B$ is not hydrogen when Y is —$(C_1-C_4)$alkylene-$N(R^A)(R^B)$, —$(C_1-C_4)$alkylene-$N(R^F)$—$C(O)$—$[C(R^D)(R^E)]_{1-4}$—$N(R^A)(R^B)$, —$N(R^A)(R^B)$, —$N(R^F)$—$C(O)$—$[C(R^D)(R^E)]_{1-4}$—$N(R^A)(R^B)$, or —$N(R^F)$—$S(O)_m$—$(C_1-C_4)$alkylene-$N(R^A)(R^B)$, to form the compound of Structural Formula III, or salt, solvate or combination thereof. Specific conditions for reducing a nitro group to a primary amino group are as discussed above for methods comprising thermal fluorination. The chemical reasons for the proviso for Y in Structural Formula XII will be understood by a person skilled in the art, and include removing the possibility that there are two nitro groups in the molecule simultaneously during the reduction.

In some embodiments of a method of preparing a compound of Structural Formula II by photolytic fluorination, Y is hydrogen. In an aspect of these embodiments, the method further comprises nitrating the compound of Structural Formula II, or the salt, solvate or combination thereof, to provide a compound of Structural Formula IV:

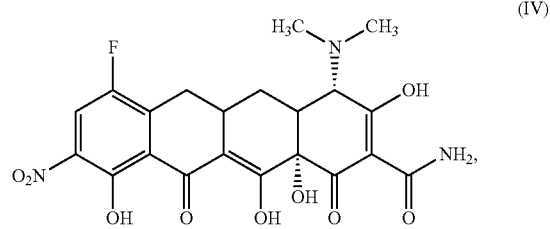 [SMILES: CN(C)[C@@H]1C(O)=C(C(N)=O)C(=O)[C@@]2(O)C(O)=C3C(=O)c4c(O)c([N+](=O)[O-])cc(F)c4CC3CC12]

(IV)

or a salt, solvate or combination thereof. Specific conditions for nitration and, in particular, aromatic nitration, are as discussed above for methods comprising thermal fluorination.

In a further aspect of the embodiments of a method of preparing a compound of Structural Formula II wherein Y is hydrogen by photolytic fluorination, the method further comprises reducing the nitro group of the compound of Structural Formula IV, or the salt, solvate or combination thereof, to provide a compound of Structural Formula V:

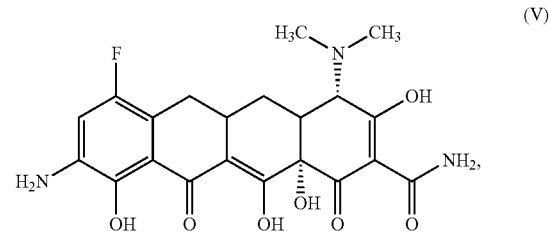 [SMILES: CN(C)[C@@H]1C(O)=C(C(N)=O)C(=O)[C@@]2(O)C(O)=C3C(=O)c4c(O)c(N)cc(F)c4CC3CC12]

(V)

or a salt, solvate or combination thereof. Specific conditions for reducing a nitro group to a primary amino group are as described above for methods comprising thermal fluorination.

In a yet further aspect of a method of preparing a compound of Structural Formula II wherein Y is hydrogen by photolytic fluorination, the method further comprises functionalizing the primary amino group of the compound of Structural Formula V, or the salt, solvate or combination thereof, to provide a compound of Formula (VI):

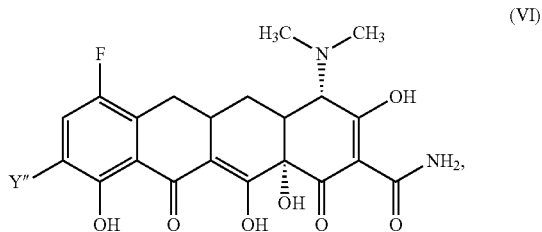

(VI)

or a salt, solvate or combination thereof, wherein the values and alternative values for Y", and the variables forming Y", are as described in the first, second or eighth embodiment, or any aspect of the foregoing. Specific conditions for functionalizing a primary amino group are as described above for methods comprising thermal fluorination.

In some embodiments of a method of preparing a compound of Structural Formula II by photolytic fluorination, Y is selected from the group consisting of —N($R^A$)($R^B$), —N($R^F$)—C(O)—[C($R^D$)($R^E$)]$_{1-4}$—N($R^A$)($R^B$), —N($R^F$)—C(O)—N($R^A$)($R^B$), —N($R^F$)—C(O)—(C$_1$-C$_6$)alkyl, —N($R^F$)—C(O)-heterocyclyl, —N($R^F$)—C(O)-heteroaryl, —N($R^F$)—C(O)-carbocyclyl, —N($R^F$)—C(O)-aryl, —N($R^F$)—S(O)$_m$—(C$_1$-C$_4$)alkylene-N($R^A$)($R^B$), —N($R^F$)—S(O)$_m$—(C$_1$-C$_4$)alkylene-carbocyclyl, and —N($R^F$)—S(O)$_m$—(C$_1$-C$_4$)alkylene-aryl, for example, Y is —N(H)—C(O)—CH$_2$-pyrrolidin-1-yl. In some embodiments of a method of preparing a compound of Structural Formula II by thermal fluorination, Y is selected from the group consisting of —N($R^A$)($R^B$), —N($R^F$)—C(O)—[C($R^D$)($R^E$)]$_{1-4}$—N($R^A$)($R^B$), —N($R^F$)—C(O)—N($R^A$)($R^B$), —N($R^F$)—C(O)—(C$_1$-C$_6$)alkyl, —N($R^F$)—C(O)-heterocyclyl, —N($R^F$)—C(O)-heteroaryl, —N($R^F$)—C(O)-carbocyclyl, —N($R^F$)—C(O)-aryl, —N($R^F$)—S(O)$_m$—(C$_1$-C$_4$)alkylene-N($R^A$)($R^B$), —N($R^F$)—S(O)$_m$—(C$_1$-C$_4$)alkylene-carbocyclyl, and —N($R^F$)—S(O)$_m$—(C$_1$-C$_4$)alkylene-aryl, wherein at least one of $R^A$ and $R^B$ is not hydrogen when Y is —N($R^A$)($R^B$), —N($R^F$)—C(O)—[C($R^D$)($R^E$)]$_{1-4}$—N($R^A$)($R^B$) or —N($R^F$)—S(O)$_m$—(C$_1$-C$_4$)alkylene-N($R^A$)($R^B$), for example, Y is —N(H)—C(O)—CH$_2$-pyrrolidin-1-yl.

In an aspect of these embodiments, the method further comprises reducing the nitro group of a compound of Structural Formula VII:

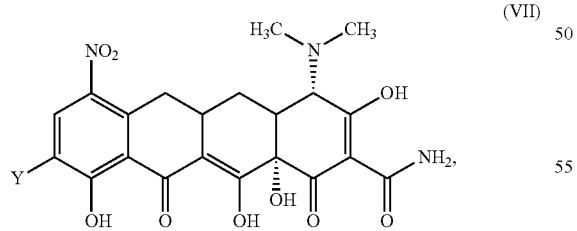

(VII)

or a salt, solvate or combination thereof, to form the compound of Structural Formula III, or salt, solvate or combination thereof. Specific conditions for reducing a nitro group to a primary amino group are as discussed above for methods comprising thermal fluorination.

In a further aspect of these embodiments, the method further comprises functionalizing a primary amino group of a compound of Structural Formula VIII:

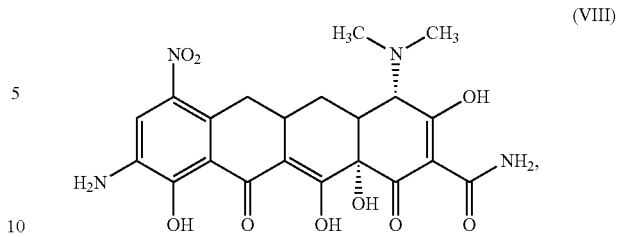

(VIII)

or a salt, solvate or combination thereof, to form the compound of Structural Formula VII, or salt, solvate or combination thereof. Specific conditions for functionalizing a primary amino group are as described above for methods comprising thermal fluorination.

In a yet further aspect of these embodiments, the method further comprises nitrating a compound of Structural Formula IX:

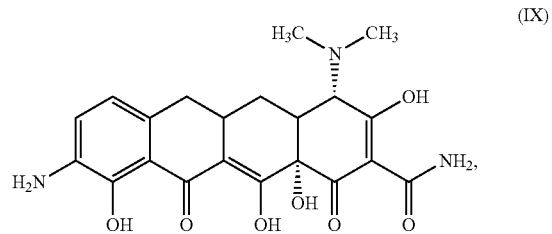 [SMILES: CN(C)[C@@H]1C(O)=C(C(N)=O)C(=O)[C@@]2(O)C(O)=C3C(=O)c4c(ccc(N)c4O)CC3CC12]

(IX)

or a salt, solvate or combination thereof, to form the compound of Structural Formula VIII, or salt, solvate or combination thereof. Specific conditions for nitration and, in particular, aromatic nitration, are as discussed above for methods comprising thermal fluorination.

Another particular embodiment of a method comprising photolytic fluorination provides a method of preparing a compound represented by Structural Formula IIa, or a salt, solvate or combination thereof. The method comprises irradiating a solution comprising an ionic liquid and a compound of Structural Formula XIa:

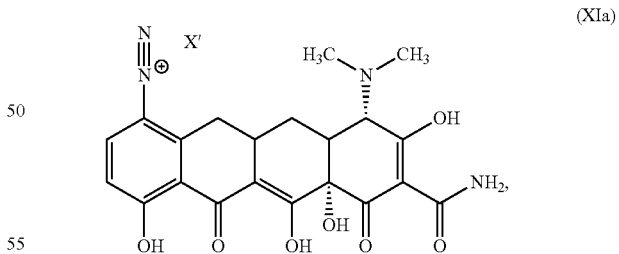

(XIa)

or a salt, solvate or combination thereof, to provide the compound of Structural Formula IIa, or the salt, solvate or combination thereof. Particular ionic liquids and conditions (e.g., wavelength of radiation) for the photolytic fluorination are as discussed above. In a preferred aspect of this particular embodiment, X' is $BF_4^-$.

In another aspect of this particular embodiment, the method further comprises nitrating the compound of Structural Formula IIa, or the salt, solvate or combination thereof, to provide a compound of Structural Formula IV:

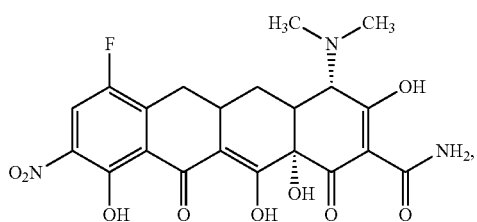

(IV)

or a salt, solvate or combination thereof. Specific conditions for nitration, in particular, aromatic nitration, are as described above for methods comprising thermal fluorination.

In a further aspect of this particular embodiment, the method further comprises reducing the nitro group of the compound of Structural Formula IV, or the salt, solvate or combination thereof, to provide a compound of Structural Formula V:

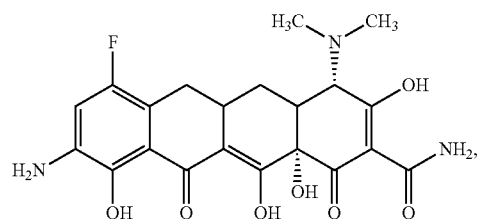

(V)

or a salt, solvate or combination thereof. Specific conditions for reducing a nitro group to a primary amino group are as described above for methods comprising thermal fluorination.

In a yet further aspect of this particular embodiment, the method further comprises functionalizing the primary amino group of the compound of Structural Formula V, or the salt, solvate or combination thereof, to provide a compound of Formula (VIa):

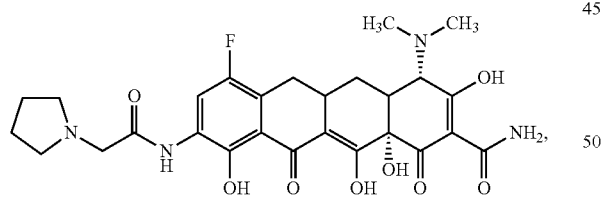

(VIa)

or a salt, solvate or combination thereof. Specific conditions for functionalizing a primary amino group are as described above for methods comprising thermal fluorination. In a preferred aspect of this particular aspect of this particular embodiment, the compound of Structural Formula V, or the salt, solvate or combination thereof, is treated with Cl—C(O)—CH$_2$-pyrrolidin-1-yl to provide the compound of Structural Formula VIa, or the salt, solvate or combination thereof.

EXEMPLIFICATION

The following abbreviations and terms have the indicated meanings:

| Abbreviation/Term | Meaning |
|---|---|
| Ac | acetyl |
| AcOH | acetic acid |
| aq | aqueous |
| AUC | area under the curve |
| BMIM | 1-butyl-3-methylimidazolium |
| Bn | benzyl |
| brine | saturated aqueous sodium chloride |
| Bu | butyl |
| Cbz | benzyloxycarbonyl |
| CH$_3$CN or MeCN | acetonitrile |
| d | density |
| DCM | dichloromethane |
| DMSO | dimethyl sulfoxide |
| ESI | electrospray ionization |
| equiv. or eq. | equivalent(s) |
| Et | ethyl |
| Et$_2$O | ethyl ether |
| EtOAc | ethyl acetate |
| g | gram |
| h, hr | hour |
| HPLC | high performance liquid chromatography |
| i | iso |
| IPA or IPAc | isopropyl alcohol |
| L | liter(s) |
| LCMS | liquid chromatography-mass spectrometry |
| m | meta |
| Me | methyl |
| MeOH | methanol |
| mg | milligram(s) |
| min | minute |
| mL | milliliter(s) |
| MS | mass spectrum |
| MTBE | methyl tert-butyl ether |
| MW | molecular weight |
| N | normal |
| NBS | N-bromosuccinimide |
| nm | nanometer(s) |
| NMP | N-methyl-2-pyrrolidone |
| NMR | nuclear magnetic resonance spectrometry |
| o | ortho |
| Ph | phenyl |
| Pr | propyl |
| Py | pyridine |
| rt or r.t. | room temperature |
| SM | starting material |
| TBME | tert-butyl methyl ether |
| TFA | trifluoroacetic acid |
| THF | tetrahydrofuran |
| wt | weight |

Example 1. Preparation of 7-Fluorosancycline from 7-Aminosancycline

Preparation of 7-aminosancycline

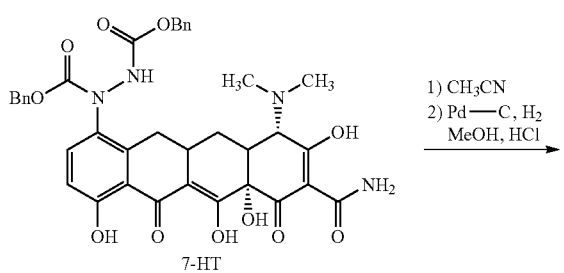

7-HT

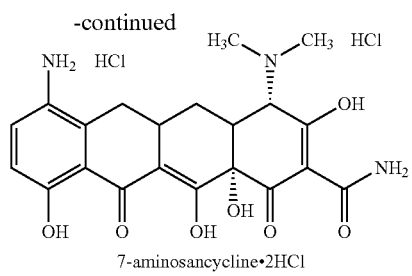

7-aminosancycline·2HCl

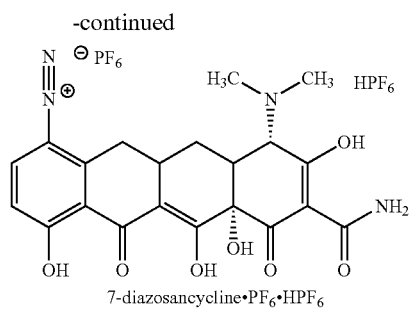

7-diazosancycline·PF$_6$·HPF$_6$

| Material | Qty | MW | d | Mol | Mole eq. |
|---|---|---|---|---|---|
| 7-HT | 80 g | 712.7 | — | 0.112 | 1.0 |
| Pd-C E101 NEW | 4 g | — | — | — | 5% wt |
| 6N HCl | 84 mL | — | — | 0.5 | 4.5 eq. |
| MeOH | 800 mL | — | — | — | 10x |
| CH$_3$CN | 800 mL | — | — | — | 10x |
| 7-aminosancycline*2HCl | 56.3 g | 502.35 (429.42) | — | 0.112 | 1.0 |

In a 2-L, round-bottomed flask equipped with a mechanical stirrer, CH$_3$CN and 7-HT were charged under nitrogen. The mixture was stirred at room temperature for 18 h. The solid was filtered, washed with methyl t-butyl ether (MTBE), and dried to yield pre-treated 7-HT.

A 2-L, round-bottomed flask equipped with a mechanical stirrer was charged with MeOH, 6 N aqueous HCl, and the pre-treated 7-HT. The mixture was stirred until the 7-HT was dissolved. The solution was vacuumed briefly and purged once with N$_2$. Pd—C was added. The suspension was vacuumed briefly and purged three times with N$_2$, then three times with H$_2$. The reaction was stirred at rt under a hydrogen atmosphere until completion (if using a hydrogen balloon, the overhead space was briefly vacuumed and refilled with H$_2$ after 30 and 90 minutes). The reaction mixture was filtered through a Celite® pad. The Celite® pad was washed with MeOH and the filtrate was concentrated on a rotary evaporator to 3x volume (240 mL) or less. Isopropanol (320 mL) was slowly added to the stirring red oil residue, followed by the addition of MTBE (480 mL). The mixture was stirred at rt for 1 h. The solid was filtered, washed with MTBE, and dried to yield 44 g (78% yield) of 7-aminosancycline*2HCl as a light tan solid (90% purity by HPLC): $^1$H-NMR (400 MHz, CD$_3$OD) δ 7.52 (d, J=9.2 Hz, 1H), 6.97 (d, J=9.2 Hz, 1H), 4.15 (s, 1H), 3.25-2.9 (m, 9H), 2.45 (m, 1H), 2.3 (m, 1H), 1.65 (m, 1H); MS (ESI) m/z 430.1 (M+H).

Preparation of 7-fluorosancycline By Thermal Fluorination

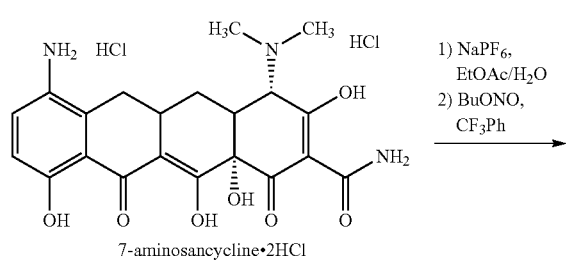

7-aminosancycline·2HCl

1) NaPF$_6$, EtOAc/H$_2$O
2) BuONO, CF$_3$Ph

| Material | Qty | MW | d | Mol | Mole eq. |
|---|---|---|---|---|---|
| 7-amino-sancycline*2HCl | 44 g | 502.35 | — | 0.088 | 1.0 |
| 6N HCl | 3.7 mL | — | — | 0.022 | 0.25 |
| NaPF$_6$ | 36.9 g | 167.95 | — | 0.22 | 2.5 |
| H$_2$O | 440 mL | — | — | — | 10x |
| EtOAc | 660 mL | — | — | — | 15x |
| butyl nitrite | 15.4 mL | 103.12 | 0.882 | 0.132 | 1.5 |
| EtOAc | 352 mL | — | — | — | 8x |
| CF$_3$Ph | 528 mL | — | — | — | 12x |
| 7-diazo-sancycline*PF$_6$*HPF$_6$ | 64.4 g | 732.08 | — | 0.088 | 1.0 |

A 1-L, round-bottomed flask equipped with a stir bar was charged with H$_2$O, 7-aminosancycline*2HCl, 6 N aqueous HCl, and NaPF$_6$. The deep red solution was stirred at room temperature for 30 minutes and transferred to a 2 L separatory funnel. The solution was extracted twice with EtOAc (440 mL+220 mL). The organic phases were combined, dried over sodium sulfate, and filtered.[1] The filtrate was concentrated to an oily residue.[2] The Oil was dissolved in EtOAc up to 352 mL total volume and the solution was cooled to 8° C. Butyl nitrite was added dropwise over 20 minutes with a syringe pump while keeping the temperature at <8° C. The reaction was stirred at 8° C. for 1 h. The cold (8° C.) reaction solution was then transferred slowly to a separate flask with a mechanical stirrer containing 528 mL (12x volume) of stirring CF$_3$Ph at 0° C. Once the addition was complete, the resulting slurry was stirred at 0° C. for 1 h and filtered under a N$_2$ blanket. The filter cake was slurried and washed with dichloromethane (DCM)[3] and the solid was dried in a vacuum oven to yield 61 g of the desired product as a light tan powder (95% by wt). The product was a CF$_3$Ph solvate or isolated containing residual CF$_3$Ph (0.86 mol equiv by $^1$H NMR) with 7% mol residual ethyl acetate: $^1$H-NMR (400 MHz, CD$_3$OD) δ 8.52 (d, J=9.8 Hz, 1H), 7.28 (d, 1=9.8 Hz, 1H), 4.11 (s, 1H), 3.1-2.8H) 2.35 (m, 1H), 1.7 (m, 1H), MS (ESI) m/z 441.2 (M+H).

Notes:
[1] The purpose of the filtration was to not only remove sodium sulfate, but also residual dark solid.
[2] The concentration of the EtOAc solution was to remove water (azeotrope), which is important prior to the next step (diazonium formation).
[3] DCM was added up to the top of the filter cake and the solid was slurried before applying vacuum to the filtrate.

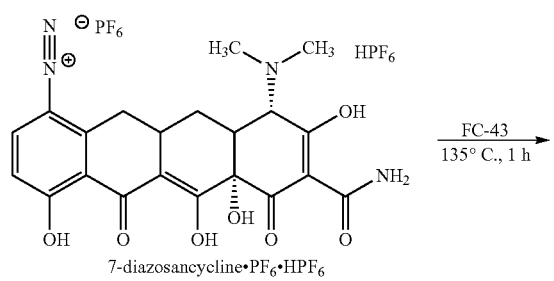

7-diazosancycline·PF$_6$·HPF$_6$

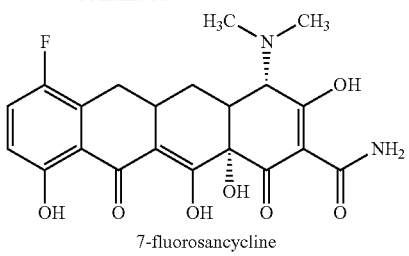

7-fluorosancycline

| Material | Qty | MW | d | Mol | Mole eq. |
|---|---|---|---|---|---|
| 7-fluorosancycline*HPF$_6$ | 47 g | 732.08 | — | 0.04 (1) | 1.0 |
| 1N NaOH | 95 mL | — | — | 0.095 | n/a |
| H$_2$O | 705 mL | — | — | — | 15x |
| DCM | 940 mL | — | — | — | 20x |
| heptane | 120 mL | — | — | — | 2.5x |
| 7-fluorosancycline | 17.4 g | 432.4 | — | 0.04 | 1.0 |

In a 2-L, round-bottomed flask equipped with a mechanical stirrer, a pH probe, and a thermocouple, water and 7-fluorosancycline*HPF$_6$[(1)] were charged. Aqueous NaOH (1 N) was added slowly until pH=7.2.[(2)] The aqueous suspension was then transferred to a separatory funnel and extracted with 564 mL (12× volume) of DCM for 10 minutes. The suspension was filtered through a pad of Celite®. The filtrate was charged back to the separatory funnel and the DCM layer was separated. The pH of the aqueous layer (pH 7.5) was adjusted back to 7.2 using 6 N aqueous HCl (a few drops) and the aqueous layer was extracted a second time with 376 mL (8× volume) of DCM. The suspension was filtered through a pad of Celite® and the filtrate was charged back to the separatory funnel. The DCM layer was separated and combined with the first DCM extraction. The combined DCM solutions were dried over sodium sulfate, filtered, and concentrated to an oil of about 40-50 mL total volume. The oil was then added slowly to a separate flask containing 120 mL of stirring heptane and the resulting slurry was stirred at room temperature for 1 h. The solid was filtered, washed with heptane, and dried in a vacuum oven (30° C.) until the weight became stable to yield 11.3 g of the desired product as a bright yellow solid (HPLC: 7-fluorosancycline=90%, sancycline=4%; 80% by wt): $^1$H NMR (400 MHz, CD$_3$OD) δ 7.24 (t, J=9.2 Hz, 1H), 6.8 (m, 1H), 3.5 (s, 1H), 3.1 (m, 1H), 3.0 (m, 1H), 2.75 (s, 6H), 2.65 (m, 1H), 2.3 (m, 1H), 2.15 (m, 1H), 1.65 (m, 1H), MS (ESI) m/z 433.2 (M+H).

Notes:
(1) SM potency was 37%, which translated to 17.4 g free base (0.04 mol).
(2) Initial pH=1.8, pH was adjusted up to 7.2 to a point where the reading on the pH meter was stable at 7.20 for at least 1 minute. Actual volume of 1 N aqueous NaOH needed was 95 mL.

Preparation of 7-fluorosancycline By Photolytic Fluorination

7-Fluorosancycline was also prepared using a photolytic fluorination.

| Material | Qty | MW | d | Mol | Mole eq. |
|---|---|---|---|---|---|
| 7-diazo-sancycline*PF6*HPF6 | 61 g | 732.08 | — | 0.0833 | 1.0 |
| 3M ™ Fluorinert ™ FC-43 | 732 mL | — | — | — | 12x |
| 7-fluorosancycline·HPF$_6$ | 48.2 g | 578.37 | — | 0.0833 | 1.0 |

In a 2-L PTFE (polytetrafluoroethylene) reaction vessel equipped with a mechanical stirrer, a thermocouple, a N$_2$ inlet, and an off-gassing condenser (at rt) connected to a scrubber,[(1)] FC-43 and 7-diazosancycline*PF$_6$*HPF$_6$ were charged. The reaction was slowly heated under N$_2$ sweeping with stirring to 135° C. internal temperature. Once the target temperature was reached, stirring was continued for 1 h under nitrogen flushing while keeping the reaction temperature between 135° C. and 140° C. The reaction mixture was cooled to room temperature and filtered. The filter cake was washed twice with MTBE and dried under high vacuum to yield 47 g of the desired product (97% by wt) as a brown solid (HPLC: 7-fluorosancycline=72%, sancycline=4%, 7-OH sancycline=2.8%). MS of 7-fluorosancycline: (ESI) m/z 433.2 (M+H).

Notes:
(1) The scrubber consisted of a flask containing stirring aqueous NaOH + bromothymol blue pH indicator and was equipped with an open "chimney" filled with strongly basic resin.

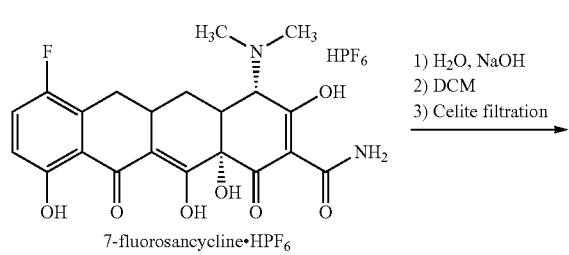

7-fluorosancycline·HPF$_6$

1) H$_2$O, NaOH
2) DCM
3) Celite filtration

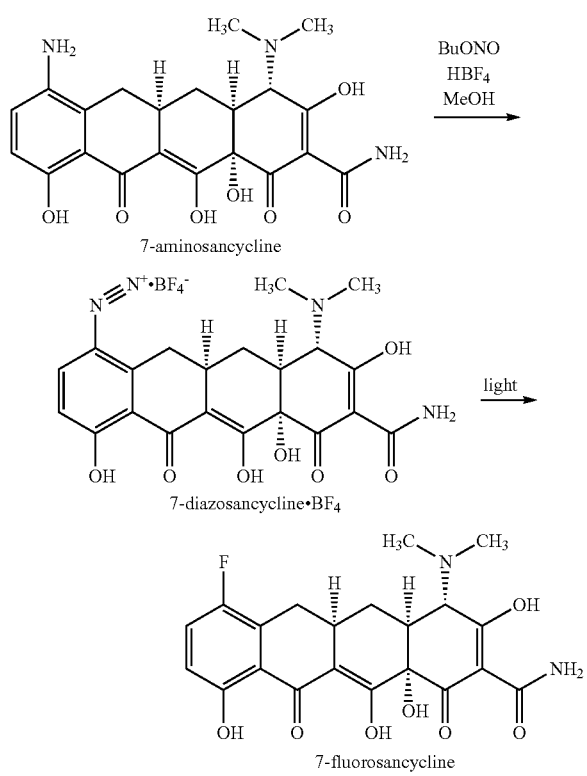

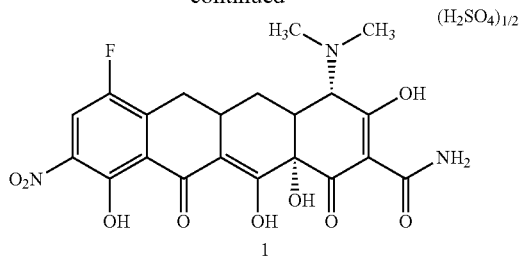

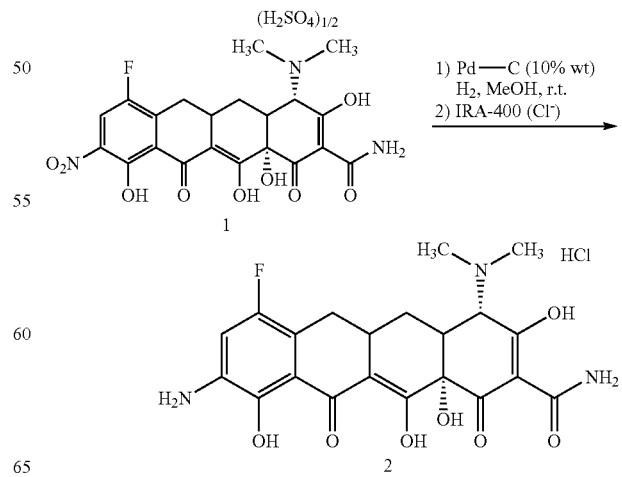

| Material | Lot | Qty | MW | d | Mol | Mole eq. |
|---|---|---|---|---|---|---|
| 7-fluoro-sancycline | 433-100-1 | 11.3 g | 432.4 | — | 0.026 | 1.0 |
| H$_2$SO$_4$ | | 34 mL | — | — | — | 3x |
| Isopropyl nitrate | | 3.15 mL | 105.09 | 1.04 | 0.0312 | 3.2 |
| 1 | 433-102-1 | 14.95 g | 575.09 (H$_2$SO$_4$) 477.12 (free base) | — | 0.026 | 1.0 |

Specifically, 7-aminosancycline (120 mg) was dissolved in 2 mL methanol. The solution was cooled with ice/water. To the solution was added 0.2 mL 48% HBF$_4$ followed by 0.1 mL n-BuNO$_2$. After stirring at the same temperature for 10 minutes, diethyl ether (8 mL) was added to the reaction mixture to precipitate 7-diazosancycline*BF$_4$. After filtration and drying, 110 mg 7-diazosancycline*BF$_4$ was obtained as a yellow solid. MS (ESI) m/z 441.2.

In a photoreactor, 7-diazosancycline*BF$_4$ (100 mg) was dissolved in 1 mL 1-methyl-3-butylimidazolium tetrafluoroborate. The solution was irradiated while being cooled with running water for 18 h. After the reaction was complete, HPLC analysis showed the reaction mixture contained 58.8% of 7-fluorosancycline and 17.7% of sancycline. The crude product was purified by preparative HPLC to yield 70 mg of 7-fluorosancycline (containing some sancycline). MS (ESI) m/z 433.2 (M+H).

Example 2. Preparation of Eravacycine from 7-Fluorosancycline

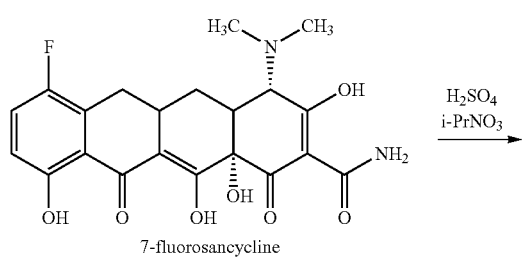

To a 100-mL, round-bottomed flask equipped with a mechanical stirrer was added H$_2$SO$_4$, and the flask was cooled with a brine/ice bath. 7-Fluorosancycline was added to the cold sulfuric acid. The reaction mixture was stirred at 0° C. under nitrogen sweep until the starting material was completely dissolved. Isopropyl nitrate was added over 30 minutes while keeping the reaction temperature below 2° C. The reaction was stirred at 0° C. until completion, as monitored by HPLC. The reaction mixture was then added slowly to a separate flask containing 30× volume of a stirred mixture of 283 mL i-PrOH and 57 mL heptane at 0° C. The resulting suspension was stirred at 0° C. for 1 h and the solid was filtered,[1] washed with a cold mixture of 57 mL i-PrOH and 11 mL heptane followed by heptane, and dried in a vacuum oven at 30° C. overnight to yield 12.8 g of the desired product as a yellow solid (LCMS: compound 1=85%; 67% by wt): MS (ESI) m/z 478.2 (M+H).

Notes:
(1) Filtration rate was moderate and stable. The solid obtained was a dry, yellow powder. Only 5% compound 1 was lost in the mother liquor.

| Material | Lot | Qty | MW | d | Mol | Mole eq. |
|---|---|---|---|---|---|---|
| 1 | 433-102-1 | 12.8 g | 575.09 | — | 0.022 | 1.0 |
| Pd—C | 10R39 | 0.64 g | — | — | — | 5% wt |
| 3N HCl | | 14.6 mL | — | — | 0.044 | 2.0 |
| MeOH | — | 384 mL | — | — | — | 30x |
| 2 | | — | (447.4 free base) | — | 0.022 | 1.0 |
| | | 10.6 g | (483.9•HCl) | | | |
| | | — | (520.3•2HCl) | | | |

To a 1-L reaction flask equipped with a stir bar was added MeOH and 3 N aqueous HCl. Compound 1 and 10% Pd—C were added portionwise to the stirring solvent mixture. The reaction mixture was vacuumed briefly and purged with dry nitrogen three times, followed by three times with hydrogen (balloon). The reaction was stirred at rt until completion. The reaction mixture was filtered through a pad of Celite®, and the Celite® pad was washed with MeOH. The filtrate was charged into a round-bottomed flask and 1.3 g (10% wt) of Siliabond DMT was added. The mixture was stirred at t for 90 minutes and filtered. The solid was washed with MeOH. The filtrate was charged to a round-bottomed flask and 77 g (6× weight) of wet Amberlyst resin IRA-400 (chloride form) was added. The suspension was stirred at room temperature for 2 h and the resin was removed by filtration and washed (soaking+vacuum pulling) with methanol. The filtrate was concentrated on a rotary evaporator to roughly half the volume. Isopropanol (64 mL) was added. The mixture was concentrated further to an oil and charged with 102 mL of i-PrOH and 51 mL of MTBE. The mixture was stirred at room temperature for 18 h (overnight). The solid was collected by filtration, washed with MTBE, and dried in a vacuum oven at 30° C. to yield 9.1 g of compound 2 as a dark orange powder (mono-HCl salt, 81% yield (corrected), HPLC purity=83%): MS (ESI) m-z 448.2 (M+H).

| Material | Qty | MW | d | Mol | Mole eq. |
|---|---|---|---|---|---|
| Step (1) | | | | | |
| 2 | 9.1 g | 483.9 | — | 0.0188 | 1.0 |
| MeOH | 91 mL | — | — | — | 10x |
| HCl (2.2N in EtOH) | 14.9 mL | — | — | 0.0329 | 1.75 |
| EtOAc | 364 mL | — | — | — | 40x |
| Heptane | 91 mL | — | — | — | 10x |
| Step (2) | | | | | |
| Product from step (1) | (9.78 g) | 520.34 | — | 0.0188 | 1.0 |
| 3 (90%) | 4.49 g | 184.1 | — | 0.0244 | 1.3 |
| NMP | 55 mL | — | — | — | 6x |
| EtOAc | 546 mL | — | — | — | 60x |
| 4(eravacycline) | 11.9 g | 631.48 (558.6) | — | 0.0188 | 1.0 |

Step (1): Mono-HCl salt 2 (9.1 g) was suspended in MeOH, and HCl (2.1 N in EtOH) was added. To the resulting dark solution was added 20× volume (182 mL) EtOAc over 30 minutes. The slurry was stirred for an additional 30 minutes. Another 20× volume portion of EtOAc (182 mL) and 10× volume heptane (91 mL) were added. The suspension was stirred at room temperature for 1 h. The solid was filtered, washed with heptane, and dried in a vacuum oven. The resulting light brown solid (bis-HCl salt, 9.22 g) was taken to step (2).

Step (2): N-methyl-2-pyrrolidone (NMP) and the bis-HCl salt from step (1) were charged into a round-bottomed flask and stirred at room temperature until full dissolution (typically 30 min). The solution was cooled to <0° C. with a brine bath. Acid chloride 3 was added portionwise while keeping the reaction temperature below 0° C. The reaction was stirred at 0° C. for 10 min and quenched by adding 2 eq of water (0.677 mL). The reaction solution was transferred to 60× volume (546 mL) stirring EtOAc. The resulting slurry was stirred for 1 h and filtered under a $N_2$ blanket. The filter cake was washed with EtOAc and dried on the filter with

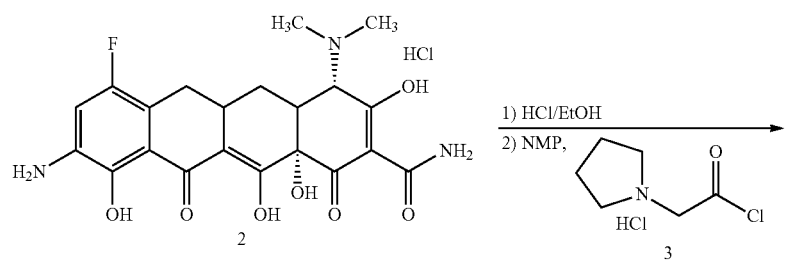

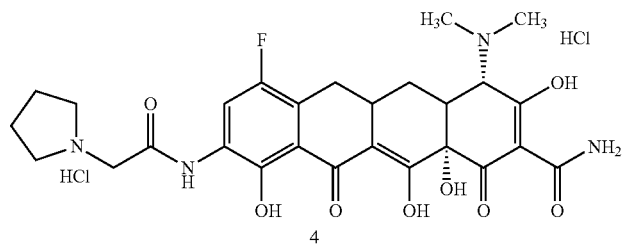

vacuum under a continuous flow of dry nitrogen. The solid was transferred to a stirring solution of acetone:H₂O (50:1, v/v, 455 mL/9.1 mL). The resulting slurry was stirred at room temperature for 2 h, filtered, washed with acetone, and dried under vacuum to yield 11.3 g of compound 4 (eravacycline) as a dark yellow solid (91% corrected yield, HPLC purity=89%): MS (ESI) m/z 559.3 (M+H).

Example 3. Preparation of Eravacycline from 9-Aminosancycline Using a Photolytic Fluorination

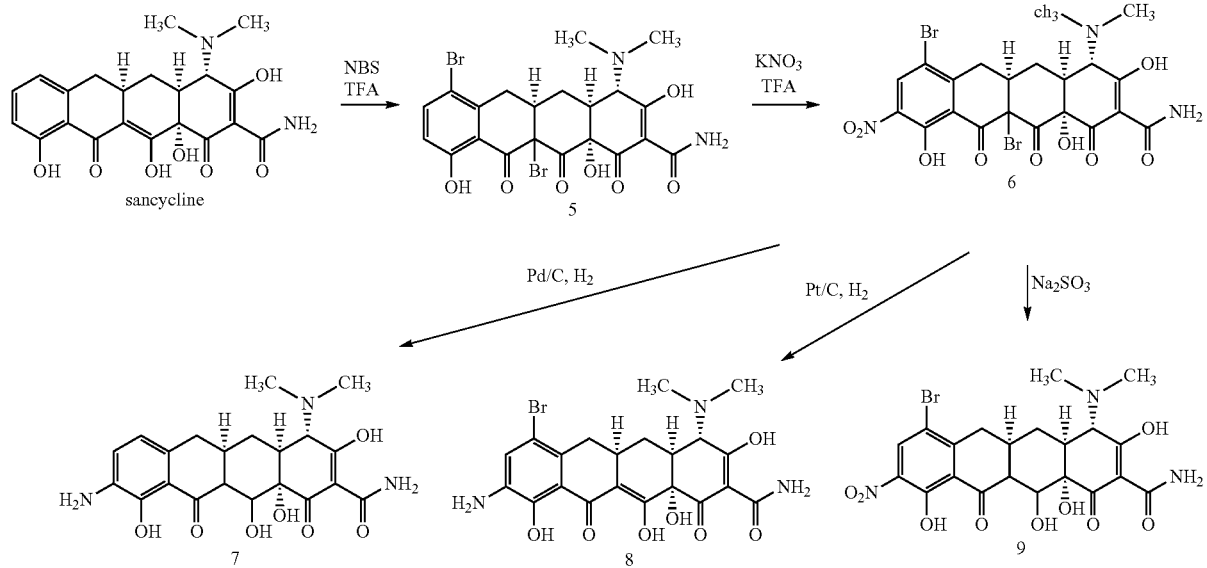

Sancycline (0.414 g, 1.0 mmol) was dissolved in trifluoroacetic acid (TFA). The solution was cooled to 0° C. To the solution was added N-bromosuccinimide (NBS, 0.356 g, 2.1 mmol). The reaction was complete after stirring at 0° C. for 1 h. The reaction mixture was allowed to warm to rt. Solid KNO₃ (0.11 g, 0.11 mmol) was added and the reaction mixture was stirred at rt for 1 h. The reaction solution was added to 75 mL cold diethyl ether. The precipitate was collected by filtration and dried to give 0.46 g of compound 6. Compound 6 can then be reduced to compounds 7, 8, or 9 using standard procedures.

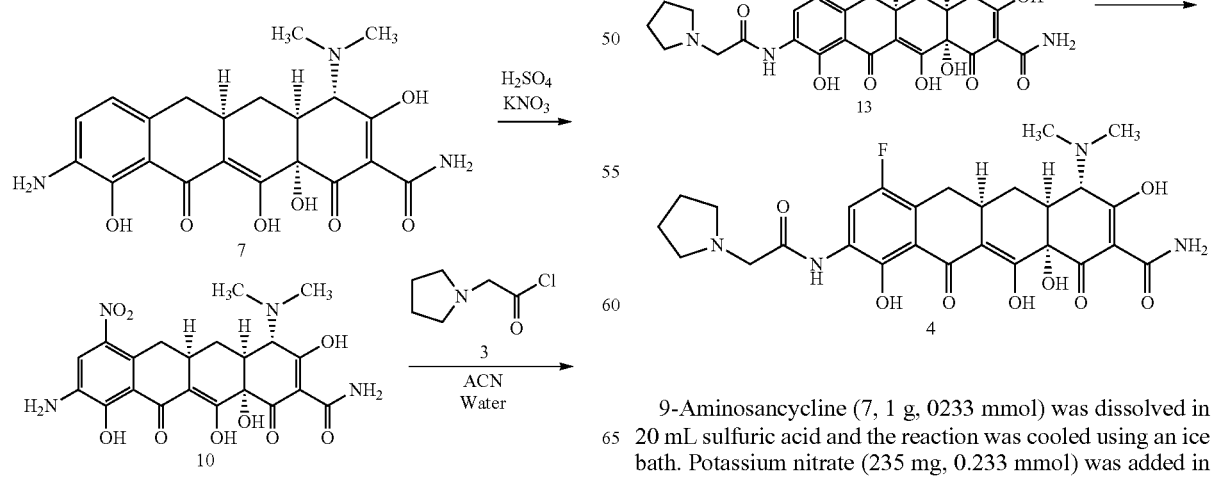

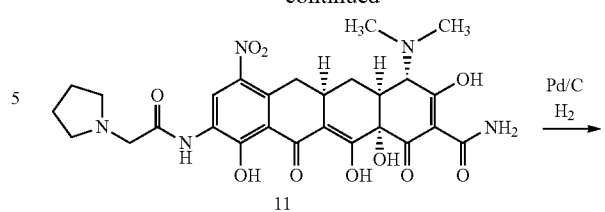

9-Aminosancycline (7, 1 g, 0233 mmol) was dissolved in 20 mL sulfuric acid and the reaction was cooled using an ice bath. Potassium nitrate (235 mg, 0.233 mmol) was added in several portions. After stirring for 15 min, the reaction mixture was added to 400 mL MTBE followed by cooling using an ice bath. The solid was collected by filtration. The filter cake was dissolved in 10 mL water and the pH of the aqueous solution was adjusted to 5.3 using 25% aqueous NaOH. The resulting suspension was filtered, and the filter cake was dried to give 1 g compound 10: MS (ESI) m/z 475.1 (M+1).

Compound 10 (1.1 g) was dissolved in 20 mL of water and 10 mL of acetonitrile. To the solution was added acyl chloride 3 (in two portions: 600 mg and 650 mg). The pH of the reaction mixture was adjusted to 3.5 using 25% aqueous NaOH. Another portion of acyl chloride (800 mg) was added. The reaction was monitored by HPLC analysis. Product 11 was isolated from the reaction mixture by preparative HPLC. Lyophilization gave 1.1 g of compound 11: MS (ESI) m/z 586.3 (M+1).

Compound 11 (1.1 g) was dissolved in methanol. To the solution was added concentrated HCl (0.5 mL) and 10% Pd—C (600 mg). The reaction mixture was stirred under a hydrogen atmosphere (balloon). After the reaction was completed, the catalyst was removed by filtration. The filtrate was concentrated to give 1 g of compound 12: $^1$H NMR (400 MHz, DMSO), 8.37 (s, 1H), 4.38-4.33 (m, 3H), 3.70 (br s, 2H), 3.30-2.60 (m, 12H), 2.36-2.12 (m, 2H), 2.05-1.80 (m, 4H), 1.50-1.35 (m, 1H); MS (ESI) m/z 556.3 (M+1).

Compound 12 (150 mg) was dissolved in 1 mL of 48% HBF$_4$. To the solution was added 21 mg of NaNO$_2$. After compound 12 was completely converted to compound 13 (LC/MS m/z 539.2), the reaction mixture was irradiated with 254 nm light for 6 h while being cooled with running water. The reaction mixture was purified by preparative HPLC using acetonitrile and 0.05 N aqueous HCl as mobile phases to yield the compound 4 (eravacycline, 33 mg) as a bis-HCl salt (containing 78% of 4 and 10% of the 7-H byproduct, by HPLC): MS (ESI) m/z 559.3 (M+1).

Example 4. Thermal Fluorination of 7-Diazosancycline: Counterion Effects

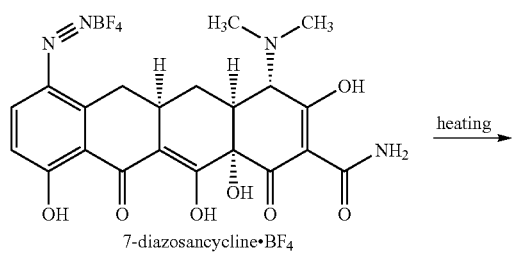

7-diazosancycline•BF$_4$

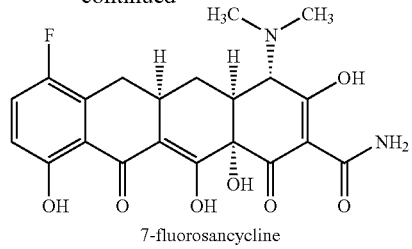

7-fluorosancycline

U.S. Pat. No. 3,239,499 ("the '499 Patent"), issued Mar. 8, 1966, reports a thermal fluorination reaction in which 7-diazosancycline tetrafluoroborate is converted to 7-fluorosancycline by heating with a flame. The '499 Patent only reports that fluorinated product formed. There is no yield, no analytical data and no byproduct information associated with the transformation. Such a direct thermal decomposition using a flame is a known bench-scale technique used to convert only minute quantities of starting material. The method disclosed in the '499 Patent does not have practical applications or meaningful value beyond a simple proof of concept, and is not a usable large-scale process.

Manufacturing of 7-diazosancycline*BF$_4$ using the procedure reported in the '499 Patent was attempted, but no product was obtained. Instead, 7-diazosancycline*BF$_4$ was manufactured by treating 7-aminosancycline with n-butyl nitrite in methanol in the presence of aqueous HBF$_4$ to form 7-diazosancycline*BF$_4$. The 7-diazosancycline*BF$_4$ product precipitated by addition of ether to the reaction mixture.

Instead of heating using an open flame as described in the '499 Patent, 7-diazosancycline*BF$_4$ was heated to 160° C. in an oil bath for 1 h. The reaction gave 38.7% 7-F product by LC (100 mg SM, see experiment 407-27 in Table 1). The major impurities have a m/z of 481 on LCMS and are likely BF$_3$ adducts of sancycline. Repeating the thermal fluorination according to the procedure described in the '499 Patent on larger scale appeared to increase the amount of "481" byproducts.

The heating of a solid can only be performed at small scale and would not be applicable to manufacturing, for example, of eravacycline, for clinical and commercial use. Because of this, the thermal fluorination reaction using 7-diazosancycline*BF$_4$ was also examined in a variety of solvents (e.g., xylenes, perfluorinated solvents) (see Table 1). Many of the solvent conditions were superior the procedure in the '499 Patent, especially at small scale (approximately 10 mg). For example, the reaction in m-xylene gave 65% of product by LC (see experiment 272-63 in Table 1), but at larger scale, more "481" byproducts formed.

TABLE 1

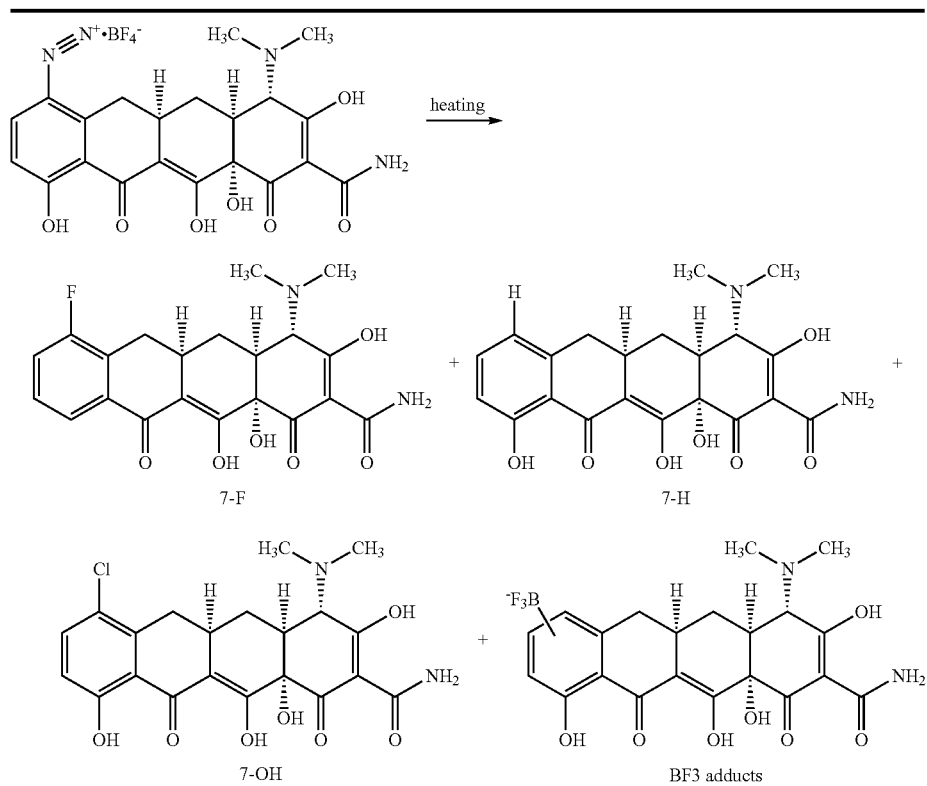

| Experiment[a] | Solvent | Condition(s) | 7-F | 7-H | 7-OH | BF3 adducts | Comment(s) |
|---|---|---|---|---|---|---|---|
| 404-27[b] | no | 160° C. | 38.7% | | | | '499 Patent conditions |
| 272-53 | toluene | Microwave 150° C., 1 h | 59% | 10% | 3% | some | |
| 272-54 | CF$_3$-benzene | Microwave 150° C., 1 h | 50% | 9% | 3% | some | |
| 272-59 | m-xylene | 165° C., 40 min | 48% | 8% | 4% | some | |
| 272-63 | m-xylene | 150° C., 1 h | 65% | 5% | 2% | some | |
| 272-63 | m-xylene | 140° C., 1 h | 57% | 12% | 1% | some | |
| 272-66 | mesitylene | 150° C., 40 min | 56% | 8% | 1% | some | |
| 272-68 | none | 160° C., vacuum, 40 min | 61% | 5% | 1% | some | |
| 272-71 | BMIM•BF$_4$ | 150° C. | tiny | major | | some | |
| 272-71 | Diphenyl ether | 150° C. | 53% | 8% | 2% | some | |
| 272-71 | o-xylene | 150° C. | 46% | 10% | 2% | some | Additive 1[c] |
| 272-71 | o-xylene | 150° C., 7 min | none | | some | some | 2 drops concentrated H$_2$SO$_4$ |
| 272-73 | o-xylene | 130° C., 1.5 h | 48% | 8% | | some | 2.5% SM |
| 272-75 | HC(OMe)$_3$ | 135° C., 1 h | | | | some | decomposed |
| 289-59 | PhCl | 135° C., 2.5 h | 38% | 5% | 9% | 4% | |
| 289-59 | MIBK | 135° C., 1.5 h | 25% | 11% | 4% | 3% | Many other impurities |
| 289-59 | IPAc | 135° C., 1.5 h | 36% | 9% | 7% | 5% | |
| 289-59 | Anisol | 135° C., 1.5 h | 40% | 10% | 7% | 4% | |
| 289-59 | 2,6-lutidine | 135° C., 1.5 h | | | | | decomposed |
| 289-60 | SiO2[d] | 130° C., 1 h | 30% | 19% | 7% | 2% | |
| 289-63 | mesitylene | 60° C. | none | major | | | Added Cu |
| 289-67 | BMIM•BF$_4$ | 60° C. | none | major | | | Added CsF |
| 289-69 | Na$_2$SO$_4$[d] | 140° C., 1 h | 49% | 8% | 6% | 4% | |
| 289-69 | Mg$_2$SO$_4$[d] | 140° C., 1 h | 49% | 11% | 5% | 3% | |

TABLE 1-continued

| | | | | | | |
|---|---|---|---|---|---|---|
| 289-69 | CuSO$_4$[d] | 130° C., 1 h | 55% | 11% | 4% | 6% |
| 289-69 | Celite[d] | 130° C., 1 h | 54% | 9% | 6% | 4% |

[a]all the reactions were at a few milligram scale
[b]this condition is to mimic the '499 Patent conditions
[c]Additive 1: tri-t-butylphospinniumtetrafluoroborate
[d]The diazonium salt was mixed with the corresponding solid first, then heated to the indicated temperature. No solvent.

The thermal fluorination of 7-diazosancycline*BF$_4$ was also performed using perfluorinated solvents at milligram scale (see Table 2). Promising results from the small-scale thermal fluorinations in perfluorinated solvents were subsequently performed on hundreds of milligrams of 7-diazosancycline*BF$_4$. The results of these experiments are summarized in Table 2. Using perfluorinated solvents gave inconsistent results, as the BF3 adducts could not be avoided on larger scale.

A breakthrough for the thermal reaction was to use PF$_6^-$ as counterion. When PF$_6^-$ was used as counterion, the "481" byproducts (BF$_3$ adducts) were eliminated. Table 3 summarizes the results of the thermal fluorination of 7-diazosancycline*PF$_6$ in non-fluorinated, non-polar organic solvents.

TABLE 2

| Experiment | Solvent | 7-diazo-sancycline *BF$_4$ | T (° C.) | Reaction time | 7-F | BF$_3$ adducts | Comment(s) |
|---|---|---|---|---|---|---|---|
| 289-86 | perfluorodecalin | Few mg | 125 to 135 | | 51% | 8%, 7% | Reaction is slow at 125° C. |
| 289-86 | perfluorodecalin | Few mg | 135 | | 46% | 10%, 8% | |
| 289-88 | perfluorotoluene | Few mg | 135[a] | | 65% | 0.6%, 1.3% | Very little BF3 adduct, others very similar |
| 289-88 | Perfluoro-1,2-dimethylhexane | Few mg | 135[a] | | 65% | 1%, 1% | Almost identical to perfluorotoluene |
| 289-93 | Perfluoro-1,2-dimethyl hexane | Few mg | 106 | overnight | 43.4% | 10.2%, 9.3% | |
| 289-93 | Perfluorooctane, 2 mL | 100 mg | 135[a] | 1 h | 60.4% | 2.6%, 2.0% | |
| 289-93 | Perfluorooctane, 4 mL | 200 mg | 135[a] | 85 min | 52.4% | 7.4%, 6.5% | Couldn't repeat 289-93 |
| 289-93 | Perfluorooctane, 3 mL | 100 mg | reflux | 4 h | 47.5% | 6.5%, 5.6% | Couldn't repeat 289-93 |
| 289-101 | Perfluorotoluene, 4 mL | 200 mg | 135[a] | 1 h | 39% | 17.6%, 12.3% | Couldn't repeat 289-88 |
| 289-102 | Perfluoro(methyl)decalin | Few mg | 135 | 1 h | 39.8% | 16.3%, 14.9% | |
| 289-102 | Perfluorooctane | Few mg | 135[a] | 1 h | 45.2% | 13.2%, 9.6% | |
| 289-105 | perfluorononane | Few mg | 135[a] | 1 h | 36% | 16.2%, 14.4% | |

[a]Reaction was conducted in a sealed tube because the boiling point of the solvent was lower than the reaction temperature.

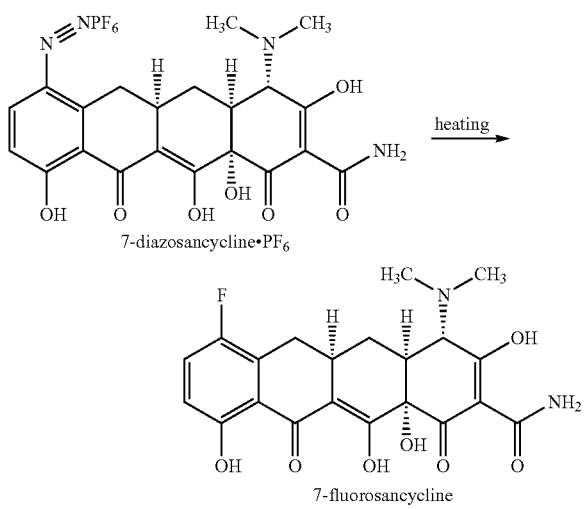

7-diazosancycline•PF$_6$ heating →

7-fluorosancycline

TABLE 3

| Experiment | Solvent | Condition(s) | 7-F | 7-H | 7-OH | Comment(s) |
|---|---|---|---|---|---|---|
| 272-56 | toluene | Microwave 150° C., 40 min | 27% | | | Material tarred |
| 272-57 | toluene | Microwave 135° C., 40 min | No reaction | | | No stirrer bar |
| 272-59 | m-xylene | 165° C., 40 min | 48% | 8% | 4% | |
| 272-67 | mesitylene | 150° C., 40 min | 46% | 11% | 8% | |
| 272-70 | none | 150° C., vacuum, 40 min | 48% | 12% | none | |

Yet further improvements in reaction yield were obtained by conducting the thermal fluorination in perfluorinated solvents. The results of the thermal fluorination of 7-diazosancycline*PF$_6$ in non-polar, organic, perfluorinated solvents are summarized in Table 4. The results of the thermal fluorination of 7-diazosancycline*PF$_6$ in perfluoro(methyl)decalin, mixture of isomers, are summarized in Table 5.

TABLE 4

| Experiment | Perfluoro solvents | 7-diazo-sancycline*PF$_6$ | T (° C.) | Time | 7-F | 7-OH |
|---|---|---|---|---|---|---|
| 289-95 | Perfluoro 1,2-methylhexane | Few mg | 135 | 1.5 h | 53% | 3.0% |
| 289-97 | Perfluorodecalin | Few mg | 135 | 1.5 h | 44% | 9.3% |
| 289-97 | perfluorotoluene | Few mg | 135 | 1.5 h | 49.6% | 1.5% |
| 289-99 | Perfluoro 1,2-dimethylhexane | Few mg | 135 | 1.5 h | 58% | 4.0% |
| 289-103 | Perfluorotoluene | some | 135 | 1.5 h | 49.3% | 2.3% |
| 289-103 | Perfluorooctane, 1 mL | 50 mg | 135 | 1.5 h | 55.6% | 2.7% |
| 289-105 | Perfluorononane | Few mg | 135 | 1.5 h | 56.8% | 3.7% |
| 289-105 | perfluorononane, 4 mL | 200 mg | 135 | 1.5 h | 57.5% | 4.9% |
| 289-109 | perfluorononane, 6 mL | 500 mg | 135 | 1.5 h | 65.9% | 6.8% |

TABLE 5

| Experiment | 7-diazo-sancycline*PF$_6$ | 7-F | Mass recovery | Yield by HPLC |
|---|---|---|---|---|
| 321-53 | 9.2 g | | | 75% |
| 321-91 | 2.1 g | 1.665 g | 100.4% | 77.4% |
| 321-95 | 1.18 g | 0.971 g | 104.2% | 75.4% |
| 321-96 | 1.18 g | 1.18 g[1] | 126.6% | 75.7% |
| 321-84 | 4.39 g | 3.5 g | 101.0% | 76.9% |

[1]Added 0.25 g SnCl$_2$ to the reaction. No effect was observed.

During the 9.2 g-scale reactions (Experiment 321-53 in Table 5), it was observed that the reaction started generating gas at 100° C. to 110° C., indicating the fluorination can occur at temperatures as low as about 100° C. After stirring at 130° C. to 135° C. for 0.5 h, the bubbling slowed dramatically, indicating that the fluorination was mostly complete.

The perfluorinated solvents known as Fluoriner™ (marketed by 3M™) were discovered as an alternative to perfluoromethyldecalin. The Fluorinert™ solvents are marketed as cooling liquids for the electronic industry. Exemplary Fluorinert™ solvents compatible with the thermal fluorination of 7-diazosancycline*PF$_6$ include, but are not limited to:

perfluorotributyl amine (FC-43), boiling point=178° C.:

perfluorotripropyl amine (FC-3283), boiling point=128° C.;

perfluoro-trialkylamines mixture (FC-40), boiling point=158-173° C.; and perfluorotripentylamine (FC-70), boiling point=215° C.

In addition to the PF$_6^-$ counterion described above, the thermal fluorination of 7-diazosancycline was also tried using other counterions. The results of the thermal fluorination of other salts of 7-diazosancycline are summarized in Table 6.

TABLE 6

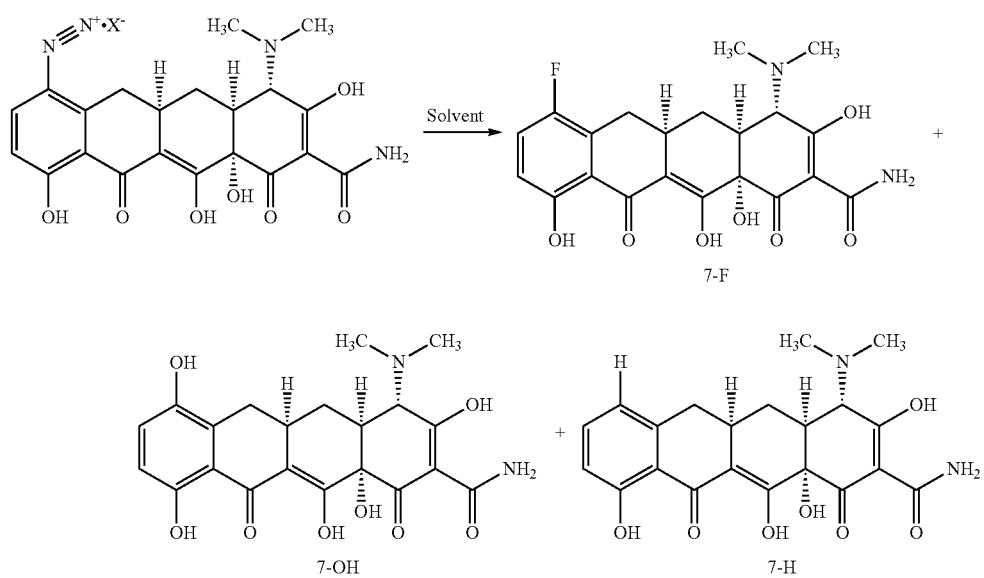

| Experiment | X | Solvent | Reaction conditions | 7-F | 7-H | 7-OH |
|---|---|---|---|---|---|---|
| 272-85 | AsF$_6$ | o-xylene | 140° C., 1 h | 24% | 30% | 2% |
| 321-29 | HSiF$_6$ | perfluoromethyldecalin | 135° C., 1 h | 35% | 24% | |

The thermal fluorination of 7-diazasancycline*$PF_6$, as disclosed herein, is more than an improvement of the thermal fluorination procedure reported in the '499 Patent. Rather, the use of 7-diazasancycline*$PF_6$ in the thermal fluorination enables the plant scale production of 7-fluoro-substituted tetracyclines, such as 7-fluorosancycline from 7-amino-substituted tetracyclines, such as 7-aminosancycline. Table 7 provides a brief comparison of the thermal fluorination reported in the '499 Patent and the thermal fluorination reported in Example 1 above.

TABLE 7

| Thermal Fluorination from | the '499 Patent | Example 1 hereinabove |
|---|---|---|
| Diazonium salt Counterion | $BF_4^-$ | $PF_6^-$ |
| Diazonium salt formation | Could not be repeated | Robust anhydrous conditions |
| Solvent | No solvent | FC-43, solvent is reusable |
| Heating | Flame, no temperature control | Controlled temperature |
| Reactor | Small glass flask | Taflon on PFA reactor |
| Scale | unknown | 200 g |
| HPLC purity | Not originally described, but repetition of the procedure showed 38% | 75% |
| Impurities | Not originally described, but repetition of the procedure showed 7-H, 7-OH and $BF_3$ adducts | 7-H, <5%<br>7-OH, ~2% |
| Isolation of 7-F product | Not originally described, but was accomplished only by preparative HPLC | Isolated by DCM extraction of free base. |

As reported in Example 1, 7-diazasancycline*$PF_6$ can be isolated from the diazotization reaction of 7-aminosancycline as a solvate or a compound containing residual solvent. Table 8 provides select examples of the residual solvent content of 7-diazasancycline*$PF_6$ salts, and the corresponding results of the thermal fluorination, expressed as HPLC purity (AUC), after the thermal fluorination reaction. Entry 1 corresponds to the thermal fluorination reported in Example 1, which was carried out at 200 g scale. Entry 5 is a representative example of a non-solvated 7-diazasancycline*$PF_6$ salt, containing only residual solvent.

TABLE 8

| Entry | Residual solvent(s) (by $^1H$ NMR) | HPLC purity (%) |
|---|---|---|
| 1 | PhCF3, 0.78 mol eq. EtOAc, 2% | 77 |
| 2 | PhCF3, 0.82 mol eq. EtOAc, 29% | 68 |
| 3 | Toluene, 0.9 mol eq. Ethyl acetate, 0.1 mol eq. | 64 |
| 4 | PhCF3, 0.3 mol eq. Diethyl ether 0.16 eq. THF 0.47 eq. | 68 |
| 5 | TBME, 10% Heptane, 14% THF, <2% | 69 |

Example 5. Photolytic Fluorination of 7-Diazosancycline Salts

A 1962 literature report (Hlavka J. J., et al., *Journal of Organic Chem.*, Vol. 27, 1962, 3674-3675) disclosed the fluorination of 7-diazosancycline tetrafluoroborate using light irradiation. Hlavka et al, reported the formation of 7-fluorosancycline without yield and the composition of other impurities.

In order to ascertain the utility of the Hlavka et al, procedure, the procedure was repeated. Although the ultraviolet (UV) wavelength was not reported in the paper, it was found that 254 nm is quite effective. Using the Hlavka et al, procedure, approximately 11.9% of 7-F was obtained, along with 26.3% 7-H and 29.9% 7-OAc as the two major byproducts. Thus, the ratio of 7-H:7-F:7-OAc was 2.2:1:2.5.

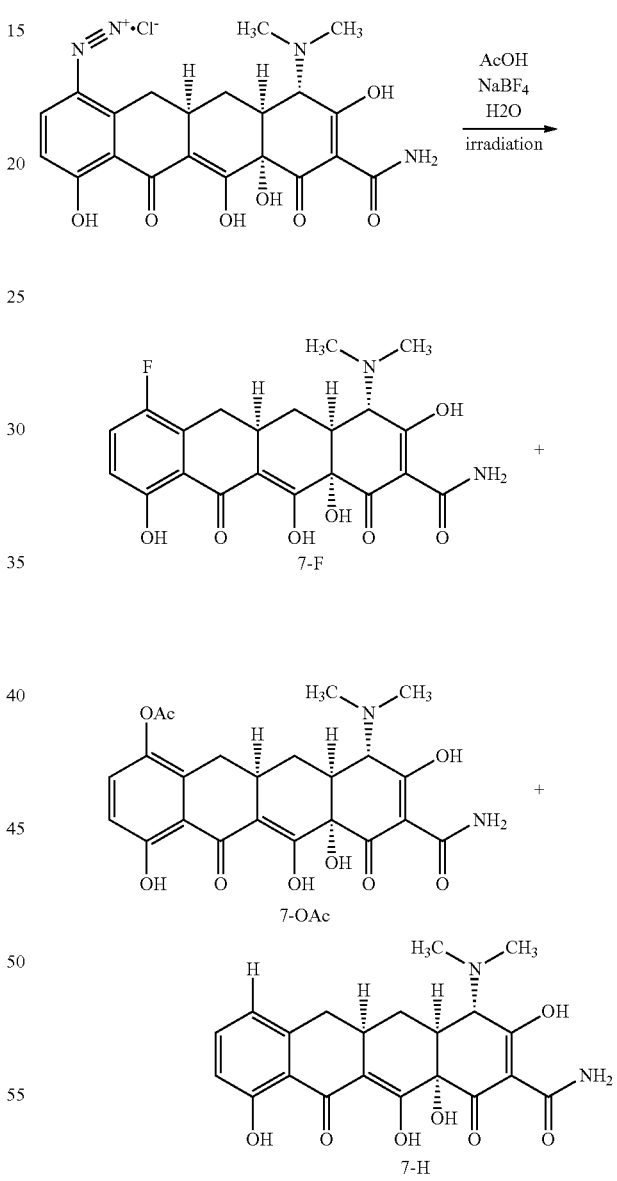

In order to improve both the yield and the purity of the photolytic fluorination of 7-diazosancycline, many solvents were screened. The results of this screen are reported in the Table 9. As can be seen from Table 9, the reactions conducted in BMIM.$BF_4$, an ionic liquid, provided 7-fluorosancycline in high yields without the formation of $BF_3$ adducts.

TABLE 9

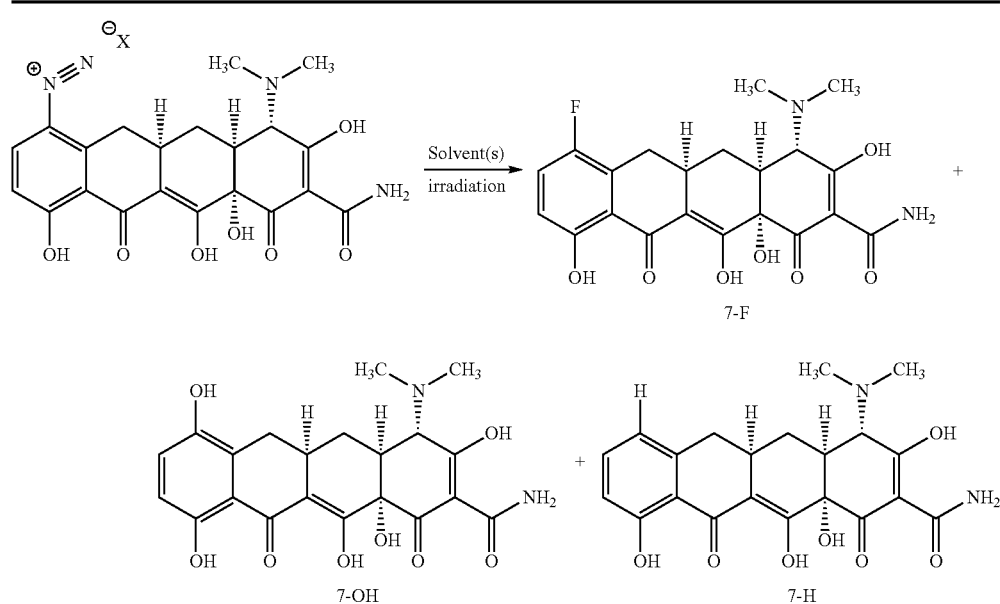

| Experiment | X | Solvent | Condition | 7-F | 7-H | 7-OH | Comment(s) |
|---|---|---|---|---|---|---|---|
| 272-24 | BF$_4$ | 48% HBF$_4$ | hγ | 19 | 6 | 7 | |
| 272-25 | BF$_4$ | DMSO | hγ | none | major | none | |
| 272-27 | BF$_4$ | HF/Py | hγ | tiny | tiny | none | |
| 272-48 | BF$_4$ | TFA, water | hγ | some | major | minor | |
| 272-52 | BF$_4$ | toluene | hγ | No reaction | | | Not soluble |
| 272-54 | BF$_4$ | CF$_3$-benzene | hγ overnight | No reaction | | | Not soluble |
| 272-61 | BF$_4$ | ACN | hγ | tiny | | | |
| 272-62 | BF$_4$ | TFA | hγ | 22% | none | 42% | SM 29% |
| 272-64 | BF$_4$ | Conc H$_2$SO$_4$ | hγ | none | none | major | |
| 272-72 | BF$_4$ | MeSO$_3$H | hγ | none | | | |
| 272-72 | BF$_4$ | NEt$_3$•HF | hγ | 27% | 36% | | |
| 272-72 | BF$_4$ | HBF$_4$•Et$_2$O | hγ | 53% | 2% | none | Lots of BF3 adducts |
| 272-72 | BF$_4$ | DCM, MeOH | hγ | tiny | major | Some | 7-OMe |
| 272-72 | BF$_4$ | NMP | hγ | none | major | none | |
| 272-72 | BF$_4$ | IPA/NEt$_3$ | hγ | none | major | none | |
| 272-74 | BF$_4$ | BMIM•BF$_4$ | hγ | 55% | 22% | | |
| 272-75 | BF$_4$ | Cl$_3$CCN | hγ | some | some | | Not soluble |
| 272-75 | BF$_4$ | Water, NEt$_3$ | hγ | none | major | none | |
| 272-77 | BF$_4$ | DCM | hγ | 1.4% | 7.4% | | difluorotriphenylsilicate |
| 272-31 | PF$_6$ | water | hγ | none | | | |
| 272-31 | PF$_6$ | DMSO | hγ | none | | | |
| 464-1 | PF$_6$ | BMIM•BF$_4$ | hγ | 71.9 | 13.9 | | |
| 272-86 | AsF$_6$ | BMIM•BF$_4$ | hγ | 40% | 32% | 2% | |

As a result of the experiments in BMIM.BF$_4$ reported in Table 9, the photolytic fluorination of 7-diazosancycline was scaled up to 100 mg in four different ionic liquids. The results are summarized in Table 10. For example, when 1-butyl-3-methyl-imidazolium tetrafluoroborate (BMIM.BF4) was used as solvent in a 100-mg scale reaction, the reaction gave 58.8% 7-F together with 7-H (17.7%) as the major byproduct (see Experiment 289-48 in Table 9). Using preparative HPLC, 70 mg was isolated from this reaction as a mixture of 7-F and 7-H. The reaction in BMIM.BF4 was scaled up to 1 g, with a similar reaction profile by HPLC.

TABLE 10

| Experiment | Ionic liquid | Time | 7-F | 7-H | Comment(s) |
|---|---|---|---|---|---|
| 289-48 | I | 18 h | 59% | 18% | HPLC isolated 70 mg of 7-F and 7-H |
| 289-49 | II | 40 h | 55% | 24% | Isolated 45 mg |
| 289-58 | III | 24 h | | | Very slow, most are decomposed |
| 289-66 | IV | 18 h | 57% | 14% | 25 mg 7-diazosancycline*$PF_6^-$ in 1 mL IV was used |

I: 1-butyl-3-methylimidazolium tetrafluoroborate (BMIM•$BF_4$)
II: 1-butyl-2,3-dimethylimidazolim tetrafluoroborate
III: 1-butyl-3-methylpyridinium tetrafluoroborate
IV: 1-butyl-3-methylimidazolium hexafluorophosphate

Example 6. Fluorination Reactions of 7-Diazo-9-Substituted Tetracyclines

Several fluorination conditions to produce eravacycline were explored. For example, 7-diazosancycline hexafluorophosphate can be transformed into 7-fluorosancycline by heating 7-diazosancycline hexafluorophosphate in perfluorodecalin or perfluorooctane at 120° C. for 1 h. Both reactions gave 36% 7-fluorosancycline by LC. The reactions were also scaled up to 100 mg, and the results were similar. The results of other fluorination reactions to produce eravacycline are summarized in Table 11.

TABLE 11

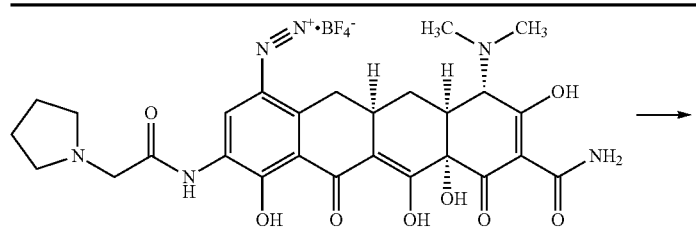

TABLE 11-continued

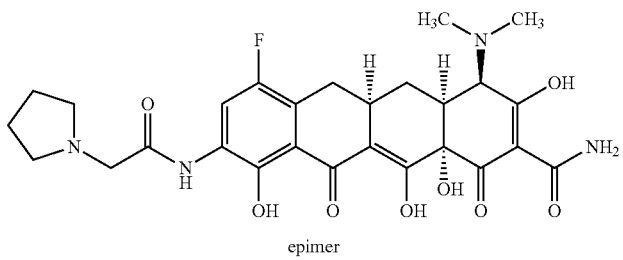 [SMILES: CN(C)[C@H]1C(O)=C(C(N)=O)C(=O)[C@@]2(O)C(O)=C3C(=O)c4c(O)c(NC(=O)CN5CCCC5)cc(F)c4C[C@H]3C[C@@H]12]
epimer

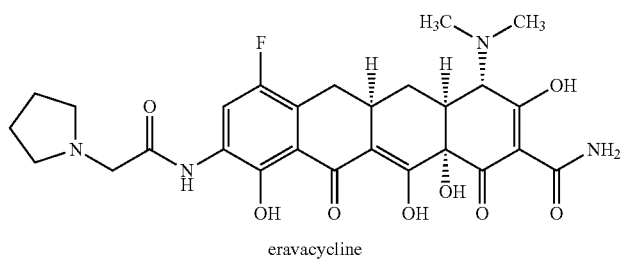 [SMILES: CN(C)[C@@H]1C(O)=C(C(N)=O)C(=O)[C@@]2(O)C(O)=C3C(=O)c4c(O)c(NC(=O)CN5CCCC5)cc(F)c4C[C@H]3C[C@@H]12]
eravacycline

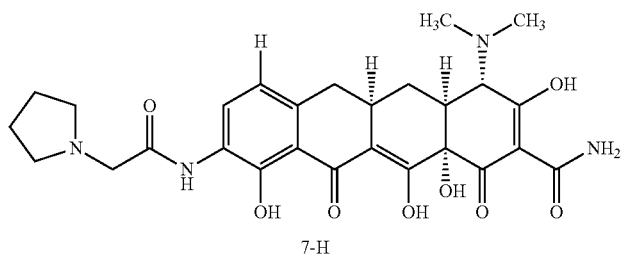 [SMILES: CN(C)[C@@H]1C(O)=C(C(N)=O)C(=O)[C@@]2(O)C(O)=C3C(=O)c4c(ccc(NC(=O)CN5CCCC5)c4O)C[C@H]3C[C@@H]12]
7-H

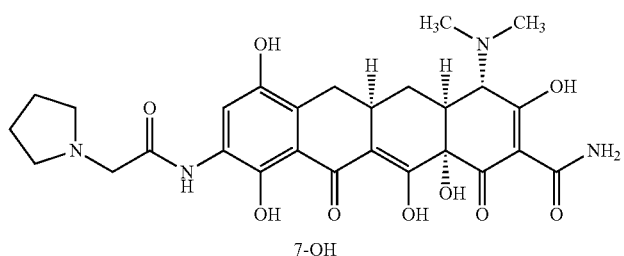 [SMILES: CN(C)[C@@H]1C(O)=C(C(N)=O)C(=O)[C@@]2(O)C(O)=C3C(=O)c4c(O)c(NC(=O)CN5CCCC5)cc(O)c4C[C@H]3C[C@@H]12]
7-OH

| Experiment | Solvent | Condition(s) | eravacycline | 7-H + epimer | 7-OH | Comment(s) |
|---|---|---|---|---|---|---|
| 289-52 | mesitylene | 150° C., 40 min | 28% | 19% | 7% | |
| 289-52 | BMIM•BF$_4$ | hγ, 18 h | 35% | 31% | | |
| 289-53 | o-xylene | Microwave 135° C., 4.5 h | 31% | 21% | 8% | SM remained |
| 289-54 | 48% HBF$_4$ | hγ, 5 h | 38% | 11% | 26% | |
| 289-57 | SiO$_2$ | 135° C. | 26% | 18% | 12% | |
| 289-57 | PhCl | 135° C., 1.5 h | 36% | 17% | 7% | 10% 7-Cl |
| 289-57 | PhCl | 125° C., 1.5 h | | | | Not complete |
| 289-65 | PhCl | 125° C., 3 h | 22% | 13% | 5% | Still not complete |
| 289-62 | 48% HBF$_4$ | rt | | 100% | | Added Cu |
| 289-68 | MgSO$_4$ | 140° C., 1 h | 35% | 19% | 6% | |
| 289-81 | perfluorodecalin | 120° C., 1 h | 34% | 19% | 10% | |
| 289-81 | perfluorooctane | 120° C., 1 h | 36% | 19% | 10% | |

Experiment 289-54 was scaled up to 150 mg of diazonium salt (see Example 1). After preparative HPLC, 35 mg of eravacycline was obtained. A $PF_6^-$ diazonium salt was also prepared and subjected to photolytic fluorination conditions. However, the fluorination gave mostly 7-OH.

Fluorination reactions involving other 7-diazo-9-substituted tetracyclines were also explored. The results of fluorination reactions involving other 7-diazo-9-substituted tetracyclines are summarized in Table 12.

TABLE 12

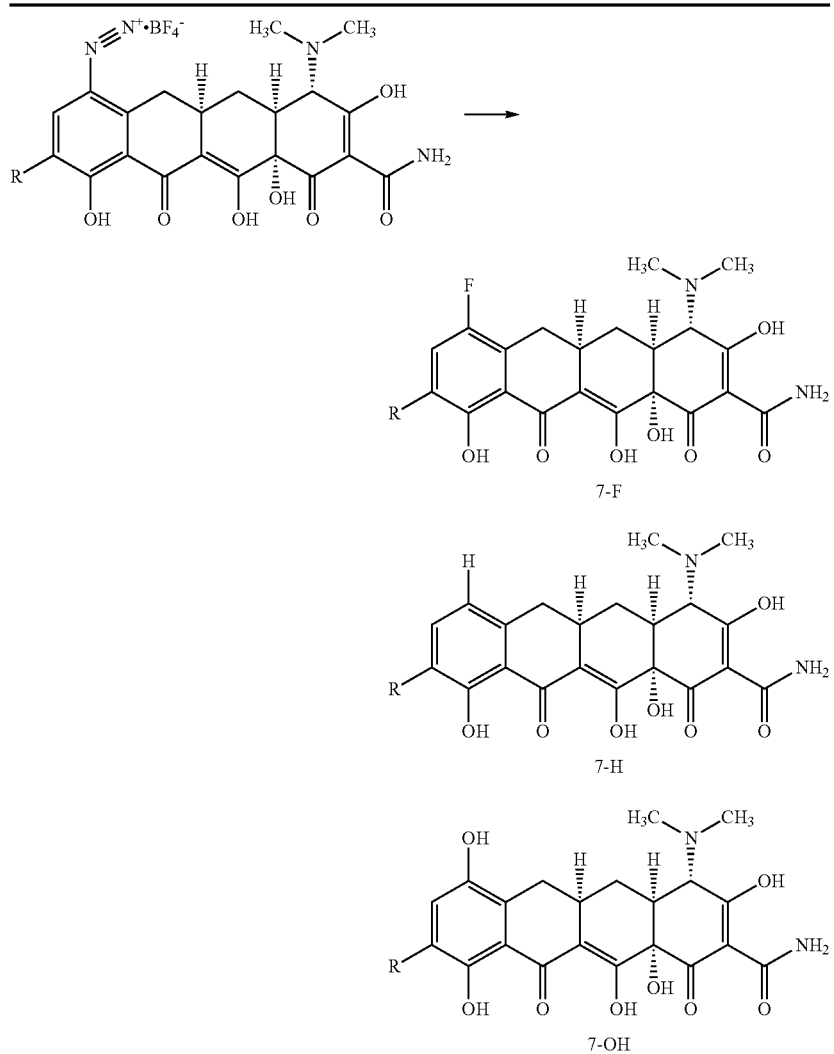

| Experiment | R | Solvent | Condition(s) | 7-F | 7-H | 7-OH | Comment |
|---|---|---|---|---|---|---|---|
| 272-50 | —NMe₂ | 48% HBF₄ | hν | 34% | 5.4% | 23% | |
| 272-60 | —NO₂ | toluene | 135° C. | none | major | | |
| 321-31 | —NO₂ | perfluoromethyldecalin | 135° C. | | major | | |
| 272-78 | —NO₂ | BMIM•BF₄ | hν | 29% | 25% | 2% | slow |
| 272-84 | —N(H)Ac | o-xylene | hν | tiny | tiny | | messy |
| 272-88 | —N(H)Ac | BMIM•BF₄ | hν | 39% | 21% | | |
| 289-7 | —Br | BMIM•BF₄ | hν | 18% | 57% | | |
| 289-13 | MeOC(O)N(H)— | 48% HBF₄ | hν | 36% | none | 21% | |
| 289-15 | MeOC(O)N(H)— | Water | hν | none | major | none | |
| 289-15 | MeOC(O)N(H)— | 48% HBF₄ | hν | 46% | none | 25% | |
| 289-15 | MeOC(O)N(H)— | BMIM•BF₄ | hν | 56% | 18% | 9% | |
| 289-20 | MeOC(O)N(H)— | Mesitylene | 150° C., 40 min | 30% | 5% | 8% | 19% SM |
| 289-20 | MeOC(O)N(H)— | BMIM•BF₄ | hν | 48% | 20% | 10% | |
| 289-17 | CbzNH— | BMIM•BF₄ | hν | | | | messy |
| 289-19 | CbzNH— | Mesitylene | 150° C. | | | | no 7-F |
| 289-30 | BnNH— | 48% HBF₄ | hν | none | | | messy |

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by Structural Formula I:

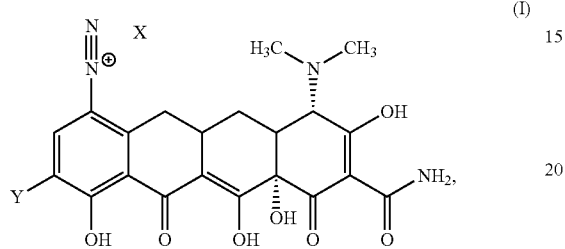

(I)

or a salt, solvate or combination thereof, wherein:

X is $PF_6^-$, $AsF_6^-$ or $HSiF_6^-$;

Y is selected from the group consisting of hydrogen, halo, nitro, —($C_1$-$C_7$)alkyl, carbocyclyl, —($C_1$-$C_4$)alkylene-N($R^A$)($R^B$), —($C_1$-$C_4$)alkylene-N($R^F$)—C(O)—[C($R^D$)($R^E$)]$_{0-4}$—N($R^A$)($R^B$), —CH=N—$OR^A$, —N($R^A$)($R^B$), —N($R^F$)—C(O)—[C($R^D$)($R^E$)]$_{1-4}$—N($R^A$)($R^B$), —N($R^F$)—C(O)—N($R^A$)($R^B$), —N($R^F$)—C(O)—$OR^A$, —N($R^F$)—C(O)—($C_1$-$C_6$)alkyl, —N($R^F$)—C(O)-heterocyclyl, —N($R^F$)—C(O)-heteroaryl, —N($R^F$)—C(O)-carbocyclyl, —N($R^F$)—C(O)-aryl, —N($R^F$)—S(O)$_m$—($C_1$-$C_4$)alkylene-N($R^A$)($R^B$), —N($R^F$)—S(O)$_m$—($C_1$-$C_4$)alkylene-carbocyclyl, and —N($R^F$)—S(O)$_m$—($C_1$-$C_4$)alkylene-aryl wherein:

each $R^A$ and $R^B$ are independently selected from the group consisting of hydrogen, ($C_1$-$C_7$)alkyl, —O—($C_1$-$C_7$)alkyl, —($C_0$-$C_6$)alkylene-carbocyclyl, —($C_0$-$C_6$)alkylene-aryl, —($C_0$-$C_6$)alkylene-heterocyclyl, —($C_0$-$C_6$)alkylene-heteroaryl, —($C_1$-$C_6$)alkylene-O—($C_1$-$C_7$)alkyl, —($C_1$-$C_6$)alkylene-O-carbocyclyl, —($C_1$-$C_6$)alkylene-O-aryl, —($C_1$-$C_6$)alkylene-O-heterocyclyl, —($C_1$-$C_6$)alkylene-O-heteroaryl, —S(O)$_m$—($C_1$-$C_6$)alkyl, —($C_0$-$C_4$)alkylene-S(O)$_m$-carbocyclyl, —($C_0$-$C_4$)alkylene-S(O)$_m$-aryl, —($C_0$-$C_4$)alkylene-S(O)$_m$-heterocyclyl and —($C_0$-$C_4$)alkylene-S(O)$_m$-heteroaryl; or $R^A$ and $R^B$ taken together with the nitrogen atom to which they are bound form a heterocyclyl or heteroaryl, wherein the heterocycle or heteroaryl optionally comprises 1 to 4 additional heteroatoms independently selected from the group consisting of N, S and O;

each $R^D$ and each $R^E$ is independently selected from the group consisting of hydrogen, ($C_1$-$C_6$)alkyl, carbocyclyl, aryl, heterocyclyl or heteroaryl, or $R^D$ and $R^E$ taken together with the carbon atom to which they are bound form a 3-7 membered carbocyclyl, or a 4-7 membered heterocyclyl, wherein the heterocyclyl formed by $R^D$ and $R^E$ optionally comprises one to two additional heteroatoms independently selected from the group consisting of N, S and O;

$R^F$ is selected from the group consisting of hydrogen, ($C_1$-$C_7$)alkyl, carbocyclyl, aryl and heteroaryl; and m is 0, 1 or 2, wherein:

each carbocyclyl, aryl, heterocyclyl or heteroaryl is optionally and independently substituted with one or more substituents independently selected from the group consisting of halo, —($C_1$-$C_4$)alkyl, —OH, =O, —O—($C_1$-$C_4$)alkyl, —($C_1$-$C_4$)alkylene-O—($C_1$-$C_4$)alkyl, halo-substituted —($C_1$-$C_4$)alkyl, halo-substituted —O—($C_1$-$C_4$)alkyl, —C(O)—($C_1$-$C_4$)alkyl, —C(O)-(fluoro-substituted-($C_1$-$C_4$)alkyl), —S(O)$_m$—($C_1$-$C_4$)alkyl, —N($R^G$)($R^G$), and CN;

each alkyl in the group represented by $R^A$, $R^B$, $R^D$ and $R^E$ is optionally and independently substituted with one or more substituents independently selected from the group consisting of halo, —($C_1$-$C_4$)alkyl, —OH, —O—($C_1$-$C_7$)alkyl, —($C_1$-$C_4$)alkylene-O—($C_1$-$C_4$)alkyl, fluoro-substituted-($C_1$-$C_4$)alkyl, —S(O)$_m$—($C_1$-$C_4$)alkyl, and —N($R^G$)($R^G$), wherein each $R^G$ is hydrogen or ($C_1$-$C_4$)alkyl, wherein each alkyl in the group represented by $R^G$ is optionally and independently substituted with one or more substituents independently selected from the group consisting of —($C_1$-$C_4$)alkyl, ($C_3$-$C_6$)cycloalkyl, halo, —OH, —O—($C_1$-$C_4$)alkyl, and ($C_1$-$C_4$)alkyl-O—($C_1$-$C_4$)alkyl.

2. The compound of claim 1, wherein the compound represented by Structural Formula I is a solvate or a salt and a solvate.

3. The compound of claim 2, wherein the compound represented by Structural Formula I is a (trifluoromethyl) benzene solvate.

4. The compound of claim 1, wherein the solvate comprises from about 0.1 to about 1.0 molar equivalents of solute per molar equivalent of the compound of Structural Formula I.

5. The compound of claim 4, wherein the solvate comprises about 0.8 molar equivalents of solute per molar equivalent of the compound of Structural Formula I.

6. The compound of claim 1, wherein X is $PF_6^-$.

7. The compound of claim 1, wherein Y is hydrogen.

8. The compound of claim 1, represented by Structural Formula Ib:

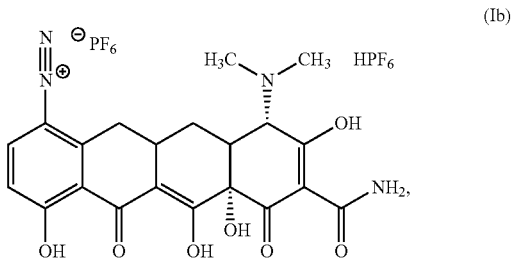

(Ib)

or a solvate thereof.

9. A method of preparing a compound represented by Structural Formula II:

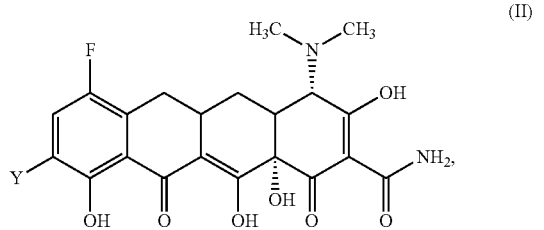

(II)

or a salt, solvate or combination thereof, wherein:
Y is selected from the group consisting of hydrogen, halo, nitro, —($C_1$-$C_7$)alkyl, carbocyclyl, —($C_1$-$C_4$)alkylene-N($R^A$)($R^B$), —($C_1$-$C_4$)alkylene-N($R^F$)—C(O)—[C($R^D$)($R^E$)]$_{0-4}$—N($R^A$)($R^B$), —CH=N—O$R^A$, —N($R^A$)($R^B$), —N($R^F$)—C(O)—[C($R^D$)($R^E$)]$_{1-4}$—N($R^A$)($R^B$), —N($R^F$)—C(O)—N($R^A$)($R^B$), —N($R^F$)—C(O)—O$R^A$, —N($R^F$)—C(O)—($C_1$-$C_6$)alkyl, —N($R^F$)—C(O)-heterocyclyl, —N($R^F$)—C(O)-heteroaryl, —N($R^F$)—C(O)-carbocyclyl, —N($R^F$)—C(O)-aryl, —N($R^F$)—S(O)$_m$—($C_1$-$C_4$)alkylene-N($R^A$)($R^B$), —N($R^F$)—S(O)$_m$—($C_1$-$C_4$)alkylene-carbocyclyl, and —N($R^F$)—S(O)$_m$—($C_1$-$C_4$)alkylene-aryl wherein:
each $R^A$ and $R^B$ are independently selected from the group consisting of hydrogen, ($C_1$-$C_7$)alkyl, —O—($C_1$-$C_7$)alkyl, —($C_0$-$C_6$)alkylene-carbocyclyl, —($C_0$-$C_6$)alkylene-aryl, —($C_0$-$C_6$)alkylene-heterocyclyl, —($C_0$-$C_6$)alkylene-heteroaryl, —($C_1$-$C_6$)alkylene-O—($C_1$-$C_7$)alkyl, —($C_1$-$C_6$)alkylene-O-carbocyclyl, —($C_1$-$C_6$)alkylene-O-aryl, —($C_1$-$C_6$)alkylene-O-heterocyclyl, —($C_1$-$C_6$)alkylene-O-heteroaryl, —S(O)$_m$—($C_1$-$C_6$)alkyl, —($C_0$-$C_4$)alkylene-S(O)$_m$-carbocyclyl, —($C_0$-$C_4$)alkylene-S(O)$_m$-aryl, —($C_0$-$C_4$)alkylene-S(O)$_m$-heterocyclyl and —($C_0$-$C_4$)alkylene-S(O)$_m$-heteroaryl; or
$R^A$ and $R^B$ taken together with the nitrogen atom to which they are bound form a heterocyclyl or heteroaryl, wherein the heterocycle or heteroaryl optionally comprises 1 to 4 additional heteroatoms independently selected from the group consisting of N, S and O;
each $R^D$ and each $R^E$ is independently selected from the group consisting of hydrogen, ($C_1$-$C_6$)alkyl, carbocyclyl, aryl, heterocyclyl or heteroaryl, or
$R^D$ and $R^E$ taken together with the carbon atom to which they are bound form a 3-7 membered carbocyclyl, or a 4-7 membered heterocyclyl, wherein the heterocyclyl formed by $R^D$ and $R^E$ optionally comprises one to two additional heteroatoms independently selected from the group consisting of N, S and O;
$R^F$ is selected from the group consisting of hydrogen, ($C_1$-$C_7$)alkyl, carbocyclyl, aryl and heteroaryl; and m is 0, 1 or 2, wherein:
each carbocyclyl, aryl, heterocyclyl or heteroaryl is optionally and independently substituted with one or more substituents independently selected from the group consisting of halo, —($C_1$-$C_4$)alkyl, —OH, =O, —O—($C_1$-$C_4$)alkyl, —($C_1$-$C_4$)alkylene-O—($C_1$-$C_4$)alkyl, halo-substituted —($C_1$-$C_4$)alkyl, halo-substituted —O—($C_1$-$C_4$)alkyl, —C(O)—($C_1$-$C_4$)alkyl, —C(O)-(fluoro-substituted-($C_1$-$C_4$)alkyl), —S(O)$_m$—($C_1$-$C_4$)alkyl, —N($R^G$)($R^G$), and CN;

each alkyl in the group represented by $R^A$, $R^B$, $R^D$ and $R^E$ is optionally and independently substituted with one or more substituents independently selected from the group consisting of halo, —($C_1$-$C_4$)alkyl, —OH, —O—($C_1$-$C_7$)alkyl, —($C_1$-$C_4$)alkylene-O—($C_1$-$C_4$)alkyl, fluoro-substituted-($C_1$-$C_4$)alkyl, —S(O)$_m$—($C_1$-$C_4$)alkyl, and —N($R^G$)($R^G$), wherein each $R^G$ is hydrogen or ($C_1$-$C_4$)alkyl, wherein each alkyl in the group represented by $R^G$ is optionally and independently substituted with one or more substituents independently selected from the group consisting of —($C_1$-$C_4$)alkyl, ($C_3$-$C_6$)cycloalkyl, halo, —OH, —O—($C_1$-$C_4$)alkyl, and ($C_1$-$C_4$)alkyl-O—($C_1$-$C_4$)alkyl,
the method comprising:
heating a suspension comprising a non-polar organic solvent and a compound of Structural Formula I:

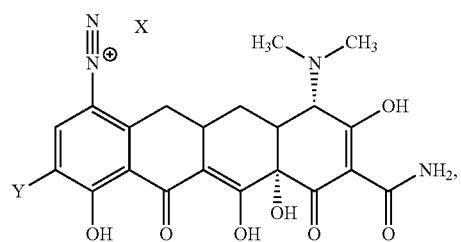

(I)

or a salt, solvate or combination thereof, wherein X is $PF_6^-$, $AsF_6^-$ or $HSiF_6^-$; and Y is as defined above for the compound of Structural Formula II,
at a temperature of from about 95° C. to about 200° C. to provide the compound of Structural Formula II, or the salt, solvate or combination thereof.

10. A compound represented by Structural Formula X:

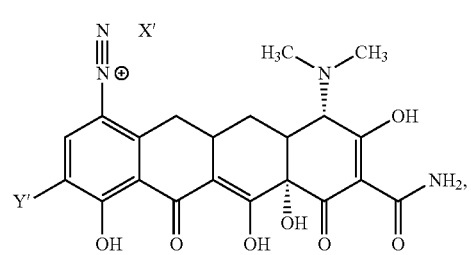

(X)

or a salt, solvate or combination thereof, wherein:
X' is $BF_4^-$, $PF_6^-$, $AsF_6^-$ or $HSiF_6^-$;
Y' is selected from the group consisting of halo, nitro, —N($R^A$)($R^B$), —N($R^F$)—C(O)—[C($R^D$)($R^E$)]$_{1-4}$—N($R^A$)($R^B$), —N($R^F$)—C(O)—N($R^A$)($R^B$), —N($R^F$)—C(O)—($C_1$-$C_6$)alkyl, —N($R^F$)—C(O)—O$R^A$, —N($R^F$)—C(O)-heterocyclyl, —N($R^F$)—C(O)-heteroaryl, —N($R^F$)—C(O)-carbocyclyl, —N($R^F$)—C(O)-aryl, —N($R^F$)—S(O)$_m$—($C_1$-$C_4$)alkylene-N($R^A$)($R^B$), —N($R^F$)—S(O)$_m$—($C_1$-$C_4$)alkylene-carbocyclyl, and —N($R^F$)—S(O)$_m$—($C_1$-$C_4$)alkylene-aryl;
$R^A$ and $R^B$ are independently selected from the group consisting of hydrogen, ($C_1$-$C_7$)alkyl, —O—($C_1$-$C_7$)alkyl, —($C_0$-$C_6$)alkylene-carbocyclyl, —($C_0$-$C_6$)alkylene-aryl, —($C_0$-$C_6$)alkylene-heterocyclyl, —($C_0$-$C_6$)alkylene-heteroaryl, —($C_1$-$C_6$)alkylene- O—(C$_1$-C$_7$)alkyl, —(C$_1$-C$_6$)alkylene-O-carbocyclyl, —(C$_1$-C$_6$)alkylene-O-aryl, —(C$_1$-C$_6$)alkylene-O-heterocyclyl, —(C$_1$-C$_6$)alkylene-O-heteroaryl, —S(O)$_m$—(C$_1$-C$_6$)alkyl, —(C$_0$-C$_4$)alkylene-S(O)$_m$-carbocyclyl, —(C$_0$-C$_4$)alkylene-S(O)$_m$-aryl, —(C$_0$-C$_4$)alkylene-S(O)$_m$-heterocyclyl and —(C$_0$-C$_4$)alkylene-S(O)$_m$-heteroaryl; or R$^A$ and R$^B$ taken together with the nitrogen atom to which they are bound form a heterocyclyl or heteroaryl, wherein the heterocycle or heteroaryl optionally comprises 1 to 4 additional heteroatoms independently selected from the group consisting of N, S and O;

R$^D$ and R$^E$ are each independently selected from the group consisting of hydrogen, (C$_1$-C$_6$)alkyl, carbocyclyl, aryl, heterocyclyl or heteroaryl; or R$^D$ and R$^E$ taken together with the carbon atom to which they are bound form a 3-7 membered carbocyclyl or a 4-7 membered heterocyclyl, wherein the heterocyclyl formed by R$^D$ and R$^E$ optionally comprises one or two additional heteroatoms independently selected from the group consisting of N, S and O;

R$^F$ is selected from the group consisting of hydrogen, (C$_1$-C$_7$)alkyl, carbocyclyl, aryl and heteroaryl; and m is 0, 1 or 2, wherein:

each carbocyclyl, aryl, heterocyclyl or heteroaryl is optionally and independently substituted with one or more substituents independently selected from the group consisting of halo, —(C$_1$-C$_4$)alkyl, —OH, =O, —O—(C$_1$-C$_4$)alkyl, —(C$_1$-C$_4$)alkylene-O—(C$_1$-C$_4$)alkyl, halo-substituted —(C$_1$-C$_4$)alkyl, halo-substituted —O—(C$_1$-C$_4$)alkyl, —C(O)—(C$_1$-C$_4$)alkyl, —C(O)-(fluoro-substituted-(C$_1$-C$_4$)alkyl), —S(O)$_m$—(C$_1$-C$_4$)alkyl, —N(R$^G$)(R$^G$), and CN; and each alkyl in the group represented by R$^A$, R$^B$, R$^D$ and R$^E$ is optionally and independently substituted with one or more substituents independently selected from the group consisting of halo, —(C$_1$-C$_4$)alkyl, —OH, —O—(C$_1$-C$_7$)alkyl, —(C$_1$-C$_4$)alkylene-O—(C$_1$-C$_4$)alkyl, fluoro-substituted-(C$_1$-C$_4$)alkyl, —S(O)$_m$—(C$_1$-C$_4$)alkyl, and —N(R$^G$)(R$^G$), wherein each R$^G$ is hydrogen or (C$_1$-C$_4$)alkyl, wherein each alkyl in the group represented by R$^G$ is optionally and independently substituted with one or more substituents independently selected from the group consisting of —(C$_1$-C$_4$)alkyl, (C$_3$-C$_6$)cycloalkyl, halo, —OH, —O—(C$_1$-C$_4$)alkyl, and (C$_1$-C$_4$)alkyl-O—(C$_1$-C$_4$)alkyl.

11. A method of preparing a compound represented by Structural Formula II:

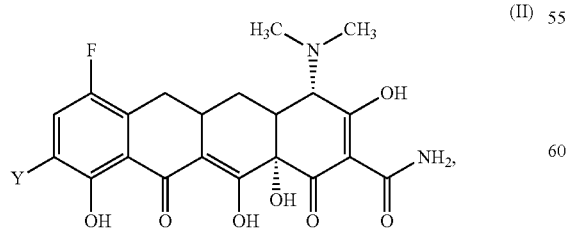

(II)

or a salt, solvate or combination thereof, wherein:
Y is selected from the group consisting of hydrogen, halo, nitro, —(C$_1$-C$_7$)alkyl, carbocyclyl, —(C$_1$-C$_4$)alkylene-N(R$^A$)(R$^B$), —(C$_1$-C$_4$)alkylene-N(R$^F$)—C(O)—[C(R$^D$)(R$^E$)]$_{0-4}$—N(R$^A$)(R$^B$), —CH=N—OR$^A$, —N(R$^A$)(R$^B$), —N(R$^F$)—C(O)—[C(R$^D$)(R$^E$)]$_{1-4}$—N(R$^A$)(R$^B$), —N(R$^F$)—C(O)—N(R$^A$)(R$^B$), —N(R$^F$)—C(O)—(C$_1$-C$_6$)alkyl, —N(R$^F$)—C(O)—OR$^A$, —N(R$^F$)—C(O)-heterocyclyl, —N(R$^F$)—C(O)-heteroaryl, —N(R$^F$)—C(O)-carbocyclyl, —N(R$^F$)—C(O)-aryl, —N(R$^F$)—S(O)$_m$—(C$_1$-C$_4$)alkylene-N(R$^A$)(R$^B$), —N(R$^F$)—S(O)$_m$—(C$_1$-C$_4$)alkylene-carbocyclyl, and —N(R$^F$)—S(O)$_m$—(C$_1$-C$_4$)alkylene-aryl, wherein:

each R$^A$ and R$^B$ are independently selected from the group consisting of hydrogen, (C$_1$-C$_7$)alkyl, —O—(C$_1$-C$_7$)alkyl, —(C$_0$-C$_6$)alkylene-carbocyclyl, —(C$_0$-C$_6$)alkylene-aryl, —(C$_0$-C$_6$)alkylene-heterocyclyl, —(C$_0$-C$_6$)alkylene-heteroaryl, —(C$_1$-C$_6$)alkylene-O—(C$_1$-C$_7$)alkyl, —(C$_1$-C$_6$)alkylene-O-carbocyclyl, —(C$_1$-C$_6$)alkylene-O-aryl, —(C$_1$-C$_6$)alkylene-O-heterocyclyl, —(C$_1$-C$_6$)alkylene-O-heteroaryl, —S(O)$_m$—(C$_1$-C$_6$)alkyl, —(C$_0$-C$_4$)alkylene-S(O)$_m$-carbocyclyl, —(C$_0$-C$_4$)alkylene-S(O)$_m$-aryl, —(C$_0$-C$_4$)alkylene-S(O)$_m$-heterocyclyl and —(C$_0$-C$_4$)alkylene-S(O)$_m$-heteroaryl; or R$^A$ and R$^B$ taken together with the nitrogen atom to which they are bound form a heterocyclyl or heteroaryl, wherein the heterocycle or heteroaryl optionally comprises 1 to 4 additional heteroatoms independently selected from the group consisting of N, S and O;

each R$^D$ and each R$^E$ is independently selected from the group consisting of hydrogen, (C$_1$-C$_6$)alkyl, carbocyclyl, aryl, heterocyclyl or heteroaryl, or R$^D$ and R$^E$ taken together with the carbon atom to which they are bound form a 3-7 membered carbocyclyl, or a 4-7 membered heterocyclyl, wherein the heterocyclyl formed by R$^D$ and R$^E$ optionally comprises one to two additional heteroatoms independently selected from the group consisting of N, S and O;

R$^F$ is selected from the group consisting of hydrogen, (C$_1$-C$_7$)alkyl, carbocyclyl, aryl and heteroaryl; and m is 0, 1 or 2, wherein:

each carbocyclyl, aryl, heterocyclyl or heteroaryl is optionally and independently substituted with one or more substituents independently selected from the group consisting of halo, —(C$_1$-C$_4$)alkyl, —OH, =O, —O—(C$_1$-C$_4$)alkyl, —(C$_1$-C$_4$)alkylene-O—(C$_1$-C$_4$)alkyl, halo-substituted —(C$_1$-C$_4$)alkyl, halo-substituted —O—(C$_1$-C$_4$)alkyl, —C(O)—(C$_1$-C$_4$)alkyl, —C(O)-(fluoro-substituted-(C$_1$-C$_4$)alkyl), —S(O)$_m$—(C$_1$-C$_4$)alkyl, —N(R$^G$)(R$^G$), and CN;

each alkyl in the group represented by R$^A$, R$^B$, R$^D$ and R$^E$ is optionally and independently substituted with one or more substituents independently selected from the group consisting of halo, —(C$_1$-C$_4$)alkyl, —OH, —O—(C$_1$-C$_7$)alkyl, —(C$_1$-C$_4$)alkylene-O—(C$_1$-C$_4$)alkyl, fluoro-substituted-(C$_1$-C$_4$)alkyl, —S(O)$_m$—(C$_1$-C$_4$)alkyl, and —N(R$^G$)(R$^G$), wherein each R$^G$ is hydrogen or (C$_1$-C$_4$)alkyl, wherein each alkyl in the group represented by R$^G$ is optionally and independently substituted with one or more substituents independently selected from the group consisting of —(C$_1$-C$_4$)alkyl, (C$_3$-C$_6$)cycloalkyl, halo, —OH, —O—(C$_1$-C$_4$)alkyl, and (C$_1$-C$_4$)alkyl-O—(C$_1$-C$_4$)alkyl, the method comprising:
irradiating a solution comprising an ionic liquid and a compound of Structural Formula XI:
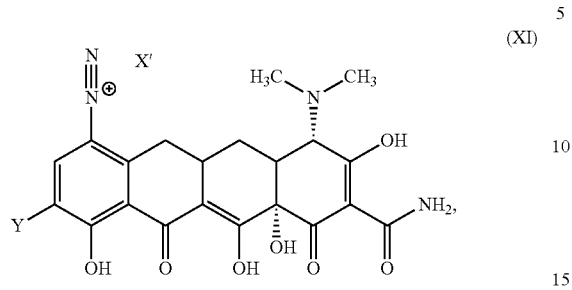
(XI)
or a salt, solvate or combination thereof, wherein X' is $BF_4^-$, $PF_6^-$, $AsF_6^-$ or $HSiF_6^-$; and Y is as defined above for the compound of Structural Formula II, to provide the compound of Structural Formula II, or the salt, solvate or combination thereof.
* * * * *